(12) United States Patent
Witschel et al.

(10) Patent No.: US 7,879,761 B2
(45) Date of Patent: *Feb. 1, 2011

(54) HETEROAROYL-SUBSTITUTED SERINEAMIDES

(75) Inventors: Matthias Witschel, Bad Dürkheim (DE); Cyrill Zagar, Mannheim (DE); Eike Hupe, Ludwigshafen (DE); Toralf Kühn, Mannheim (DE); William Karl Moberg, Hassloch (DE); Liliana Parra Rapado, Offenburg (DE); Frank Stelzer, Mannheim (DE); Andrea Vescovi, Mannheim (DE); Michael Rack, Eppelheim (DE); Robert Reinhard, Ludwigshafen (DE); Bernd Sievernich, Haβloch (DE); Klaus Groβmann, Neuhofen (DE); Thomas Ehrhardt, Speyer (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 398 days.

This patent is subject to a terminal disclaimer.

(21) Appl. No.: 11/915,227

(22) PCT Filed: Mar. 29, 2006

(86) PCT No.: PCT/EP2006/061128

§ 371 (c)(1),
(2), (4) Date: Nov. 21, 2007

(87) PCT Pub. No.: WO2006/125687

PCT Pub. Date: Nov. 30, 2006

(65) Prior Publication Data

US 2008/0200338 A1 Aug. 21, 2008

(30) Foreign Application Priority Data

May 25, 2005 (DE) .................. 10 2005 024 599

(51) Int. Cl.
*A01N 43/56* (2006.01)
*C07D 231/10* (2006.01)
(52) U.S. Cl. ................ 504/280; 548/356.1; 548/373.1; 548/374.1; 504/261
(58) Field of Classification Search ............. 548/356.1, 548/373.1, 374.1; 504/261, 280
See application file for complete search history.

(56) References Cited

U.S. PATENT DOCUMENTS

| 4,904,674 | A | 2/1990 | Martin et al. |
| 5,346,907 | A | 9/1994 | Kerwin, Jr. et al. |
| 5,534,541 | A | 7/1996 | Drauz et al. |
| 6,399,770 | B1 | 6/2002 | Makeyama |
| 7,687,435 | B2 | 3/2010 | Witschel et al. |
| 2005/0085516 | A1 | 4/2005 | Rentzea et al. |
| 2005/0215435 | A1 | 9/2005 | Menges et al. |
| 2007/0060480 | A1 | 3/2007 | Witschel et al. |

FOREIGN PATENT DOCUMENTS

| CA | 2 548 354 | 7/2005 |
| CA | 2 548 442 | 7/2005 |
| EP | 0 450 355 | 8/1995 |
| ES | 2 021 557 | 11/1991 |
| JP | 63 301868 | 12/1988 |
| JP | 2 172956 | 7/1990 |
| JP | 3-184962 | 8/1991 |
| JP | 3 294253 | 12/1991 |
| JP | 10 101655 | 4/1998 |
| WO | WO 96/12499 | 5/1996 |
| WO | WO 02/069905 | 9/2002 |
| WO | WO 02/083111 | 10/2002 |
| WO | WO 03/066576 | 8/2003 |
| WO | WO 2005/061443 | 7/2005 |
| WO | WO 2005/061464 | 7/2005 |
| WO | WO 2005/085266 | 9/2005 |
| WO | WO 2006/029829 | 3/2006 |

OTHER PUBLICATIONS

Albrecht, M., et al., The Synthesis of Amino Acid Bridged Dicatechol Derivatives, Synthesis, 2001, p. 468-472, No. 3.
Arrault, A., et al., Structure and total synthesis of cyclodidemnamide B, a cycloheptapeptide from the ascidian *Didemnum molle*, Tetrahedron Letters, 2002, p. 4041-4044, vol. 43.
Bergmann, E. D., et al., The β-Phenylserine Series, Part I, J. Chem. Soc., 1951, p. 2673-2678.
Clark, J. E., et al., An Enzymatic Route to Florfenicol, Synthesis, 1991, p. 891-894.
Ewing, W., et al., Synthetic Studies of Didemnins. IV. Synthesis of the Macrocycle, Tetrahedron Letters, 1989, p. 3757-3760, vol. 30.
Guan, Y., et al., Synthesis of Compound Libraries Based on 3,4-Diaminocyclopentanol Scaffolds, Journal of Combinatorial Chemistry, 2000, p. 297-301, vol. 2.

(Continued)

*Primary Examiner*—Golam M Shameem
(74) *Attorney, Agent, or Firm*—Brinks Hofer Gilson & Lione

(57) ABSTRACT

The present invention relates to heteroaroyl-substituted serineamides of the formula I

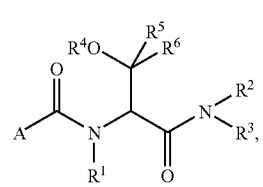

in which the variables A and $R^1$ to $R^6$ are as defined in the description,
and to their agriculturally useful salts,
to processes and intermediates for their preparation, and to the use of these compounds or of the compositions comprising these compounds for controlling unwanted plants.

9 Claims, No Drawings

OTHER PUBLICATIONS

Gupta, A., et al., Solution Conformation and Synthesis of a Linear Heptapeptide containing Two Dehydrophenylalanine Residues Separated by Three $_L$-Amino Acids, J. Chem. Soc. Perkin Trans. 2, 1990, p. 1911-1916.

Jursic, B. S., et al., Preparation of N-Acyl Derivatives of amino Acids from Acyl Chlorides and Amino Acids in the Presence of Cationic Surfactants. A Variation of the Schotten-Baumann Method of Benzoylation of Amino Acids, Synthetic Communications, 2001, p. 555-564, vol. 31(4).

Kawahata, N., et al., A single vessel protocol for the efficient formation of amide bonds from esters and lactones, Tetrahedron Letters, 2002, p. 7221-7223, vol. 43.

Lee, Y., et al., Efficient Solid-Phase Synthesis of Compounds Containing Phenylalanine and Its Derivatives via Side-Chain Attachment to the Polymer Support, J. Am. Chem., 1999, p. 8407-8408, vol. 121.

Martin, S. F., et al., Application of AlMe$_3$—Mediated Amidation Reactions to Solution Phase Peptide Synthesis, Tetrahedron Letters, 1998, p. 1517-1520, vol. 39.

Paulsen, H. et al., Synthese des Sauerstoffanalogons der Desferriform von $\delta_1$-Albomycin, Liebigs Ann. Chem., 1987, p. 565-575.

Perich, J., et al., The Synthesis of Multiple O-Phosphoseryl-Containing Peptides via Phenyl Phosphate Protection, J. Org. Chem., 1988, p. 4103-4105, vol. 53.

Pessoa-Mahana, H., et al., Synthesis of N-(Morpholinomethyl) Benzamides as Moclobemide Analogs, Synthetic Communications, 2002, p. 1437-1445, vol. 32.

Rousseau, J., et al., Synthesis of 3-Deaza-β-hydroxyhistidine Derivatives and Their Use for the Preparation of Substituted Pyrrolo [2,3-c]pyridine-5-carboxylates via the Pictet-Spengler Reaction, J. Org. Chem, 1998, p. 2731-2737, vol. 63.

Somlai, C., et al., Efficient, Racemization-Free Amidation of Protected Amino Acids, Synthesis, 1992, p. 285-287.

Takahashi, K., et al., Chemical Reactions by Polyethylene Glycol Modified Enzymes in Chlorinated Hydrocarbons, J. Org. chem . . . , 1985, p. 3414-3415, vol. 50.

Troast, D., et al., Studies Toward the Synthesis of (-)-Zampanolide: Preparation of N-Acyl Hemiaminal Model Systems, Organic Letters, 2002, p. 991-994, vol. 4.

Yadav, L., et al., Synthesis of chiral 3-acyl-4-alkylthiazolidine-2-thiones as enantioselective acylating agents, Indian Journal of Chemistry, 2002, p. 593-595, vol. 41B.

Yokokawa, F., et al., Synthetic studies of micropeptin T-20, a novel 3-amino-6-hydroxy-2-piperidone 9Ahp)-containing cyclic depsipeptide, Tetrahedron Letters, 2001, p. 5903-5908, vol. 42.

Zhdankin, V. V., et al., Synthesis and reactions of amino acid-derived benziodazole oxides: new chiral oxidizing reagents, Tetrahedron Letters, 2000, p. 5299-5302, vol. 41.

English language translation of the International Preliminary Report on Patentability from corresponding International Application No. PCT/EP2006/061128.

HETEROAROYL-SUBSTITUTED SERINEAMIDES

The present invention relates to heteroaroyl-substituted serineamides of formula I

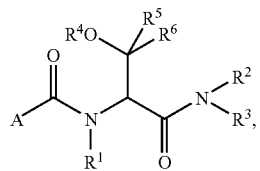

in which the variables are as defined below:

A is 5- or 6-membered heteroaryl having one to four nitrogen atoms, or one to three nitrogen atoms and one oxygen or sulfur atom, or one oxygen or sulfur atom, which heteroaryl may be partially or fully halogenated and/or may carry 1 to 3 radicals from the group consisting of cyano, $C_1$-$C_6$-alkyl, $C_3$-$C_6$-cycloalkyl, $C_1$-$C_6$-haloalkyl, $C_1$-$C_6$-alkoxy, $C_1$-$C_6$-haloalkoxy and $C_1$-$C_6$-alkoxy-$C_1$-$C_4$-alkyl;

$R^1$, $R^2$ are hydrogen, hydroxyl or $C_1$-$C_6$-alkoxy;

$R^3$ is $C_1$-$C_6$-alkyl, $C_1$-$C_4$-cyanoalkyl or $C_1$-$C_6$-haloalkyl;

$R^4$ is hydrogen, $C_1$-$C_6$-alkyl, $C_3$-$C_6$-cycloalkyl, $C_3$-$C_6$-alkenyl, $C_3$-$C_6$-alkynyl, $C_3$-$C_6$-haloalkenyl, $C_3$-$C_6$-haloalkynyl, formyl, $C_1$-$C_6$-alkylcarbonyl, $C_3$-$C_6$-cycloalkylcarbonyl, $C_2$-$C_6$-alkenylcarbonyl, $C_2$-$C_6$-alkynylcarbonyl, $C_1$-$C_6$-alkoxycarbonyl, $C_3$-$C_6$-alkenyloxycarbonyl, $C_3$-$C_6$-alkynyloxycarbonyl, $C_1$-$C_6$-alkylaminocarbonyl, $C_3$-$C_6$-alkenylaminocarbonyl, $C_3$-$C_6$-alkynylaminocarbonyl, $C_1$-$C_6$-alkylsulfonylaminocarbonyl, di-($C_1$-$C_6$-alkyl)aminocarbonyl, N—($C_3$-$C_6$-alkenyl)-N—($C_1$-$C_6$-alkyl)-aminocarbonyl, N—($C_3$-$C_6$-alkynyl)-N—($C_1$-$C_6$-alkyl)aminocarbonyl, N—($C_1$-$C_6$-alkoxy)-N—($C_1$-$C_6$-alkyl)aminocarbonyl, N—($C_3$-$C_6$-alkenyl)-N—($C_1$-$C_6$-alkoxy)-aminocarbonyl, N—($C_3$-$C_6$-alkynyl)-N—($C_1$-$C_6$-alkoxy)aminocarbonyl, di-($C_1$-$C_6$-alkyl)aminothiocarbonyl, ($C_1$-$C_6$-alkyl) cyanoimino, (amino)cyanoimino, [($C_1$-$C_6$-alkyl)amino]cyanoimino, [di($C_1$-$C_6$-alkyl)amino]cyanoimino, $C_1$-$C_6$-alkylcarbonyl-$C_1$-$C_6$-alkyl, $C_1$-$C_6$-alkoxyimino-$C_1$-$C_6$-alkyl, N—($C_1$-$C_6$-alkylamino)imino-$C_1$-$C_6$-alkyl, N-(di-$C_1$-$C_6$-alkylamino)imino-$C_1$-$C_6$-alkyl or tri-$C_1$-$C_4$-alkylsilyl, where the alkyl, cycloalkyl and alkoxy radicals mentioned may be partially or fully halogenated and/or may carry one to three of the following groups: cyano, hydroxyl, $C_3$-$C_6$-cycloalkyl, $C_1$-$C_6$-alkoxy-$C_1$-$C_4$-alkyl, $C_1$-$C_4$-alkoxy-$C_1$-$C_4$-alkoxy-$C_1$-$C_4$-alkyl, $C_1$-$C_4$-alkoxy, $C_1$-$C_4$-alkylthio, di-($C_1$-$C_4$-alkyl)amino, $C_1$-$C_4$-alkyl-$C_1$-$C_4$-alkoxycarbonylamino, $C_1$-$C_4$-alkylcarbonyl, hydroxycarbonyl, $C_1$-$C_4$-alkoxycarbonyl, aminocarbonyl, $C_1$-$C_4$-alkylaminocarbonyl, di-($C_1$-$C_4$-alkyl)aminocarbonyl or $C_1$-$C_4$-alkylcarbonyloxy;

phenyl, phenyl-$C_1$-$C_6$-alkyl, phenylcarbonyl, phenylcarbonyl-$C_1$-$C_6$-alkyl, phenoxycarbonyl, phenylaminocarbonyl, phenylsulfonylaminocarbonyl, N—($C_1$-$C_6$-alkyl)-N-(phenyl)aminocarbonyl, phenyl-$C_1$-$C_6$-alkylcarbonyl, where the phenyl radical may be partially or fully halogenated and/or may carry 1 to 3 of the following groups: nitro, cyano, $C_1$-$C_4$-alkyl, $C_1$-$C_4$-haloalkyl, $C_1$-$C_4$-alkoxy or $C_1$-$C_4$-haloalkoxy; or $SO_2R^7$;

$R^5$ is hydrogen or $C_1$-$C_6$-alkyl;

$R^6$ is $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_1$-$C_6$-cyanoalkyl, $C_2$-$C_6$-cyanoalkenyl, $C_2$-$C_6$-cyanoalkynyl, $C_1$-$C_6$-hydroxyalkyl, $C_2$-$C_6$-hydroxyalkenyl, $C_2$-$C_6$-hydroxyalkynyl, $C_3$-$C_6$-cycloalkyl, $C_3$-$C_6$-cycloalkenyl, 3- to 6-membered heterocyclyl, 3- to 6-membered heterocyclyl-$C_1$-$C_4$-alkyl, where the cycloalkyl, cycloalkenyl or 3- to 6-membered heterocyclyl radicals mentioned above may be partially or fully halogenated and/or may carry one to three radicals from the group consisting of oxo, cyano, nitro, $C_1$-$C_6$-alkyl, $C_1$-$C_6$-haloalkyl, hydroxyl, $C_1$-$C_6$-alkoxy, $C_1$-$C_6$-haloalkoxy, hydroxycarbonyl, $C_1$-$C_6$-alkoxycarbonyl, hydroxycarbonyl-$C_1$-$C_6$-alkoxy, $C_1$-$C_6$-alkoxycarbonyl-$C_1$-$C_6$-alkoxy, amino, $C_1$-$C_6$-alkylamino, di($C_1$-$C_6$-alkyl)amino, $C_1$-$C_6$-alkylsulfonylamino, $C_1$-$C_6$-haloalkylsulfonylamino, aminocarbonylamino, ($C_1$-$C_6$-alkylamino)carbonylamino, di($C_1$-$C_6$-alkyl)aminocarbonylamino, aryl and aryl($C_1$-$C_6$-alkyl);

$C_1$-$C_6$-alkoxy-$C_1$-$C_4$-alkyl, $C_2$-$C_6$-alkenyloxy-$C_1$-$C_4$-alkyl, $C_2$-$C_6$-alkynyloxy-$C_1$-$C_4$-alkyl, $C_1$-$C_6$-haloalkoxy-$C_1$-$C_4$-alkyl, $C_2$-$C_6$-haloalkenyloxy-$C_1$-$C_4$-alkyl, $C_2$-$C_6$-haloalkynyloxy-$C_1$-$C_4$-alkyl, $C_1$-$C_6$-alkoxy-$C_1$-$C_4$-alkoxy-$C_1$-$C_4$-alkyl, $C_1$-$C_6$-alkylthio-$C_1$-$C_4$-alkyl, $C_2$-$C_6$-alkenylthio-$C_1$-$C_4$-alkyl, $C_2$-$C_6$-alkynylthio-$C_1$-$C_4$-alkyl, $C_1$-$C_6$-haloalkyl-$C_1$-$C_4$-thioalkyl, $C_2$-$C_6$-haloalkenyl-$C_1$-$C_4$-thioalkyl, $C_2$-$C_6$-haloalkynyl-$C_1$-$C_4$-thioalkyl, $C_1$-$C_6$-alkylsulfinyl-$C_1$-$C_4$-alkyl, $C_1$-$C_6$-haloalkylsulfinyl-$C_1$-$C_4$-alkyl, $C_1$-$C_6$-alkylsulfonyl-$C_1$-$C_4$-alkyl, $C_1$-$C_6$-haloalkylsulfonyl-$C_1$-$C_4$-alkyl, amino-$C_1$-$C_4$-alkyl, $C_1$-$C_6$-alkylamino-$C_1$-$C_4$-alkyl, di($C_1$-$C_6$-alkyl)amino-$C_1$-$C_4$-alkyl, $C_1$-$C_6$-alkylsulfonylamino-$C_1$-$C_4$-alkyl, $C_1$-$C_6$-alkylsulfonyl-($C_1$-$C_6$-alkylamino)-$C_1$-$C_4$-alkyl, $C_1$-$C_6$-alkylcarbonyl, hydroxycarbonyl, $C_1$-$C_6$-alkoxycarbonyl, aminocarbonyl, $C_1$-$C_6$-alkylaminocarbonyl, di($C_1$-$C_6$-alkyl)aminocarbonyl, $C_1$-$C_6$-alkylcarbonyl-$C_1$-$C_6$-alkyl, hydroxycarbonyl-$C_1$-$C_4$-alkyl, $C_1$-$C_6$-alkoxycarbonyl-$C_1$-$C_4$-alkyl, $C_1$-$C_6$-haloalkoxycarbonyl-$C_1$-$C_4$-alkyl, $C_1$-$C_6$-alkylcarbonyloxy-$C_1$-$C_4$-alkyl, aminocarbonyl-$C_1$-$C_4$-alkyl, $C_1$-$C_6$-alkylaminocarbonyl-$C_1$-$C_4$-alkyl, di($C_1$-$C_6$-alkyl)aminocarbonyl-$C_1$-$C_4$-alkyl, $C_1$-$C_6$-alkylcarbonylamino-$C_1$-$C_4$-alkyl, formylamino-$C_1$-$C_4$-alkyl, $C_1$-$C_6$-alkoxycarbonylamino-$C_1$-$C_4$-alkyl, $C_1$-$C_6$-alkylcarbonyl-($C_1$-$C_6$-alkylamino)-$C_1$-$C_4$-alkyl, [($C_1$-$C_6$-alkyl)aminocarbonyloxy]-$C_1$-$C_4$-alkyl, [di($C_1$-$C_6$-alkyl)aminocarbonyloxy]$C_1$-$C_4$-alkyl, {di[di($C_1$-$C_6$-alkyl)amino]carbonyloxy}$C_1$-$C_4$-alkyl, [($C_1$-$C_6$-alkyl)aminocarbonylamino]$C_1$-$C_4$-alkyl, [di($C_1$-$C_6$-alkyl)aminocarbonylamino]-$C_1$-$C_4$-alkyl; phenyl-$C_1$-$C_4$-alkyl, phenyl-$C_2$-$C_4$-alkenyl, phenyl-$C_2$-$C_4$-alkynyl, phenyl-$C_1$-$C_4$-haloalkyl, phenyl-$C_2$-$C_4$-haloalkenyl, phenyl-$C_2$-$C_4$-haloalkynyl, phenyl-$C_1$-$C_4$-hydroxyalkyl, phenyl-$C_2$-$C_4$-hydroxyalkenyl, phenyl-$C_2$-$C_4$-hydroxyalkynyl, phenylcarbonyl-$C_1$-$C_4$-alkyl, phenylcarbonylamino-$C_1$-$C_4$-alkyl, phenylcarbonyloxy-$C_1$-$C_4$-alkyl, phenyloxycarbonyl-$C_1$-$C_4$-alkyl, phenyloxy-$C_1$-$C_4$-alkyl, phenylthio-$C_1$-$C_4$-alkyl, phenylsulfinyl-$C_1$-$C_4$-alkyl, phenylsulfonyl-$C_1$-$C_4$-alkyl, heteroaryl-$C_1$-$C_4$-alkyl, heteroaryl-$C_2$-$C_4$-alkenyl, heteroaryl-$C_2$-$C_4$-alkynyl, heteroaryl-$C_1$-$C_4$-haloalkyl, heteroaryl-$C_2$-$C_4$-haloalkenyl, heteroaryl-$C_2$-$C_4$-haloalkynyl, heteroaryl-$C_1$-$C_4$-hydroxyalkyl, heteroaryl-$C_2$-$C_4$-hydroxyalkenyl, heteroaryl-$C_2$-$C_4$-hydroxyalkynyl, heteroarylcarbonyl-$C_1$-$C_4$-alkyl, heteroarylcarbonyloxy-$C_1$-$C_4$-alkyl, heteroaryloxycarbonyl-$C_1$-$C_4$-alkyl, heteroaryloxy-$C_1$-$C_4$-alkyl, heteroarylthio-$C_1$-$C_4$-alkyl, heteroarylsulfinyl-$C_1$-$C_4$-alkyl, heteroarylsulfonyl-$C_1$-$C_4$-alkyl, where the phenyl and heteroaryl radicals mentioned above may be partially or fully halogenated and/or may carry one to three radicals from the group consisting of cyano, nitro, $C_1$-$C_6$-alkyl, $C_1$-$C_6$-haloalkyl, hydroxy, $C_1$-$C_6$-alkoxy, $C_1$-$C_6$-haloalkoxy, hydroxycarbonyl, $C_1$-$C_6$-alkoxycarbonyl, hydroxycarbonyl-$C_1$-$C_6$-alkoxy, $C_1$-$C_6$-alkoxycarbonyl-$C_1$-$C_6$-alkoxy, amino, $C_1$-$C_6$-alkylamino, di($C_1$-$C_6$-alkyl)amino, $C_1$-$C_6$-alkylsulfonylamino, $C_1$-$C_6$-haloalkylsulfonylamino, ($C_1$-$C_6$-alkylamino)carbonylamino, di($C_1$-$C_6$-alkyl)aminocarbonylamino, aryl and aryl($C_1$-$C_6$-alkyl);

$R^7$ is $C_1$-$C_6$-alkyl, $C_1$-$C_6$-haloalkyl or phenyl, where the phenyl radical may be partially or fully halogenated and/or may carry one to three of the following groups: $C_1$-$C_6$-alkyl, $C_1$-$C_6$-haloalkyl or $C_1$-$C_6$-alkoxy;

and their agriculturally useful salts.

Moreover, the invention relates to processes and intermediates for preparing compounds of the formula I, to compositions comprising them and to the use of these derivatives or of the compositions comprising them for controlling harmful plants.

Fungicidally effective thienyl-substituted amino acid derivatives which carry an optionally hydroxyl- or alkoxy-substituted alkyl radical in the α-position are described inter alia in EP 450 355.

Also known from the literature, for example from U.S. Pat. No. 5,346,907, WO 96/012499 and WO 02/069905, are serine derivatives having pharmaceutical activity which may carry in the α-position an optionally hydroxyl- or alkoxy-substituted alkyl radical, inter alia.

However, the herbicidal properties of the prior art compounds and/or their compatibility with crop plants are not entirely satisfactory.

Accordingly, it is an object of the present invention to provide novel, in particular herbicidally active, compounds having improved properties.

We have found that this object is achieved by the heteroaroyl-substituted serineamides of the formula I and their herbicidal action.

Furthermore, we have found herbicidal compositions which comprise the compounds I and have very good herbicidal action. Moreover, we have found processes for preparing these compositions and methods for controlling unwanted vegetation using the compounds I.

Depending on the substitution pattern, the compounds of the formula I comprise two or more centers of chirality, in which case they are present as enantiomers or diastereomer mixtures. The invention provides both the pure enantiomers or diastereomers and their mixtures.

The compounds of the formula I may also be present in the form of their agriculturally useful salts, the nature of the salt generally being immaterial. Suitable salts are, in general, the cations or the acid addition salts of those acids whose cations and anions, respectively, have no adverse effect on the herbicidal action of the compounds I.

Suitable cations are in particular the ions of the alkali metals, preferably lithium, sodium and potassium, of the alkaline earth metals, preferably calcium and magnesium, and of the transition metals, preferably manganese, copper, zinc and iron, and also ammonium, where, if desired, one to four hydrogen atoms may be replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, dimethylammonium, diisopropylammonium, tetramethylammonium, tetrabutylammonium, 2-(2-hydroxyeth-1-oxy)eth-1-yl-ammonium, di-(2-hydroxyeth-1-yl)ammonium, trimethylbenzylammonium, furthermore phosphonium ions, sulfonium ions, preferably tri($C_1$-$C_4$-alkyl)sulfonium, and sulfoxonium ions, preferably tri($C_1$-$C_4$alkyl)sulfoxonium.

Anions of useful acid addition salts are primarily chloride, bromide, fluoride, hydrogensulfate, sulfate, dihydrogenphosphate, hydrogenphosphate, nitrate, bicarbonate, carbonate, hexafluorosilicate, hexafluorophosphate, benzoate, and the anions of $C_1$-$C_4$-alkanoic acids, preferably formate, acetate, propionate and butyrate. The organic moieties mentioned for the substituents $R^1$-$R^6$ or as radicals on phenyl, aryl, heteroaryl or heterocyclyl rings are collective terms for individual enumerations of the specific group members. All hydrocarbon chains, i.e. all alkyl, alkylsilyl, alkenyl, alkynyl, cyanoalkyl, haloalkyl, haloalkenyl, haloalkynyl, alkoxy, haloalkoxy, alkoxyalkyl, alkoxyalkoxyalkyl, alkylcarbonyl, alkenylcarbonyl, alkynylcarbonyl, alkoxycarbonyl, alkenyloxycarbonyl, alkynyloxycarbonyl, alkylamino, alkylsulfonylamino, haloalkylsulfonylamino, alkylalkoxycarbonylamino, alkylaminocarbonyl, alkenylaminocarbonyl, alkynylaminocarbonyl, alkylsulfonylaminocarbonyl, dialkylaminocarbonyl, N-alkenyl-N-alkylaminocarbonyl, N-alkynyl-N-alkylamino-carbonyl, N-alkoxy-N-alkylaminocarbonyl, N-alkenyl-N-alkoxyaminocarbonyl, N-alkynyl-N-alkoxyaminocarbonyl, dialkylaminothiocarbonyl, alkylcarbonylalkyl, alkoximinoalkyl, N-(alkylamino)iminoalkyl, N-(dialkylamino)iminoalkyl, alkylcyanoimino, alkylaminocyanoimino, dialkylaminocyanoimino, formylaminoalkyl, alkoxycarbonylaminoalkyl, (alkylamino)carbonyloxyalkyl, (alkylamino)carbonylaminoalkyl, (dialkylamino)carbonylaminoalkyl, phenylcarbonylaminoalkyl, phenylalkyl, phenylcarbonylalkyl, N-alkyl-N-phenylaminocarbonyl, phenylalkylcarbonyl, arylalkyl, heterocyclylalkyl, heterocyclylcarbonylalkyl, N-alkyl-N-heterocyclylaminocarbonyl, heterocyclylalkylcarbonyl, alkylthio and alkylcarbonyloxy moieties may be straight-chain or branched.

Unless indicated otherwise, halogenated substituents preferably carry one to five identical or different halogen atoms. The term halogen denotes in each case fluorine, chlorine, bromine or iodine.

Examples of other meanings are:

$C_1$-$C_4$-alkyl and also the alkyl moieties of tri-$C_1$-$C_4$-alkylsilyl, $C_1$-$C_4$-alkylcarbonyloxy, $C_1$-$C_4$-alkyl-$C_1$-$C_4$-alkoxycarbonylamino, $C_1$-$C_6$-alkyliminooxy-$C_1$-$C_4$-alkyl, $C_1$-$C_4$-alkoxy-$C_1$-$C_4$-alkoxy-$C_1$-$C_4$-alkyl, $C_1$-$C_6$-alkoxy-$C_1$-$C_4$-alkyl, $C_2$-$C_6$-alkenyloxy-$C_1$-$C_4$-alkyl, $C_2$-$C_6$-alkynyloxy-$C_1$-$C_4$-alkyl, $C_1$-$C_6$-haloalkoxy-$C_1$-$C_4$-alkyl, $C_2$-$C_6$-haloalkenyloxy-$C_1$-$C_4$-alkyl, $C_2$-$C_6$-haloalkynyloxy-$C_1$-$C_4$-alkyl, $C_1$-$C_6$-alkoxy-$C_1$-$C_4$-alkoxy-$C_1$-$C_4$-alkyl, $C_1$-$C_6$-alkylthio-$C_1$-$C_4$-alkyl, $C_2$-$C_6$-alkenylthio-$C_1$-$C_4$-alkyl, $C_2$-$C_6$-alkynylthio-$C_1$-$C_4$-alkyl, $C_1$-$C_6$-alkylsulfinyl-$C_1$-$C_4$-alkyl, $C_1$-$C_6$-haloalkylsulfinyl-$C_1$-$C_4$-alkyl, $C_1$-$C_6$-alkylsulfonyl-$C_1$-$C_4$-alkyl, $C_1$-$C_6$-haloalkylsulfonyl-$C_1$-$C_4$-alkyl, amino-$C_1$-$C_4$-alkyl, $C_1$-$C_6$-alkylamino-$C_1$-$C_4$-alkyl, di($C_1$-$C_6$-alkyl)amino-$C_1$-$C_4$-alkyl, formylamino-$C_1$-$C_4$-alkyl, $C_1$-$C_6$-alkoxycarbonylamino-$C_1$-$C_4$-alkyl, $C_1$-$C_6$-alkylsulfonylamino-$C_1$-$C_4$-alkyl, $C_1$-$C_6$-alkylsulfonyl-($C_1$-$C_6$-alkylamino)-$C_1$-$C_4$-alkyl, hydroxylcarbonyl-$C_1$-$C_4$-alkyl, $C_1$-$C_6$-alkoxycarbonyl-$C_1$-$C_4$-alkyl, $C_1$-$C_6$-haloalkoxycarbonyl-$C_1$-$C_4$-alkyl, $C_1$-$C_6$-alkylcarbonyloxy-$C_1$-$C_4$-alkyl, aminocarbonyl-$C_1$-$C_4$-alkyl, $C_1$-$C_6$-alkylaminocarbonyl-$C_1$-$C_4$-alkyl, di($C_1$-$C_6$-alkyl)aminocarbonyl-$C_1$-$C_4$-alkyl, [($C_1$-$C_6$-alkyl)aminocarbonylamino]-$C_1$-$C_4$-alkyl, [di($C_1$-$C_6$-alkyl)aminocarbonylamino]-$C_1$-$C_4$-alkyl, $C_1$-$C_6$-alkylcarbonylamino-$C_1$-$C_4$-alkyl, $C_1$-$C_6$-alkylcarbonyl-($C_1$-$C_6$-alkylamino)-$C_1$-$C_4$-alkyl, [($C_1$-$C_6$-alkyl)aminocarbonyloxy]$C_1$-$C_4$-alkyl, [di($C_1$-$C_6$- alkyl)aminocarbonyloxy]$C_1$-$C_4$-alkyl, {di[di($C_1$-$C_6$-alkyl)amino]carbonyloxy}$C_1$-$C_4$-alkyl, heterocyclyl-$C_1$-$C_4$-alkyl, phenyl-$C_1$-$C_4$-alkyl, phenylcarbonylamino-$C_1$-$C_4$-alkyl, phenyl-$C_1$-$C_4$-alkyl, phenylcarbonyl-$C_1$-$C_4$-alkyl, heteroarylcarbonyl-$C_1$-$C_4$-alkyl, heteroarylcarbonyloxy-$C_1$-$C_4$-alkyl, heteroaryloxycarbonyl-$C_1$-$C_4$-alkyl, heteroaryloxy-$C_1$-$C_4$-alkyl, heteroarylthio-$C_1$-$C_4$-alkyl, heteroarylsulfinyl-$C_1$-$C_4$-alkyl, heteroarylsulfonyl-$C_1$-$C_4$-alkyl, and aryl-($C_1$-$C_4$-alkyl): for example methyl, ethyl, n-propyl, 1-methylethyl, n-butyl, 1-methylpropyl, 2-methylpropyl and 1,1-dimethylethyl;

$C_1$-$C_6$-alkyl and also the alkyl moieties of $C_1$-$C_6$-cyanoalkyl, $C_1$-$C_6$-alkoxycarbonyl-$C_1$-$C_6$-alkyl, $C_1$-$C_6$-alkylsulfonylamino, $C_1$-$C_6$-alkylsulfonylaminocarbonyl, N—($C_3$-$C_6$-alkenyl)-N—($C_1$-$C_6$-alkyl)aminocarbonyl, ($C_3$-$C_6$-alkynyl)-N—($C_1$-$C_6$-alkyl)aminocarbonyl, N—($C_1$-$C_6$-alkoxy)-N—($C_1$-$C_6$-alkyl)aminocarbonyl, $C_1$-$C_6$-alkylcarbonyl-$C_1$-$C_6$-alkyl, $C_1$-$C_6$-alkoxyimino-$C_1$-$C_6$-alkyl, N—($C_1$-$C_6$-alkylamino)imino-$C_1$-$C_6$-alkyl, N-(di-$C_1$-$C_6$-alkylamino)imino-$C_1$-$C_6$-alkyl, ($C_1$-$C_6$-alkyl)cyanoimino, phenyl-$C_1$-$C_6$-alkyl, phenylcarbonyl-$C_1$-$C_6$-alkyl, N—($C_1$-$C_6$-alkyl)-N-phenylaminocarbonyl, heterocyclyl-$C_1$-$C_6$-alkyl, heterocyclylcarbonyl-$C_1$-$C_6$-alkyl and N—($C_1$-$C_6$-alkyl)-N-heterocyclylaminocarbonyl:

$C_1$-$C_4$-alkyl as mentioned above, and also, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-di-methylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl and 1-ethyl-3-methylpropyl;

$C_1$-$C_4$-alkylcarbonyl: for example methylcarbonyl, ethylcarbonyl, propylcarbonyl, 1-methylethylcarbonyl, butylcarbonyl, 1-methylpropylcarbonyl, 2-methylpropylcarbonyl or 1,1-dimethylethylcarbonyl;

$C_1$-$C_6$-alkylcarbonyl and also the alkylcarbonyl radicals of $C_1$-$C_6$-alkylcarbonyl-$C_1$-$C_6$-alkyl, $C_1$-$C_6$-alkylcarbonyloxy-$C_1$-$C_6$-alkyl, $C_1$-$C_6$-alkylcarbonylamino-$C_1$-$C_4$-alkyl, phenyl-$C_1$-$C_6$-alkylcarbonyl and heterocyclyl-$C_1$-$C_6$-alkylcarbonyl, $C_1$-$C_6$-alkylcarbonyl-($C_1$-$C_6$-alkylamino)-$C_1$-$C_4$-alkyl:

$C_1$-$C_4$-alkylcarbonyl as mentioned above, and also, for example, pentylcarbonyl, 1-methylbutylcarbonyl, 2-methylbutylcarbonyl, 3-methylbutylcarbonyl, 2,2-dimethylpropylcarbonyl, 1-ethylpropylcarbonyl, hexylcarbonyl, 1,1-dimethylpropylcarbonyl, 1,2-dimethylpropylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl or 1-ethyl-2-methylpropylcarbonyl;

$C_3$-$C_6$-cycloalkyl and also the cycloalkyl moieties of $C_3$-$C_6$-cycloalkylcarbonyl: monocyclic saturated hydrocarbons having 3 to 6 ring members, such as cyclopropyl, cyclobutyl, cyclopentyl and cyclohexyl;

$C_3$-$C_6$-cycloalkenyl: for example 1-cyclopropenyl, 2-cyclopropenyl, 1-cyclobutenyl, 2-cyclobutenyl, 1-cyclopentenyl, 2-cyclopentenyl, 1,3-cyclopentadienyl, 1,4-cyclopentadienyl, 2,4-cyclopentadienyl, 1-cyclohexenyl, 2-cyclohexenyl, 3-cyclohexenyl, 1,3-cyclohexadienyl, 1,4-cyclohexadienyl, 2,5-cyclohexadienyl;

$C_3$-$C_6$-alkenyl and also the alkenyl moieties of $C_3$-$C_6$-alkenyloxycarbonyl, $C_3$-$C_6$-alkenylaminocarbonyl, N—($C_3$-$C_6$-alkenyl)-N—($C_1$-$C_6$-alkyl)aminocarbonyl and N-($C_3$-$C_6$-alkenyl)-N—($C_1$-$C_6$-alkoxy)aminocarbonyl: for example 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

$C_2$-$C_6$-alkenyl and also the alkenyl moieties of $C_2$-$C_6$-alkenylcarbonyl, $C_2$-$C_6$-alkenyloxy-$C_1$-$C_4$-alkyl, $C_2$-$C_6$-alkenylthio-$C_1$-$C_4$-alkyl, phenyl-$C_2$-$C_4$-alkenyl, heteroaryl-$C_2$-$C_4$-alkenyl: $C_3$-$C_6$-alkenyl as mentioned above, and also ethenyl;

$C_3$-$C_6$-alkynyl and also the alkynyl moieties of $C_3$-$C_6$-alkynyloxycarbonyl, $C_3$-$C_6$-alkynylaminocarbonyl, N—($C_3$-$C_6$-alkynyl)-N—($C_1$-$C_6$-alkyl)aminocarbonyl, N—($C_3$-$C_6$-alkynyl)-N—($C_1$-$C_6$-alkoxy)aminocarbonyl: for example 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

$C_2$-$C_6$-alkynyl and also the alkynyl moieties of $C_2$-$C_6$-alkynylcarbonyl, $C_2$-$C_2$-alkynyloxy-$C_1$-$C_4$-alkyl, $C_2$-$C_6$-alkynylthio-$C_1$-$C_4$-alkyl, phenyl-$C_2$-$C_4$-alkynyl, heteroaryl-$C_2$-$C_4$-alkynyl: $C_3$-$C_6$-alkynyl as mentioned above, and also ethynyl;

$C_1$-$C_4$-cyanoalkyl: for example cyanomethyl, 1-cyanoeth-1-yl, 2-cyanoeth-1-yl, 1-cyanoprop-1-yl, 2-cyanoprop-1-yl, 3-cyanoprop-1-yl, 1-cyanoprop-2-yl, 2-cyanoprop-2-yl, 1-cyanobut-1-yl, 2-cyanobut-1-yl, 3-cyanobut-1-yl, 4-cyanobut-1-yl, 1-cyanobut-2-yl, 2-cyanobut-2-yl, 1-cyanobut-3-yl, 2-cyanobut-3-yl, 1-cyano-2-methylprop-3-yl, 2-cyano-2-methylprop-3-yl, 3-cyano-2-methylprop-3-yl and 2-cyanomethylprop-2-yl;

$C_1$-$C_4$-hydroxyalkyl and also the $C_1$-$C_4$-hydroxyalkyl moieties of phenyl-$C_1$-$C_4$-hydroxyalkyl, heteroaryl-$C_1$-$C_4$-hydroxyalkyl: for example hydroxymethyl, 1-hydroxyeth-1-yl, 2-hydroxyeth-1-yl, 1-hydroxyprop-1-yl, 2-hydroxyprop-1-yl, 3-hydroxyprop-1-yl, 1-hydroxyprop-2-yl, 2-hydroxyprop-2-yl, 1-hydroxybut-1-yl, 2-hydroxybut-1-yl, 3-hydroxybut-1-yl, 4-hydroxybut-1-yl, 1-hydroxybut-2-yl, 2-hydroxybut-2-yl, 1-hydroxybut-3-yl, 2-hydroxybut-3-yl, 1-hydroxy-2-methylprop-3-yl, 2-hydroxy-2-methylprop-3-yl, 3-hydroxy-2-methylprop-3-yl and 2-hydroxymethylprop-2-yl, 1,2-dihydroxyethyl, 1,2-dihydroxyprop-3-yl, 2,3-dihydroxyprop-3-yl, 1,2-dihydroxyprop-2-yl, 1,2-dihydroxybut-4-yl, 2,3-dihydroxybut-4-yl, 3,4-dihydroxybut-4-yl, 1,2-dihydroxybut-2-yl, 1,2-dihydroxybut-3-yl, 2,3-dihydroxybut-3-yl, 1,2-dihydroxy-2-methylprop-3-yl, 2,3-dihydroxy-2-methylprop-3-yl;

$C_1$-$C_6$-hydroxyalkyl: $C_1$-$C_4$-hydroxyalkyl as stated above, and also for example 1-hydroxypent-5-yl, 2-hydroxypent-5-yl, 3-hydroxypent-5-yl, 4-hydroxypent-5-yl, 5-hydroxypent-5-yl, 1-hydroxypent-4-yl, 2-hydroxypent-4-yl, 3-hydroxypent-4-yl, 4-hydroxypent-4-yl, 1-hydroxypent-3-yl, 2-hydroxypent-3-yl, 3-hydroxypent-3-yl, 1-hydroxy-2-methylbut-3-yl, 2-hydroxy-2-methylbut-3-yl, 3-hydroxy-2-methylbut-3-yl, 1-hydroxy-2-methylbut-4-yl, 2-hydroxy-2-methylbut-4-yl, 3-hydroxy-2-methylbut-4-yl, 4-hydroxy-2-methylbut-4-yl, 1-hydroxy-3-methylbut-4-yl, 2-hydroxy-3-methylbut-4-yl, 3-hydroxy-3-methylbut-4-yl, 4-hydroxy-3-methylbut-4-yl, 1-hydroxyhex-6-yl, 2-hydroxyhex-6-yl, 3-hydroxyhex-6-yl, 4-hydroxyhex-6-yl, 5-hydroxyhex-6-yl, 6-hydroxyhex-6-yl, 1-hydroxy-2-methylpent-5-yl, 2-hydroxy-2-methylpent-5-yl, 3-hydroxy-2-methylpent-5-yl, 4-hydroxy-2-methylpent-5-yl, 5-hydroxy-2-methylpent-5-yl, 4-hydroxy-3-methylpent-5-yl, 2-hydroxy-3-methylpent-5-yl, 3-hydroxy-3-methylpent-5-yl, 4-hydroxy-3-methylpent-5-yl, 5-hydroxy-3-methylpent-5-yl, 1-hydroxy-4-methylpent-5-yl, 2-hydroxy-4-methylpent-5-yl, 3-hydroxy-4-methylpent-5-yl, 4-hydroxy-4-methylpent-5-yl, 5-hydroxy-4-methylpent-5-yl, 4-hydroxy-5-methylpent-5-yl, 2-hydroxy-5-methylpent-5-yl, 3-hydroxy-5-methylpent-5-yl, 4-hydroxy-5-methylpent-5-yl, 5-hydroxy-5-methylpent-5-yl, 1-hydroxy-2,3-dimethylbut-4-yl, 2-hydroxy-2,3-dimethylbut-4-yl, 3-hydroxy-2,3-dimethylbut-4-yl, 4-hydroxy-2,3-dimethylbut-4-yl, 1,2-dihydroxypent-5-yl, 2,3-dihydroxypent-5-yl, 3,4-dihydroxypent-5-yl, 4,5-dihydroxypent-5-yl, 1,2-dihydroxypent-4-yl, 2,3-dihydroxypent-4-yl, 3,4-dihydroxypent-4-yl, 4,5-dihydroxypent-4-yl, 1,2-dihydroxypent-3-yl, 2,3-dihydroxypent-3-yl, 1,2-dihydroxy-2-methylbut-3-yl, 2,3-dihydroxy-2-methylbut-3-yl, 3,4-dihydroxy-2-methylbut-3-yl, 2-hydroxy-2-hydroxymethylbut-3-yl, 1,2-dihydroxy-2-methylbut-4-yl, 2,3-dihydroxy-2-methylbut-4-yl, 3,4-dihydroxy-2-methylbut-4-yl, 1,2-dihydroxy-3-methylbut-4-yl, 2,3-dihydroxy-3-methylbut-4-yl, 3,4-dihydroxy-3-methylbut-4-yl, 3-hydroxy-3-hydroxymethylbut-4-yl, 1,2-dihydroxyhex-6-yl, 2,3-dihydroxyhex-6-yl, 3,4-dihydroxyhex-6-yl, 4,5-dihydroxyhex-6-yl, 5,6-dihydroxyhex-6-yl, 1,2-dihydroxy-2-methylpent-5-yl, 2,3-dihydroxy-2-methylpent-5-yl, 3,4-dihydroxy-2-methylpent-5-yl, 4,5-dihydroxy-2-methylpent-5-yl, 2-hydroxy-2-hydroxymethylpent-5-yl, 1,2-dihydroxy-3-methylpent-5-yl, 2,3-dihydroxy-3-methylpent-5-yl, 3,4-dihydroxy-3-methylpent-5-yl, 4,5-dihydroxy-3-methylpent-5-yl, 3-hydroxy-3-hydroxymethylpent-5-yl, 1,2-dihydroxy-4-methylpent-5-yl, 2,3-dihydroxy-4-methylpent-5-yl, 3,4-dihydroxy-4-methylpent-5-yl, 4,5-dihydroxy-4-methylpent-5-yl, 4-hydroxy-4-hydroxymethylpent-5-yl, 1,2-dihydroxy-5-methylpent-5-yl, 2,3-dihydroxy-5-methylpent-5-yl, 3,4-dihydroxy-5-methylpent-5-yl, 4,5-dihydroxy-5-methylpent-5-yl, 5-hydroxy-5-hydroxymethylpent-5-yl, 1,2-dihydroxy-2,3-dimethylbut-4-yl, 2,3-dihydroxy-2,3-dimethylbut-4-yl, 3,4-dihydroxy-2,3-dimethylbut-4-yl, 2-hydroxy-2-hydroxymethyl-3-methylbut-4-yl, 3-hydroxy-3-hydroxymethyl-2-methylbut-4-yl;

$C_1$-$C_4$-haloalkyl and also the haloalkyl moieties of phenyl-$C_1$-$C_4$-haloalkyl, heteroaryl-$C_1$-$C_4$-haloalkyl: a $C_1$-$C_4$-alkyl radical as mentioned above which is partially or fully substituted by fluorine, chlorine, bromine and/or iodine, i.e., for example, chloromethyl, dichloromethyl, trichloromethyl, fluoromethyl, difluoromethyl, trifluoromethyl, chlorofluoromethyl, dichlorofluoromethyl, chlorodifluoromethyl, bromomethyl, iodomethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, nonafluorobutyl, 1,1,2,2,-tetrafluoroethyl and 1-trifluoromethyl-1,2,2,2-tetrafluoroethyl;

$C_1$-$C_6$-haloalkyl and also the haloalkyl moieties of $C_1$-$C_6$-haloalkylsulfonylamino, $C_1$-$C_6$-haloalkyl-$C_1$-$C_4$-thioalkyl: $C_1$-$C_4$-haloalkyl as mentioned above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and dodecafluorohexyl;

$C_3$-$C_6$-haloalkenyl: a $C_3$-$C_6$-alkenyl radical as mentioned above which is partially or fully substituted by fluorine, chlorine, bromine and/or iodine, for example 2-chloroprop-2-en-1-yl, 3-chloroprop-2-en-1-yl, 2,3-dichloroprop-2-en-1-yl, 3,3-dichloroprop-2-en-1-yl, 2,3,3-trichloro-2-en-1-yl, 2,3-dichlorobut-2-en-1-yl, 2-bromoprop-2-en-1-yl, 3-bromoprop-2-en-1-yl, 2,3-dibromoprop-2-en-1-yl, 3,3-dibromoprop-2-en-1-yl, 2,3,3-tribromo-2-en-1-yl or 2,3-dibromobut-2-en-1-yl;

$C_2$-$C_6$-haloalkenyl and also the $C_2$-$C_6$-haloalkenyl moieties of $C_2$-$C_6$-haloalkenyloxy-$C_1$-$C_4$-alkyl, $C_2$-$C_6$-haloalkenyl-$C_1$-$C_4$-thioalkyl, phenyl-$C_2$-$C_4$-haloalkenyl, heteroaryl-$C_2$-$C_4$-haloalkenyl: a $C_2$-$C_6$-alkenyl radical as mentioned above which is partially or fully substituted by fluorine, chlorine, bromine and/or iodine, for example 2-chlorovinyl, 2-chloroallyl, 3-chloroallyl, 2,3-dichloroallyl, 3,3-dichloroallyl, 2,3,3-trichloroallyl, 2,3-dichlorobut-2-enyl, 2-bromovinyl, 2-bromoallyl, 3-bromoallyl, 2,3-dibromoallyl, 3,3-dibromoallyl, 2,3,3-tribromoallyl or 2,3-dibromobut-2-enyl;

$C_2$-$C_6$-cyanoalkenyl: for example 2-cyanovinyl, 2-cyanoallyl, 3-cyanoallyl, 2,3-dicyanoallyl, 3,3-dicyanoallyl, 2,3,3-tricyanoallyl, 2,3-dicyanobut-2-enyl;

$C_2$-$C_6$-hydroxyalkenyl and also the hydroxy moieties of phenyl-$C_1$-$C_4$-hydroxyalkenyl, heteroaryl-$C_1$-$C_4$-hydroxyalkenyl: for example 2-hydroxyvinyl, 2-hydroxyallyl, 3-hydroxyallyl, 2,3-dihydroxyallyl, 3,3-dihydroxyallyl, 2,3,3-trihydroxyallyl, 2,3-dihydroxybut-2-enyl;

$C_3$-$C_6$-haloalkynyl: a $C_3$-$C_6$-alkynyl radical as mentioned above which is partially or fully substituted by fluorine, chlorine, bromine and/or iodine, for example 1,1-difluoroprop-2-yn-1-yl, 3-iodoprop-2-yn-1-yl, 4-fluorobut-2-yn-1-yl, 4-chlorobut-2-yn-1-yl, 1,1-difluorobut-2-yn-1-yl, 4-iodobut-3-yn-1-yl, 5-fluoropent-3-yn-1-yl, 5-iodopent-4-yn-1-yl, 6-fluorohex-4-yn-1-yl or 6-iodohex-5-yn-1-yl;

$C_2$-$C_6$-haloalkynyl and also the $C_2$-$C_6$-haloalkynyl moieties of $C_2$-$C_6$-haloalkynyloxy-$C_1$-$C_4$-alkyl, $C_2$-$C_6$-haloalkynyl-$C_1$-$C_4$-thioalkyl, phenyl-$C_2$-$C_4$-haloalkynyl, heteroaryl-$C_2$-$C_4$-haloalkynyl: a $C_2$-$C_6$-alkynyl radical as mentioned above which is partially or fully substituted by fluorine, chlorine, bromine and/or iodine, for example 1,1-difluoroprop-2-yn-1-yl, 3-iodoprop-2-yn-1-yl, 4-fluorobut-2-yn-1-yl, 4-chlorobut-2-yn-1-yl, 1,1-difluorobut-2-yn-1-yl, 4-iodobut-3-yn-1-yl, 5-fluoropent-3-yn-1-yl, 5-iodopent-4-yn-1-yl, 6-fluorohex-4-yn-1-yl or 6-iodohex-5-yn-1-yl;

$C_2$-$C_6$-cyanoalkynyl: for example 1,1-dicyanoprop-2-yn-1-yl, 3-cyanoprop-2-yn-1-yl, 4-cyano-but-2-yn-1-yl, 1,1-dicyanobut-2-yn-1-yl, 4-cyanobut-3-yn-1-yl, 5-cyanopent-3-yn-1-yl, 5-cyanopent-4-yn-1-yl, 6-cyanohex-4-yn-1-yl or 6-cyanohex-5-yn-1-yl;

$C_2$-$C_6$-hydroxyalkynyl and also the hydroxy moieties of phenyl-$C_2$-$C_4$-hydroxyalkynyl: for example 1,1-dihydroxyprop-2-yn-1-yl, 3-hydroxyprop-2-yn-1-yl, 4-hydroxybut-2-yn-1-yl, 1,1-dihydroxybut-2-yn-1-yl, 4-hydroxybut-3-yn-1-yl, 5-hydroxypent-3-yn-1-yl, 5-hydroxypent-4-yn-1-yl, 6-hydroxyhex-4-yn-1-yl or 6-hydroxyhex-5-yn-1-yl;

$C_1$-$C_6$-alkylsulfinyl ($C_1$-$C_6$-alkyl-S(=O)—) and also the $C_1$-$C_6$-alkylsulfinyl moieties of $C_1$-$C_6$-alkylsulfinyl-$C_1$-$C_4$-alkyl: for example methylsulfinyl, ethylsulfinyl, propylsulfinyl, 1-methylethylsulfinyl, butylsulfinyl, 1-methylpropylsulfinyl, 2-methylpropylsulfinyl, 1,1-dimethylethylsulfinyl, pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, 1,1-dimethylpropylsulfinyl, 1,2-dimethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl and 1-ethyl-2-methylpropylsulfinyl;

$C_1$-$C_6$-haloalkylsulfinyl and also the $C_1$-$C_6$-haloalkylsulfinyl moieties of $C_1$-$C_6$-haloalkylsulfinyl-$C_1$-$C_4$-alkyl: $C_1$-$C_6$-alkylsulfinyl radical as mentioned above which is partially or fully substituted by fluorine, chlorine, bromine and/or iodine, i.e. for example fluoromethylsulfinyl, difluoromethylsulfinyl, trifluoromethylsulfinyl, chlorodifluoromethylsulfinyl, bromodifluoromethylsulfinyl, 2-fluoroethylsulfinyl, 2-chloroethylsulfinyl, 2-bromoethylsulfinyl, 2-iodoethylsulfinyl, 2,2-difluoroethylsulfinyl, 2,2,2-trifluoroethylsulfinyl, 2,2,2-trichloroethylsulfinyl, 2-chloro-2-fluoroethylsulfinyl, 2-chloro-2,2-difluoroethylsulfinyl, 2,2-dichloro-2-fluoroethylsulfinyl, pentafluoroethylsulfinyl, 2-fluoropropylsulfinyl, 3-fluoropropylsulfinyl, 2-chloropropylsulfinyl, 3-chloropropylsulfinyl, 2-bromopropylsulfinyl, 3-bromopropylsulfinyl, 2,2-difluoropropylsulfinyl, 2,3-difluoropropylsulfinyl, 2,3-dichloropropylsulfinyl, 3,3,3-trifluoropropylsulfinyl, 3,3,3-trichloropropylsulfinyl, 2,2,3,3,3-pentafluoropropylsulfinyl, heptafluoropropylsulfinyl, 1-(fluoromethyl)-2-fluoroethylsulfinyl, 1-(chloromethyl)-2-chloroethylsulfinyl, 1-(bromomethyl)-2-bromoethylsulfinyl, 4-fluorobutylsulfinyl, 4-chlorobutylsulfinyl, 4-bromobutylsulfinyl, nonafluorobutylsulfinyl, 5-fluoropentylsulfinyl, 5-chloropentylsulfinyl, 5-bromopentylsulfinyl, 5-iodopentylsulfinyl, undecafluoropentylsulfinyl, 6-fluorohexylsulfinyl, 6-chlorohexylsulfinyl, 6-bromohexylsulfinyl, 6-iodohexylsulfinyl and dodecafluorohexylsulfinyl;

$C_1$-$C_6$-alkylsulfonyl ($C_1$-$C_6$-alkyl-S(O)$_2$—) and also the $C_1$-$C_6$-alkylsulfonyl moieties of $C_1$-$C_6$-alkylsulfonyl-$C_1$-$C_4$-alkyl, $C_1$-$C_6$-alkylsulfonylamino, $C_1$-$C_6$-alkylsulfonylamino-$C_1$-$C_4$-alkyl, $C_1$-$C_6$-alkylsulfonyl-($C_1$-$C_6$-alkylamino)-$C_1$-$C_4$-alkyl: for example methylsulfonyl, ethylsulfonyl, propylsulfonyl, 1-methylethylsulfonyl, butylsulfonyl, 1-methylpropylsulfonyl, 2-methylpropylsulfonyl, 1,1-dimethylethylsulfonyl, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl and 1-ethyl-2-methylpropylsulfonyl;

$C_1$-$C_6$-haloalkylsulfonyl and also the $C_1$-$C_6$-haloalkylsulfonyl moieties of $C_1$-$C_6$-haloalkylsulfonyl-$C_1$-$C_4$-alkyl, $C_1$-$C_6$-haloalkylsulfonylamino: a $C_1$-$C_6$-alkylsulfonyl radical as mentioned above which is partially or fully substituted by fluorine, chlorine, bromine and/or iodine, i.e. for example fluoromethylsulfonyl, difluoromethylsulfonyl, trifluoromethylsulfonyl, chlorodifluoromethylsulfonyl, bromodifluoromethylsulfonyl, 2-fluoroethylsulfonyl, 2-chloroethylsulfonyl, 2-bromoethylsulfonyl, 2-iodoethylsulfonyl, 2,2-difluoroethyl-sulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2,2,2-trichloroethylsulfonyl, pentafluoroethylsulfonyl, 2-fluoropropylsulfonyl, 3-fluoropropylsulfonyl, 2-chloropropylsulfonyl, 3-chloropropylsulfonyl, 2-bromopropylsulfonyl, 3-bromopropylsulfonyl, 2,2-difluoropropylsulfonyl, 2,3-difluoropropylsulfonyl, 2,3-dichloropropylsulfonyl, 3,3,3-trifluoropropylsulfonyl, 3,3,3-trichloropropylsulfonyl, 2,2,3,3,3-pentafluoropropylsulfonyl, heptafluoropropylsulfonyl, 1-(fluoromethyl)-2-fluoroethylsulfonyl, 1-(chloromethyl)-2-chloroethylsulfonyl, 1-(bromomethyl)-2-bromoethylsulfonyl, 4-fluorobutylsulfonyl, 4-chlorobutylsulfonyl, 4-bromobutylsulfonyl, nonafluorobutylsulfonyl, 5-fluoropentylsulfonyl, 5-chloropentylsulfonyl, 5-bromopentylsulfonyl, 5-iodopentylsulfonyl, 6-fluorohexylsulfonyl, 6-bromohexylsulfonyl, 6-iodohexylsulfonyl and dodecafluorohexylsulfonyl;

$C_1$-$C_4$-alkoxy and also the alkoxy moieties of hydroxycarbonyl-$C_1$-$C_4$-alkoxy, $C_1$-$C_4$-alkoxycarbonyl-$C_1$-$C_4$-alkoxy, $C_1$-$C_4$-alkoxy-$C_1$-$C_4$-alkoxy-$C_1$-$C_4$-alkyl and $C_1$-$C_4$-alkyl-$C_1$-$C_4$-alkoxycarbonylamino: for example methoxy, ethoxy, propoxy, 1-methylethoxy, butoxy, 1-methylpropoxy, 2-methylpropoxy and 1,1-dimethylethoxy;

$C_1$-$C_6$-alkoxy and also the alkoxy moieties of hydroxycarbonyl-$C_1$-$C_6$-alkoxy, $C_1$-$C_6$-alkoxycarbonyl-$C_1$-$C_6$-alkoxy, N—($C_1$-$C_6$-alkoxy)-N—($C_1$-$C_6$-alkyl)aminocarbonyl, N—($C_3$-$C_6$-alkenyl)-N—($C_1$-$C_6$-alkoxy)aminocarbonyl, N—($C_3$-$C_6$-alkynyl)-N—($C_1$-$C_6$-alkoxy)aminocarbonyl and $C_1$-$C_6$-alkoxyimino-$C_1$-$C_6$-alkyl: $C_1$-$C_4$-alkoxy as mentioned above, and also, for example, pentoxy, 1-methylbutoxy, 2-methylbutoxy, 3-methoxylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

$C_1$-$C_4$-haloalkoxy: a $C_1$-$C_4$-alkoxy radical as mentioned above which is partially or fully substituted by fluorine, chlorine, bromine and/or iodine, i.e., for example, fluoromethoxy, difluoromethoxy, trifluoromethoxy, chlorodifluoromethoxy, bromodifluoromethoxy, 2-fluoroethoxy, 2-chloroethoxy, 2-bromomethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy and nonafluorobutoxy;

$C_1$-$C_6$-haloalkoxy and also the $C_1$-$C_6$-haloalkoxy moieties of $C_1$-$C_6$-haloalkoxy-$C_1$-$C_4$-alkyl, $C_1$-$C_6$-haloalkoxycarbonyl-$C_1$-$C_4$-alkyl: $C_1$-$C_4$-haloalkoxy as mentioned above, and also, for example, 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy and dodecafluorohexoxy;

$C_1$-$C_6$-alkoxy-$C_1$-$C_4$-alkyl and also the $C_1$-$C_6$-alkoxy-$C_1$-$C_4$-alkyl moieties of $C_1$-$C_6$-alkoxy-$C_1$-$C_4$-alkoxy-$C_1$-$C_4$-alkyl: $C_1$-$C_4$-alkyl which is substituted by $C_1$-$C_6$-alkoxy as mentioned above, i.e., for example, methoxymethyl, ethoxymethyl, propoxymethyl, (1-methylethoxy)methyl, butoxymethyl, (1-methylpropoxy)methyl, (2-methylpropoxy)methyl, (1,1-dimethylethoxy)methyl, 2-(methoxy)ethyl, 2-(ethoxy)ethyl, 2-(propoxy)ethyl, 2-(1-methylethoxy)ethyl, 2-(butoxy)ethyl, 2-(1-methylpropoxy)ethyl, 2-(2-methylpropoxy) ethyl, 2-(1,1-dimethylethoxy)ethyl, 2-(methoxy)propyl, 2-(ethoxy)propyl, 2-(propoxy)propyl, 2-(1-methylethoxy)propyl, 2-(butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(propoxy)propyl, 3-(1-methylethoxy)-propyl, 3-(butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(propoxy)butyl, 2-(1-methylethoxy)butyl, 2-(butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(propoxy)butyl, 3-(1-methylethoxy)butyl, 3-(butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(propoxy)butyl, 4-(1-methylethoxy)butyl, 4-(butoxy)butyl, 4-(1-methylpropoxy)butyl, 4-(2-methylpropoxy)butyl and 4-(1,1-dimethylethoxy)butyl;

$C_1$-$C_4$-alkoxycarbonyl and also the alkoxycarbonyl moieties of $C_1$-$C_4$-alkoxycarbonyl-$C_1$-$C_4$-alkoxy, $C_1$-$C_4$-alkoxy-$C_1$-$C_4$-alkoxycarbonyl and di-($C_1$-$C_4$-alkyl)amino-$C_1$-$C_4$-alkoxycarbonyl: for example methoxycarbonyl, ethoxycarbonyl, propoxycarbonyl, 1-methylethoxycarbonyl, butoxycarbonyl, 1-methylpropoxycarbonyl, 2-methylpropoxycarbonyl or 1,1-dimethylethoxycarbonyl;

$C_1$-$C_6$-alkoxycarbonyl and also the alkoxycarbonyl moieties of $C_1$-$C_6$-alkoxycarbonyl-$C_1$-$C_6$-alkoxy and $C_1$-$C_6$-alkoxycarbonylamino-$C_1$-$C_4$-alkyl: $C_1$-$C_4$-alkoxycarbonyl as mentioned above, and also, for example, pentoxycarbonyl, 1-methylbutoxycarbonyl, 2-methylbutoxycarbonyl, 3-methylbutoxycarbonyl, 2,2-dimethylpropoxycarbonyl, 1-ethylpropoxycarbonyl, hexoxycarbonyl, 1,1-dimethylpropoxycarbonyl, 1,2-dimethylpropoxycarbonyl, 1-methylpentoxycarbonyl, 2-methylpentoxycarbonyl, 3-methylpentoxycarbonyl, 4-methylpentoxycarbonyl, 1,1-dimethylbutoxycarbonyl, 1,2-dimethylbutoxycarbonyl, 1,3-dimethylbutoxycarbonyl, 2,2-dimethylbutoxycarbonyl, 2,3-dimethylbutoxycarbonyl, 3,3-dimethylbutoxycarbonyl, 1-ethylbutoxycarbonyl, 2-ethylbutoxycarbonyl, 1,1,2-trimethylpropoxycarbonyl, 1,2,2-trimethylpropoxycarbonyl, 1-ethyl-1-methylpropoxycarbonyl or 1-ethyl-2-methylpropoxycarbonyl;

$C_1$-$C_4$-alkylthio and also the $C_1$-$C_4$-alkylthio moieties of $C_1$-$C_6$-haloalkyl-$C_1$-$C_4$-thioalkyl, $C_2$-$C_6$-haloalkenyl-$C_1$-$C_4$-thioalkyl, $C_2$-$C_6$-haloalkynyl-$C_1$-$C_4$-thioalkyl: for example methylthio, ethylthio, propylthio, 1-methylethylthio, butylthio, 1-methylpropylthio, 2-methylpropylthio and 1,1-dimethylethylthio;

$C_1$-$C_6$-alkylthio and also the $C_1$-$C_6$-alkylthio moieties of $C_1$-$C_6$-alkylthio-$C_1$-$C_4$-alkyl: $C_1$-$C_4$-alkylthio as mentioned above, and also, for example, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-cimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

$C_1$-$C_6$-alkylamino and also the $C_1$-$C_6$-alkylamino radicals of N—($C_1$-$C_6$-alkylamino)imino-$C_1$-$C_6$-alkyl, $C_1$-$C_6$-alkylamino-$C_1$-$C_4$-alkyl, $C_1$-$C_6$-alkylsulfonyl-($C_1$-$C_6$- alkylamino)-$C_1$-$C_4$-alkyl, $C_1$-$C_6$-alkylcarbonyl-($C_1$-$C_6$-alkylamino)-$C_1$-$C_4$-alkyl and [($C_1$-$C_6$-alkyl)amino-cyanoimino: for example methylamino, ethylamino, propylamino, 1-methylethylamino, butylamino, 1-methylpropylamino, 2-methylpropylamino, 1,1-dimethylethylamino, pentylamino, 1-methylbutylamino, 2-methylbutylamino, 3-methylbutylamino, 2,2-dimethylpropylamino, 1-ethylpropylamino, hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutylamino, 3,3-dimethylbutylamino, 1-ethylbutylamino, 2-ethylbutylamino, 1,1,2-trimethylpropylamino, 1,2,2-trimethylpropylamino, 1-ethyl-1-methylpropylamino or 1-ethyl-2-methylpropylamino;

di-($C_1$-$C_4$-alkyl)amino: for example N,N-dimethylamino, N,N-diethylamino, N,N-dipropylamino, N,N-di-(1-methylethyl)amino, N,N-dibutylamino, N,N-di-(1-methylpropyl)amino, N,N-di-(2-methylpropyl)amino, N,N-di-(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino and N-(1,1-dimethylethyl)-N-(2-methylpropyl)amino;

di($C_1$-$C_6$-alkyl)amino and also the dialkylamino radicals of N-(di-$C_1$-$C_6$-alkylamino)imino-$C_1$-$C_6$-alkyl, di($C_1$-$C_6$-alkyl)amino-$C_1$-$C_4$-alkyl, [di($C_1$-$C_6$-alkyl)aminocabonyloxy]-$C_1$-$C_4$-alkyl, {di[di($C_1$-$C_6$-alkyl)amino]cabonyloxy}-$C_1$-$C_4$-alkyl and [di($C_1$-$C_6$-alkyl)amino] cyanoimino: di($C_1$-$C_4$-alkyl)amino as mentioned above, and also, for example, N,N-dipentylamino, N,N-dihexylamino, N-methyl-N-pentylamino, N-ethyl-N-pentylamino, N-methyl-N-hexylamino and N-ethyl-N-hexylamino; ($C_1$-$C_4$-alkylamino)carbonyl: for example methylaminocarbonyl, ethylaminocarbonyl, propylaminocarbonyl, 1-methylethylaminocarbonyl, butylaminocarbonyl, 1-methylpropylaminocarbonyl, 2-methylpropylaminocarbonyl or 1,1-dimethylethylaminocarbonyl;

($C_1$-$C_4$-alkylamino)carbonyl and also the ($C_1$-$C_4$-alkylamino)carbonyl moieties of ($C_1$-$C_4$-alkylamino)carbonylamino: for example methylaminocarbonyl, ethylaminocarbonyl, propylaminocarbonyl, 1-methylethylaminocarbonyl, butylaminocarbonyl, 1-methylpropylaminocarbonyl, 2-methylpropylaminocarbonyl or 1,1-dimethylethylaminocarbonyl;

di($C_1$-$C_4$-alkyl)aminocarbonyl and also the di($C_1$-$C_4$-alkyl)aminocarbonyl moieties of di($C_1$-$C_4$-alkyl)aminocarbonylamino: for example N,N-dimethylaminocarbonyl, N,N-diethylaminocarbonyl, N,N-di-(1-methylethyl)aminocarbonyl, N,N-dipropylaminocarbonyl, N N-dibutylaminocarbonyl, N,N-di-(1-methylpropyl)aminocarbonyl, N,N-di-(2-methylpropyl)aminocarbonyl, N,N-di-(1,1-dimethylethyl)aminocarbonyl, N-ethyl-N-methylaminocarbonyl, N-methyl-N-propylaminocarbonyl, N-methyl-N-(1-methylethyl)aminocarbonyl, N-butyl-N-methylaminocarbonyl, N-methyl-N-(1-methylpropyl) aminocarbonyl, N-methyl-N-(2-methylpropyl) aminocarbonyl, N-(1,1-dimethylethyl)-N-methylaminocarbonyl, N-ethyl-N-propylaminocarbonyl, N-ethyl-N-(1-methylethyl) aminocarbonyl, N-butyl-N-ethylaminocarbonyl, N-ethyl-N-(1-methylpropyl)aminocarbonyl, N-ethyl-N-(2-methylpropyl)aminocarbonyl, N-ethyl-N-(1,1-dimethylethyl)aminocarbonyl, N-(1-methylethyl)-N-propylaminocarbonyl, N-butyl-N-propylaminocarbonyl, N-(1-methylpropyl)-N-propylaminocarbonyl, N-(2-methylpropyl)-N-propylaminocarbonyl, N-(1,1-dimethylethyl)N-propylaminocarbonyl, N-butyl-N-(1-methylethyl) aminocarbonyl, N-(1-methylethyl)-N-(1-methylpropyl) aminocarbonyl, N-(1-methylethyl)-N-(2-methylpropyl) aminocarbonyl, N-(1,1-dimethylethyl)-N-(1-methylethyl)aminocarbonyl, N-butyl-N-(1-methylpropyl)aminocarbonyl, N-butyl-N-(2-methylpropyl)aminocarbonyl, N-butyl-N-(1,1-dimethylethyl)aminocarbonyl, N-(1-methylpropyl)-N-(2-methylpropyl)aminocarbonyl, N-(1,1-dimethylethyl)-N-(1-methylpropyl)aminocarbonyl or N-(1,1-dimethylethyl)-N-(2-methylpropyl)aminocarbonyl;

($C_1$-$C_6$-alkylamino)carbonyl and also the ($C_1$-$C_6$-alkylamino)carbonyl moieties of ($C_1$-$C_6$-alkylamino)carbonylamino, ($C_1$-$C_6$-alkylamino)carbonyloxy-$C_1$-$C_4$-alkyl, $C_1$-$C_6$-alkylaminocarbonyl-$C_1$-$C_4$-alkyl and [($C_1$-$C_6$-alkyl)aminocarbonylamino]-$C_1$-$C_4$-alkyl: ($C_1$-$C_4$-alkylamino)carbonyl as mentioned above, and also, for example, pentylaminocarbonyl, 1-methylbutylaminocarbonyl, 2-methylbutylaminocarbonyl, 3-methylbutylaminocarbonyl, 2,2-dimethylpropylaminocarbonyl, 1-ethylpropylaminocarbonyl, hexylaminocarbonyl, 1,1-dimethylpropylaminocarbonyl, 1,2-dimethylpropylaminocarbonyl, 1-methylpentylaminocarbonyl, 2-methylpentylaminocarbonyl, 3-methylpentylaminocarbonyl, 4-methylpentylaminocarbonyl, 1,1-dimethylbutylaminocarbonyl, 1,2-dimethylbutylaminocarbonyl, 1,3-dimethylbutylaminocarbonyl, 2,2-dimethylbutylaminocarbonyl, 2,3-dimethylbutylaminocarbonyl, 3,3-dimethylbutylaminocarbonyl, 1-ethylbutylaminocarbonyl, 2-ethylbutylaminocarbonyl, 1,1,2-trimethylpropylaminocarbonyl, 1,2,2-trimethylpropylaminocarbonyl, 1-ethyl-1-methylpropylaminocarbonyl or 1-ethyl-2-methylpropylaminocarbonyl;

di($C_1$-$C_6$-alkyl)aminocarbonyl and also the di($C_1$-$C_6$-alkyl)aminocarbonyl moieties of di($C_1$-$C_6$-alkyl)aminocarbonylamino, di($C_1$-$C_6$-alkyl)aminocarbonyl-$C_1$-$C_4$-alkyl and [di($C_1$-$C_6$-alkyl)aminocarbonylamino]-$C_1$-$C_4$-alkyl: di($C_1$-$C_4$-alkyl)aminocarbonyl as mentioned above, and also, for example, N-methyl-N-pentylaminocarbonyl, N-methyl-N-(1-methylbutyl) aminocarbonyl, N-methyl-N-(2-methylbutyl)aminocarbonyl, N-methyl-N-(3-methylbutyl)aminocarbonyl, N-methyl-N-(2,2-dimethylpropyl)aminocarbonyl, N-methyl-N-(1-ethylpropyl)aminocarbonyl, N-methyl-N-hexylaminocarbonyl, N-methyl-N-(1,1-dimethylpropyl)aminocarbonyl, N-methyl-N-(1,2-dimethylpropyl)aminocarbonyl, N-methyl-N-(1-methylpentyl)aminocarbonyl, N-methyl-N-(2-methylpentyl)aminocarbonyl, N-methyl-N-(3-methylpentyl)aminocarbonyl, N-methyl-N-(4-methylpentyl)aminocarbonyl, N-methyl-N-(1,1-dimethylbutyl)aminocarbonyl, N-methyl-N-(1,2-dimethylbutyl)aminocarbonyl, N-methyl-N-(1,3-dimethylbutyl)aminocarbonyl, N-methyl-N-(2,2-dimethylbutyl)aminocarbonyl, N-methyl-N-(2,3-dimethylbutyl)aminocarbonyl, N-methyl-N-(3,3-dimethylbutyl)aminocarbonyl, N-methyl-N-(1-ethylbutyl)aminocarbonyl, N-methyl-N-(2-ethylbutyl)aminocarbonyl, N-methyl-N-(1,1,2-trimethylpropyl)aminocarbonyl, N-methyl-N-(1,2,2-trimethylpropyl)aminocarbonyl, N-methyl-N-(1-ethyl-1-methylpropyl)aminocarbonyl, N-methyl-N-(1-ethyl-2-methylpropyl)aminocarbonyl, N-ethyl-N-pentylaminocarbonyl, N-ethyl-N-(1-methylbutyl)aminocarbonyl, N-ethyl-N-(2-methylbutyl)aminocarbonyl, N-ethyl-N-(3-methylbutyl)aminocarbonyl, N-ethyl-N-(2,2-dimethylpropyl)aminocarbonyl, N-ethyl-N-(1-ethylpropyl)aminocarbonyl, N-ethyl-N-hexylaminocarbonyl, N-ethyl-N-(1,1-dimethylpropyl)aminocarbonyl, N-ethyl-N-(1,2-dimethylpropyl)aminocarbonyl, N-ethyl-N-(1-methylpentyl)aminocarbonyl, N-ethyl-N-(2-methylpentyl)aminocarbonyl, N-ethyl-N-(3-methylpentyl)aminocarbonyl, N-ethyl-N-(4-methylpentyl)aminocarbonyl, N-ethyl-N-(1,1-dimethylbutyl)aminocarbonyl, N-ethyl-N-(1,2-dimethylbutyl)aminocarbonyl, N-ethyl-N-(1,3-dimethylbutyl)aminocarbonyl, N-ethyl-N-(2,2-dimethylbutyl)aminocarbonyl, N-ethyl-N-(2,3-dimethylbutyl)aminocarbonyl, N-ethyl-N-(3,3-dimethylbutyl)aminocarbonyl, N-ethyl-N-(1-ethylbutyl)aminocarbonyl, N-ethyl-N-(2-ethylbutyl)aminocarbonyl, N-ethyl-N-(1,1,2-trimethylpropyl)aminocarbonyl, N-ethyl-N-(1,2,2-trimethylpropyl)aminocarbonyl, N-ethyl-N-(1-ethyl-1-methylpropyl)aminocarbonyl, N-ethyl-N-(1-ethyl-2-methylpropyl)aminocarbonyl, N-propyl-N-pentylaminocarbonyl, N-butyl-N-pentylaminocarbonyl, N,N-dipentylaminocarbonyl, N-propyl-N-hexylaminocarbonyl, N-butyl-N-hexylaminocarbonyl, N-pentyl-N-hexylaminocarbonyl or N,N-dihexylaminocarbonyl;

di($C_1$-$C_6$-alkyl)aminothiocarbonyl: for example N,N-dimethylaminothiocarbonyl, N,N-diethylaminothiocarbonyl, N,N-di-(1-methylethyl)aminothiocarbonyl, N,N-dipropylaminothiocarbonyl, N,N-dibutylaminothiocarbonyl, N,N-di-(1-methylpropyl)aminothiocarbonyl, N,N-di-(2-methylpropyl)aminothiocarbonyl, N,N-di-(1,1-dimethylethyl)aminothiocarbonyl, N-ethyl-N-methylaminothiocarbonyl, N-methyl-N-propylaminothiocarbonyl, N-methyl-N-(1-methylethyl)aminothiocarbonyl, N-butyl-N-methylaminothiocarbonyl, N-methyl-N-(1-methylpropyl)aminothiocarbonyl, N-methyl-N-(2-methylpropyl)aminothiocarbonyl, N-(1,1-dimethylethyl)-N-methylaminothiocarbonyl, N-ethyl-N-propylaminothiocarbonyl, N-ethyl-N-(1-methylethyl)aminothiocarbonyl, N-butyl-N-ethylaminothiocarbonyl, N-ethyl-N-(1-methylpropyl)aminothiocarbonyl, N-ethyl-N-(2-methylpropyl)aminothiocarbonyl, N-ethyl-N-(1,1-dimethylethyl)aminothiocarbonyl, N-(1-methylethyl)-N-propylaminothiocarbonyl, N-butyl-N-propylaminothiocarbonyl, N-(1-methylpropyl)-N-propylaminothiocarbonyl, N-(2-methylpropyl)-N-propylamino-thiocarbonyl, N-(1,1-dimethylethyl)-N-propylaminothiocarbonyl, N-butyl-N-(1-methylethyl)aminothiocarbonyl, N-(1-methylethyl)-N-(1-methylpropyl)aminothiocarbonyl, N-(1-methylethyl)-N-(2-methylpropyl)aminothiocarbonyl, N-(1,1-dimethylethyl)-N-(1-methylethyl)aminothiocarbonyl, N-butyl-N-(1-methylpropyl)aminothiocarbonyl, N-butyl-N-(2-methylpropyl)aminothiocarbonyl, N-butyl-N-(1,1-dimethylethyl)aminothiocarbonyl, N-(1-methylpropyl)-N-(2-methylpropyl)aminothiocarbonyl, N-(1,1-dimethylethyl)-N-(1-methylpropyl)aminothiocarbonyl, N-(1,1-dimethylethyl)-N-(2-methylpropyl)aminothiocarbonyl, N-methyl-N-pentylaminothiocarbonyl, N-methyl-N-(1-methylbutyl)aminothiocarbonyl, N-methyl-N-(2-methylbutyl)aminothiocarbonyl, N-methyl-N-(3-methylbutyl)aminothiocarbonyl, N-methyl-N-(2,2-dimethylpropyl)aminothiocarbonyl, N-methyl-N-(1-ethylpropyl)aminothiocarbonyl, N-methyl-N-hexylaminothiocarbonyl, N-methyl-N-(1,1-dimethylpropyl)aminothiocarbonyl, N-methyl-N-(1,2-dimethylpropyl)aminothiocarbonyl, N-methyl-N-(1-methylpentyl)aminothiocarbonyl, N-methyl-N-(2-methylpentyl)aminothiocarbonyl, N-methyl-N-(3-methylpentyl)aminothiocarbonyl, N-methyl-N-(4-methylpentyl)aminothiocarbonyl, N-methyl-N-(1,1-dimethylbutyl)aminothiocarbonyl, N-methyl-N-(1,2-dimethylbutyl)aminothiocarbonyl, N-methyl-N-(1,3-dimethylbutyl)aminothiocarbonyl, N-methyl-N-(2,2-dimethylbutyl)aminothiocarbonyl, N-methyl-N-(2,3-dimethylbutyl)aminothiocarbonyl, N-methyl-N-(3,3-dimethylbutyl)aminothiocarbonyl, N-methyl-N-(1-ethylbutyl)aminothiocarbonyl, N-methyl-N-(2-ethylbutyl)aminothiocarbonyl, N-methyl-N-ethyl-N-(1,1,2-trimethylpropyl)aminothiocarbonyl, N-methyl-N-(1,2,2-trimethylpropyl)aminothiocarbonyl, N-methyl-N-(1-ethyl-1-methylpropyl)aminothiocarbonyl, N-methyl-N-(1-ethyl-2-methylpropyl)aminothiocarbonyl, N-ethyl-N-pentylaminothiocarbonyl, N-ethyl-N-(1-methylbutyl)aminothiocarbonyl, N-ethyl-N-(2-methylbutyl)aminothiocarbonyl, N-ethyl-N-(3-methylbutyl)aminothiocarbonyl, N-ethyl-N-(2,2-dimethylpropyl)aminothiocarbonyl, N-ethyl-N-(1-ethylpropyl)aminothiocarbonyl, N-ethyl-N-hexylaminothiocarbonyl, N-ethyl-N-(1,1-dimethylpropyl)aminothiocarbonyl, N-ethyl-N-(1,2-dimethylpropyl)aminothiocarbonyl, N-ethyl-N-(1-methylpentyl)aminothiocarbonyl, N-ethyl-N-(2-methylpentyl)aminothiocarbonyl, N-ethyl-N-(3-methylpentyl)aminothiocarbonyl, N-ethyl-N-(4-methylpentyl)aminothiocarbonyl, N-ethyl-N-(1,1-dimethylbutyl)aminothiocarbonyl, N-ethyl-N-(1,2-dimethylbutyl)aminothiocarbonyl, N-ethyl-N-(1,3-dimethylbutyl)aminothiocarbonyl, N-ethyl-N-(2,2-dimethylbutyl)aminothiocarbonyl, N-ethyl-N-(2,3-dimethylbutyl)aminothiocarbonyl, N-ethyl-N-(3,3-dimethylbutyl)aminothiocarbonyl, N-ethyl-N-(1-ethylbutyl)aminothiocarbonyl, N-ethyl-N-(2-ethylbutyl)aminothiocarbonyl, N-ethyl-N-(1,1,2-trimethylpropyl)aminothiocarbonyl, N-ethyl-N-(1,2,2-trimethylpropyl)aminothiocarbonyl, N-ethyl-N-(1-ethyl-1-methylpropyl)aminothiocarbonyl, N-ethyl-N-

(1-ethyl-2-methylpropyl)aminothiocarbonyl, N-propyl-N-pentylaminothiocarbonyl, N-butyl-N-pentylaminothiocarbonyl, N,N-dipentylaminothiocarbonyl, N-propyl-N-hexylaminothiocarbonyl, N-butyl-N-hexylaminothiocarbonyl, N-pentyl-N-hexylaminothiocarbonyl or N,N-dihexylaminothiocarbonyl;

three- to six-membered heterocyclyl and also the three- to six-membered heterocyclyl moieties of three- to six-membered heterocyclyl-$C_1$-$C_4$-alkyl: monocyclic saturated or partially unsaturated hydrocarbons having three to six ring members as mentioned above which, in addition to carbon atoms, may contain one to four nitrogen atoms or one to three nitrogen atoms and one oxygen or sulfur atom or one to three oxygen atoms or one to three sulfur atoms and which may be attached via a carbon atom or a nitrogen atom, for example for example 2-oxrianyl, 2-oxetanyl, 3-oxetanyl, 2-aziridinyl, 3-thiethanyl, 1-azetidinyl, 2-azetidinyl, for example 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 1,2,3,4-tetrazolidin-5-yl;

for example 1-pyrrolidinyl, 2-isothiazolidinyl, 2-isothiazolidinyl, 1-pyrazolidinyl, 3-oxazolidinyl, 3-thiazolidinyl, 1-imidazolidinyl, 1,2,4-triazolidin-1-yl, 1,2,4-oxadiazolidin-2-yl, 1,2,4-oxadiazolidin-4-yl, 1,2,4-thiadiazolidin-2-yl, 1,2,4-thiadiazolidin-4-yl, 1,2,3,4-tetrazolidin-1-yl, for example 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 4,5-dihydropyrrol-2-yl, 4,5-dihydropyrrol-3-yl, 2,5-dihydropyrrol-2-yl, 2,5-dihydropyrrol-3-yl, 4,5-dihydroisoxazol-3-yl, 2,5-dihydroisoxazol-3-yl, 2,3-dihydroisoxazol-3-yl, 4,5-dihydroisoxazol-4-yl, 2,5-dihydroisoxazol-4-yl, 2,3-dihydroisoxazol-4-yl, 4,5-dihydroisoxazol-5-yl, 2,5-dihydroisoxazol-5-yl, 2,3-dihydroisoxazol-5-yl, 4,5-dihydroisothiazol-3-yl, 2,5-dihydroisothiazol-3-yl, 2,3-dihydroisothiazol-3-yl, 4,5-dihydroisothiazol-4-yl, 2,5-dihydroisothiazol-4-yl, 2,3-dihydroisothiazol-4-yl, 4,5-dihydroisothiazol-5-yl, 2,5-dihydroisothiazol-5-yl, 2,3-dihydroisothiazol-5-yl, 2,3-dihydropyrazol-3-yl, 2,3-dihydropyrazol-4-yl, 2,3-dihydropyrazol-5-yl, 3,4-dihydropyrazol-3-yl, 3,4-dihydropyrazol-4-yl, 3,4-dihydropyrazol-5-yl, 4,5-dihydropyrazol-3-yl, 4,5-dihydropyrazol-4-yl, 4,5-dihydropyrazol-5-yl, 2,3-dihydroimidazol-2-yl, 2,3-dihydroimidazol-3-yl, 2,3-dihydroimidazol-4-yl, 2,3-dihydroimidazol-5-yl, 4,5-dihydroimidazol-2-yl, 4,5-dihydroimidazol-4-yl, 4,5-dihydroimidazol-5-yl, 2,5-dihydroimidazol-2-yl, 2,5-dihydroimidazol-4-yl, 2,5-dihydroimidazol-5-yl, 2,3-dihydrooxazol-3-yl, 2,3-dihydrooxazol-4-yl, 2,3-dihydrooxazol-5-yl, 3,4-dihydrooxazol-3-yl, 3,4-dihydrooxazol-4-yl, 3,4-dihydrooxazol-5-yl, 2,3-dihydrothiazol-3-yl, 2,3-dihydrothiazol-4-yl, 2,3-dihydrothiazol-5-yl, 3,4-dihydrothiazol-3-yl, 3,4-dihydrothiazol-4-yl, 3,4-dihydrothiazol-5-yl, 3,4-dihydrothiazol-2-yl, 3,4-dihydrothiazol-3-yl, 3,4-dihydrothiazol-4-yl, for example 4,5-dihydropyrrol-1-yl, 2,5-dihydropyrrol-1-yl, 4,5-dihydroisoxazol-2-yl, 2,3-dihydroisoxazol-1-yl, 4,5-dihydroisothiazol-1-yl, 2,3-dihydroisothiazol-1-yl, 2,3-dihydropyrazol-1-yl, 4,5-dihydropyrazol-1-yl, 3,4-dihydropyrazol-1-yl, 2,3-dihydroimidazol-1-yl, 4,5-dihydroimidazol-1-yl, 2,5-dihydroimidazol-1-yl, 2,3-dihydrooxazol-2-yl, 3,4-dihydrooxazol-2-yl, 2,3-dihydrothiazol-2-yl, 3,4-dihydrothiazol-2-yl;

for example 2-piperidinyl, 3-piperidinyl, 4-piperidinyl, 1,3-dioxan-2-yl, 1,3-dioxan-4-yl, 1,3-dioxan-5-yl, 1,4-dioxan-2-yl, 1,3-dithion-2-yl, 1,3-dithion-3-yl, 1,3-dithion-4-yl, 1,4-dithion-2-yl, 1,3-dithian-5-yl, 2-tetrahydropyranyl, 3-tetrahydropyranyl, 4-tetrahydropyranyl, 2-tetrahydrothiopyranyl, 3-tetrahydrothiopyranyl, 4-tetrahydrothiopyranyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl, 1,2,4-hexahydrotriazin-3-yl, tetrahydro-1,3-oxazin-2-yl, tetrahydro-1,3-oxazin-6-yl, 2-morpholinyl, 3-morpholinyl, 1,3,5-trioxan-2-yl;

for example 1-piperidinyl, 1-hexahydropyridazinyl, 1-hexahydropyrimidinyl, 1-piperazinyl, 1,3,5-hexahydrotriazin-1-yl, 1,2,4-hexahydrotriazin-1-yl, tetrahydro-1,3-oxazin-1-yl, 1-morpholinyl;

for example 2H-pyran-2-yl, 2H-pyran-3-yl, 2H-pyran-4-yl, 2H-pyran-5-yl, 2H-pyran-6-yl, 3,6-dihydro-2H-pyran-2-yl, 3,6-dihydro-2H-pyran-3-yl, 3,6-dihydro-2H-pyran-4-yl, 3,6-dihydro-2H-pyran-5-yl, 3,6-dihydro-2H-pyran-6-yl, 3,4-dihydro-2H-pyran-3-yl, 3,4-dihydro-2H-pyran-4-yl, 3,4-dihydro-2H-pyran-6-yl, 2H-thiopyran-2-yl, 2H-thiopyran-3-yl, 2H-thiopyran-4-yl, 2H-thiopyran-5-yl, 2H-thiopyran-6-yl, 5,6-dihydro-4H-1,3-oxazin-2-yl;

aryl and the aryl moiety of aryl-($C_1$-$C_6$-alkyl): a monocyclic to tricyclic aromatic carbocycle having 6 to 14 ring members, such as, for example, phenyl, naphthyl and anthracenyl;

heteroaryl and also the heteroaryl radicals in heteroaryl-$C_1$-$C_4$-alkyl, heteroaryl-$C_1$-$C_4$-alkyl, heteroaryl-$C_2$-$C_4$-alkenyl, heteroaryl-$C_2$-$C_4$-alkynyl, heteroaryl-$C_1$-$C_4$-halogenalkyl, heteroaryl-$C_2$-$C_4$-halogenalkenyl, heteroaryl-$C_2$-$C_4$-halogenalkynyl, heteroaryl-$C_1$-$C_4$-hydroxyalkyl, heteroaryl-$C_2$-$C_4$-hydroxyalkenyl, heteroaryl-$C_2$-$C_4$-hydroxyalkynyl, heteroarylcarbonyl-$C_1$-$C_4$-alkyl, heteroarylcarbonyloxy-$C_1$-$C_4$-alkyl, heteroaryloxycarbonyl-$C_1$-$C_4$-alkyl, heteroaryloxy-$C_1$-$C_4$-alkyl, heteroarylthio-$C_1$-$C_4$-alkyl, heteroarylsulfinyl-$C_1$-$C_4$-alkyl, heteroarylsulfonyl-$C_1$-$C_4$-alkyl: mono- or bicyclic aromatic heteroaryl having 5 to 10 ring members which, in addition to carbon atoms, contains 1 to 4 nitrogen atoms, or 1 to 3 nitrogen atoms and an oxygen or sulfur atom, or an oxygen or a sulfur atom, for example monocycles, such as furyl (for example 2-furyl, 3-furyl), thienyl (for example 2-thienyl, 3-thienyl), pyrrolyl (for example pyrrol-2-yl, pyrrol-3-yl), pyrazolyl (for example pyrazol-3-yl, pyrazol-4-yl), isoxazolyl (for example isoxazol-3-yl, isoxazol-4-yl, isoxazol-5-yl), isothiazolyl (for example isothiazol-3-yl, isothiazol-4-yl, isothiazol-5-yl), imidazolyl (for example imidazol-2-yl, imidazol-4-yl), oxazolyl (for example oxazol-2-yl, oxazol-4-yl, oxazol-5-yl), thiazolyl (for example thiazol-2-yl, thiazol-4-yl, thiazol-5-yl), oxadiazolyl (for example 1,2,3-oxadiazol-4-yl, 1,2,3-oxadiazol-5-yl, 1,2,4-oxadiazol-3-yl, 1,2,4-oxadiazol-5-yl, 1,3,4-oxadiazol-2-yl), thiadiazolyl (for example 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl), triazolyl (for example 1,2,3-triazol-4-yl, 1,2,4-triazol-3-yl), tetrazol-5-yl, pyridyl (for example pyridin-2-yl, pyridin-3-yl, pyridin-4-yl), pyrazinyl (for example pyridazin-3-yl, pyridazin-4-yl), pyrimidinyl (for example pyrimidin-2-yl, pyrimidin-4-yl, pyrimidin-5-yl), pyrazin-2-yl, triazinyl (for example 1,3,5-triazin-2-yl, 1,2,4-triazin-3-yl, 1,2,4-triazin-5-yl, 1,2,4-triazin-6-yl), tetrazinyl (for example 1,2,4,5-tetrazin-3-yl); and also bicycles such as the benzo-fused derivatives of the abovementioned monocycles, for example quinolinyl, isoquinolinyl, indolyl, benzothienyl, benzofuranyl, benzoxazolyl, benzothiazolyl, benzisothiazolyl, benzimidazolyl, benzopyrazolyl, benzothiadiazolyl, benzotriazolyl.

5- or 6-membered heteroaryl having one to four nitrogen atoms or one to three nitrogen atoms and one oxygen or sulfur atom or having one oxygen or sulfur atom: for example aromatic 5-membered heterocycles which are attached via a carbon atom and which, in addition to carbon atoms, may contain one to four nitrogen atoms or one to three nitrogen atoms and one sulfur or oxygen atom or one sulfur or oxygen atom as ring members, for example 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl;

for example aromatic 6-membered heterocycles which are attached via a carbon atom and which, in addition to carbon atoms, may contain one to four, preferably one to three, nitrogen atoms as ring members, for example 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

All phenyl and aryl rings or heterocyclyl and heteroaryl radicals and all phenyl components in phenyl-$C_1$-$C_6$-alkyl, phenylcarbonyl, phenylcarbonyl-$C_1$-$C_6$-alkyl, phenylcarbonylamino-$C_1$-$C_4$-alkyl, phenoxycarbonyl, phenylaminocarbonyl, phenylsulfonylaminocarbonyl, N—($C_1$-$C_6$-alkyl)-N-phenylaminocarbonyl and phenyl-$C_1$-$C_6$-alkylcarbonyl, all aryl components in aryl($C_1$-$C_4$-alkyl), all heteroaryl components in mono- or bicyclic heteroaryl and all heterocyclyl components in heterocyclyl, heterocyclyl-$C_1$-$C_6$-alkyl, heterocyclylcarbonyl, heterocyclylcarbonyl-$C_1$-$C_6$-alkyl, heterocyclyloxycarbonyl, heterocyclylaminocarbonyl, heterocyclylsulfonylaminocarbonyl, N—($C_1$-$C_6$-alkyl)-N-heterocyclylaminocarbonyl and heterocyclyl-$C_1$-$C_6$-alkylcarbonyl are, unless indicated otherwise, preferably unsubstituted or carry one to three halogen atoms and/or one nitro group, one cyano radical and/or one or two methyl, trifluoromethyl, methoxy or trifluoromethoxy substituents.

In a particular embodiment, the variables of the heteroaroyl-substituted serineamides of the formula I are as defined below, these definitions being, both on their own and in combination with one another, particular embodiments of the compounds of the formula I:

Preference is given to the heteroaroyl-substituted serineamides of the formula I in which A is 5-membered heteroaryl having one to four nitrogen atoms or one to three nitrogen atoms and one oxygen or sulfur atom or having one oxygen or sulfur atom;

particularly preferably 5-membered heteroaryl selected from the group consisting of thienyl, furyl, pyrazolyl, imidazolyl, thiazolyl and oxazolyl;

especially preferably 5-membered heteroaryl selected from the group consisting of thienyl, furyl, pyrazolyl and imidazolyl;

where the heteroaryl radicals mentioned are substituted by a $C_1$-$C_6$-haloalkyl radical, preferably in the 2-position by a $C_1$-$C_6$-haloalkyl radical, and may carry 1 to 3 radicals from the group consisting of halogen, cyano, $C_1$-$C_6$-alkyl, $C_3$-$C_6$-cycloalkyl, $C_1$-$C_6$-alkoxy, $C_1$-$C_6$-haloalkoxy and $C_1$-$C_6$-alkoxy-$C_1$-$C_4$-alkyl.

Preference is likewise given to the heteroaroyl-substituted serineamides of the formula I in which A is 5-membered heteroaryl having one to four nitrogen atoms or one to three nitrogen atoms and one oxygen or sulfur atom or having one oxygen or sulfur atom;

particularly preferably 5-membered heteroaryl selected from the group consisting of thienyl, furyl, pyrazolyl, imidazolyl, thiazolyl and oxazolyl;

especially preferably 5-membered heteroaryl selected from the group consisting of thienyl, furyl, pyrazolyl and imidazolyl;

where the heteroaryl radicals mentioned may be partially or fully halogenated and/or may carry 1 to 3 radicals from the group consisting of cyano, $C_1$-$C_6$-alkyl, $C_3$-$C_6$-cycloalkyl, $C_1$-$C_6$-haloalkyl, $C_1$-$C_6$-alkoxy, $C_1$-$C_6$-haloalkoxy and $C_1$-$C_6$-alkoxy-$C_1$-$C_4$-alkyl.

Preference is likewise given to the heteroaroyl-substituted serineamides of the formula I in which A is 5-membered heteroaryl having one to four nitrogen atoms or one to three nitrogen atoms and one oxygen or sulfur atom or having one oxygen atom;

particularly preferably 5-membered heteroaryl selected from the group consisting of furyl, pyrazolyl, imidazolyl, thiazolyl and oxazolyl;

especially preferably 5-membered heteroaryl selected from the group consisting of furyl, pyrazolyl and imidazolyl;

where the heteroaryl radicals mentioned may be partially or fully halogenated and/or may carry 1 to 3 radicals from the group consisting of cyano, $C_1$-$C_6$-alkyl, $C_3$-$C_6$-cycloalkyl, $C_1$-$C_6$-haloalkyl, $C_1$-$C_6$-alkoxy, $C_1$-$C_6$-haloalkoxy and $C_1$-$C_6$-alkoxy-$C_1$-$C_4$-alkyl.

Preference is likewise given to the heteroaroyl-substituted serineamides of the formula I in which A is 6-membered heteroaryl having one to four nitrogen atoms;

particularly preferably pyridyl or pyrimidyl;

especially preferably pyrimidyl;

where the heteroaryl radicals mentioned may be partially or fully halogenated and/or may carry 1 to 3 radicals from the group consisting of cyano, $C_1$-$C_6$-alkyl, $C_3$-$C_6$-cycloalkyl, $C_1$-$C_6$-haloalkyl, $C_1$-$C_6$-alkoxy, $C_1$-$C_6$-haloalkoxy and $C_1$-$C_6$-alkoxy-$C_1$-$C_4$-alkyl.

Preference is likewise given to the heteroaroyl-substituted serineamides of the formula I in which A is 5- or 6-membered heteroaryl having one to four nitrogen atoms or one to three nitrogen atoms and one oxygen or sulfur atom or having one oxygen or sulfur atom
which is substituted by a $C_1$-$C_6$-haloalkyl radical, preferably in the 2-position by a $C_1$-$C_6$-haloalkyl radical, and may carry 1 to 3 radicals from the group consisting of cyano, $C_1$-$C_6$-alkyl, $C_3$-$C_6$-cycloalkyl, $C_1$-$C_6$-alkoxy, $C_1$-$C_6$-haloalkoxy and $C_1$-$C_6$-alkoxy-$C_1$-$C_4$-alkyl.

Preference is likewise given to the heteroaroyl-substituted serineamides of the formula I in which A is 5- or 6-membered heteroaryl selected from the group consisting of pyrrolyl, thienyl, furyl, pyrazolyl, imidazolyl, thiazolyl, oxazolyl, tetrazolyl, pyridyl and pyrimidinyl;
where the heteroaryl radicals mentioned may be partially or fully halogenated and/or may carry 1 to 3 radicals from the group consisting of cyano, $C_1$-$C_6$-alkyl, $C_3$-$C_6$-cycloalkyl, $C_1$-$C_6$-haloalkyl, $C_1$-$C_6$-alkoxy, $C_1$-$C_6$-haloalkoxy and $C_1$-$C_6$-alkoxy-$C_1$-$C_4$-alkyl;
particularly preferably 5- or 6-membered heteroaryl selected from the group consisting of thienyl, furyl, pyrazolyl, imidazolyl, thiazolyl, oxazolyl and pyridyl;
where the heteroaryl radicals mentioned may be partially or fully halogenated and/or may carry 1 to 3 radicals from the group consisting of $C_1$-$C_6$-alkyl, $C_3$-$C_6$-cycloalkyl and $C_1$-$C_6$-haloalkyl;
especially preferably 5-membered heteroaryl selected from the group consisting of thienyl, furyl, pyrazolyl, imidazolyl, thiazolyl and oxazolyl;
where the heteroaryl radicals mentioned may be partially halogenated and/or may carry 1 to 2 radicals from the group consisting of $C_1$-$C_6$-alkyl and $C_1$-$C_4$-haloalkyl;
most preferably 5-membered heteroaryl selected from the group consisting of thienyl, furyl, pyrazolyl and imidazolyl;
where the heteroaryl radicals mentioned may be partially halogenated and/or may carry 1 to 2 radicals from the group consisting of $C_1$-$C_6$-alkyl and $C_1$-$C_4$-haloalkyl.

Preference is likewise given to the heteroaroyl-substituted serineamides of the formula I in which A is 5- or 6-membered heteroaryl selected from the group consisting of pyrrolyl, furyl, pyrazolyl, imidazolyl, thiazolyl, oxazolyl, tetrazolyl, pyridyl and pyrimidinyl;
where the heteroaryl radicals mentioned may be partially or fully halogenated and/or may carry 1 to 3 radicals from the group consisting of cyano, $C_1$-$C_6$-alkyl, $C_3$-$C_6$-cycloalkyl, $C_1$-$C_6$-haloalkyl, $C_1$-$C_6$-alkoxy, $C_1$-$C_6$-haloalkoxy and $C_1$-$C_6$-alkoxy-$C_1$-$C_4$-alkyl;
particularly preferably 5- or 6-membered heteroaryl selected from the group consisting of furyl, pyrazolyl, imidazolyl, thiazolyl, oxazolyl and pyridyl;
where the heteroaryl radicals mentioned may be partially or fully halogenated and/or may carry 1 to 3 radicals from the group consisting of $C_1$-$C_6$-alkyl, $C_3$-$C_6$-cycloalkyl and $C_1$-$C_6$-haloalkyl;
especially preferably 5-membered heteroaryl selected from the group consisting of furyl, pyrazolyl, imidazolyl, thiazolyl and oxazolyl;
where the heteroaryl radicals mentioned may be partially halogenated and/or may carry 1 to 2 radicals from the group consisting of $C_1$-$C_6$-alkyl and $C_1$-$C_4$-haloalkyl;
most preferably 5-membered heteroaryl selected from the group consisting of furyl, pyrazolyl and imidazolyl;
where the heteroaryl radicals mentioned may be partially halogenated and/or may carry 1 to 2 radicals from the group consisting of $C_1$-$C_6$-alkyl and $C_1$-$C_4$-haloalkyl.

Preference is likewise given to the heteroaroyl-substituted serineamides of the formula I in which A is 5- or 6-membered heteroaryl which is attached via carbon and selected from the group consisting of A1 to A14 where

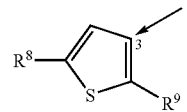
A1

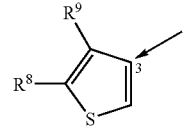
A2

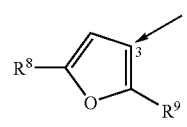
A3

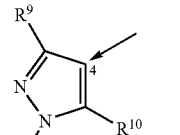
A4

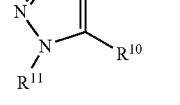
A5

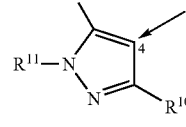
A6

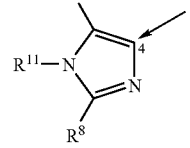
A7

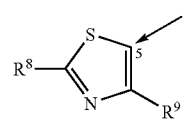
A8

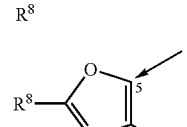
A9

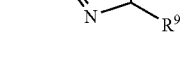
A10

-continued

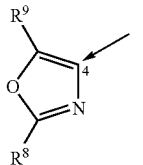
A11

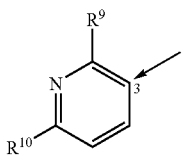
A12

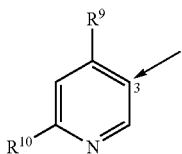
A13

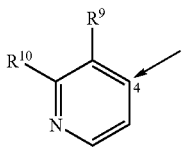
A14 where the arrow indicates the point of attachment and
$R^8$ is hydrogen, halogen, $C_1$-$C_6$-alkyl or $C_1$-$C_6$-haloalkyl;
  particularly preferably hydrogen, $C_1$-$C_4$-alkyl or $C_1$-$C_4$-haloalkyl;
  especially preferably hydrogen or $C_1$-$C_4$-alkyl;
  most preferably hydrogen;
$R^9$ is halogen, $C_1$-$C_6$-alkyl, $C_1$-$C_6$-haloalkyl or $C_1$-$C_6$-haloalkoxy;
  particularly preferably halogen, $C_1$-$C_4$-alkyl or $C_1$-$C_6$-haloalkyl;
  especially preferably halogen or $C_1$-$C_6$-haloalkyl;
  very preferably $C_1$-$C_6$-haloalkyl;
  most preferably $C_1$-$C_4$-haloalkyl;
  with utmost preference $CF_3$;
$R^{10}$ is hydrogen, halogen, $C_1$-$C_6$-alkyl or $C_1$-$C_6$-haloalkyl;
  particularly preferably hydrogen, halogen or $C_1$-$C_4$-haloalkyl;
  especially preferably hydrogen or halogen;
  most preferably hydrogen; and
$R^{11}$ is hydrogen, $C_1$-$C_6$-alkyl, $C_3$-$C_6$-cycloalkyl, $C_1$-$C_6$-haloalkyl or $C_1$-$C_6$-alkoxy-$C_1$-$C_4$-alkyl;
  particularly preferably $C_1$-$C_4$-alkyl, $C_3$-$C_6$-cycloalkyl, $C_1$-$C_4$-haloalkyl or $C_1$-$C_4$-alkoxy-$C_1$-$C_4$-alkyl;
  especially preferably $C_1$-$C_4$-alkyl or $C_1$-$C_4$-haloalkyl;
  most preferably $C_1$-$C_4$-alkyl;
  with utmost preference $CH_3$;
  particularly preferably A1, A2, A3, A4, A5, A6, A8 or A9;
  where $R^8$ to $R^{11}$ are as defined above;
  most preferably A1, A2, A5 or A6;
  where $R^8$ to $R^{11}$ are as defined above.
Preference is likewise given to the heteroaroyl-substituted alanines of the formula I in which
$R^1$ is hydrogen.
Preference is likewise given to the heteroaroyl-substituted alanines of the formula I in which
$R^2$ is hydrogen or hydroxyl;
  particularly preferably hydrogen.

Preference is likewise given to the heteroaroyl-substituted serineamides of the formula I in which
$R^1$ is hydrogen; and
$R^2$ is hydrogen or hydroxyl;
  particularly preferably hydrogen.
Preference is likewise given to the heteroaroyl-substituted serine amides of the formula I in which
$R^3$ is $C_1$-$C_6$-alkyl or $C_1$-$C_6$-haloalkyl;
  particularly preferably $C_1$-$C_6$-alkyl;
  especially preferably $C_1$-$C_4$-alkyl;
  most preferably $CH_3$.
Preference is likewise given to the heteroaroyl-substituted serineamides of the formula I in which
$R^4$ is hydrogen, $C_1$-$C_6$-alkyl, $C_3$-$C_6$-alkenyl, $C_3$-$C_6$-alkynyl, formyl, $C_1$-$C_6$-alkylcarbonyl, $C_2$-$C_6$-alkenylcarbonyl, $C_3$-$C_6$-cycloalkylcarbonyl, $C_1$-$C_6$-alkoxycarbonyl, $C_1$-$C_6$-alkylaminocarbonyl, $C_1$-$C_6$-alkylsulfonylaminocarbonyl, di-($C_1$-$C_6$-alkyl)aminocarbonyl, N—($C_1$-$C_6$-alkoxy)-N—($C_1$-$C_6$-alkyl)aminocarbonyl, di-($C_1$-$C_6$-alkyl)-aminothiocarbonyl, $C_1$-$C_6$-alkoxyimino-$C_1$-$C_6$-alkyl,
  where the alkyl, cycloalkyl and alkoxy radicals mentioned may be partially or fully halogenated and/or may carry one to three of the following groups: cyano, hydroxyl, $C_3$-$C_6$-cycloalkyl, $C_1$-$C_4$-alkoxy, $C_1$-$C_4$-alkylthio, di-($C_1$-$C_4$-alkyl)amino, $C_1$-$C_4$-alkylcarbonyl, hydroxycarbonyl, $C_1$-$C_4$-alkoxycarbonyl, aminocarbonyl, $C_1$-$C_4$-alkylaminocarbonyl, di-($C_1$-$C_4$-alkyl)aminocarbonyl, or $C_1$-$C_4$-alkylcarbonyloxy;
  phenyl, phenyl-$C_1$-$C_6$-alkyl, phenylcarbonyl, phenylcarbonyl-$C_1$-$C_6$-alkyl, phenylsulfonylaminocarbonyl or phenyl-$C_1$-$C_6$-alkylcarbonyl,
  where the phenyl radical may be partially or fully halogenated and/or may carry one to three of the following groups: nitro, cyano, $C_1$-$C_4$-alkyl, $C_1$-$C_4$-haloalkyl, $C_1$-$C_4$-alkoxy or $C_1$-$C_4$-haloalkoxy; or
  $SO_2R^7$;
  particularly preferably hydrogen, $C_1$-$C_6$-alkyl, $C_3$-$C_6$-alkenyl, $C_3$-$C_6$-alkynyl, formyl, $C_1$-$C_6$-alkylcarbonyl, $C_2$-$C_6$-alkenylcarbonyl, $C_1$-$C_6$-alkoxycarbonyl, $C_1$-$C_6$-alkylsulfonylaminocarbonyl, di-($C_1$-$C_6$-alkyl)aminocarbonyl, N—($C_1$-$C_6$-alkoxy)-N—($C_1$-$C_6$-alkyl)aminocarbonyl or di-($C_1$-$C_6$-alkyl)aminothiocarbonyl,
  where the alkyl or alkoxy radicals mentioned may be partially or fully halogenated and/or may carry one to three of the following groups: cyano, $C_1$-$C_4$-alkoxy, $C_1$-$C_4$-alkoxycarbonyl, $C_1$-$C_4$-alkylaminocarbonyl, di-($C_1$-$C_4$-alkyl)aminocarbonyl or $C_1$-$C_4$-alkylcarbonyloxy;
  phenyl-$C_1$-$C_6$-alkyl, phenylcarbonyl, phenylcarbonyl-$C_1$-$C_6$-alkyl, phenylsulfonylaminocarbonyl or phenyl-$C_1$-$C_6$-alkylcarbonyl,
  where the phenyl ring may be partially or fully halogenated and/or may carry one to three of the following groups: nitro, cyano, $C_1$-$C_4$-alkyl, $C_1$-$C_4$-haloalkyl, $C_1$-$C_4$-alkoxy or $C_1$-$C_4$-halooxy; or
  $SO_2R^7$;
  especially preferably hydrogen, $C_1$-$C_6$-alkyl, $C_3$-$C_6$-alkenyl, $C_3$-$C_6$-alkynyl, formyl, $C_1$-$C_6$-alkylcarbonyl, $C_2$-$C_6$-alkenylcarbonyl, $C_1$-$C_6$-alkoxycarbonyl, di-($C_1$-$C_6$-alkyl)aminocarbonyl, N—($C_1$-$C_6$-alkoxy)-N—($C_1$-$C_6$-alkyl)aminocarbonyl, di-($C_1$-$C_6$-alkyl)aminothiocarbonyl, phenyl-$C_1$-$C_6$-alkyl, phenylcarbonyl, phenylcarbonyl-$C_1$-$C_6$-alkyl or phenyl-$C_1$-$C_6$-alkylcarbonyl
  where the phenyl ring may be partially or fully halogenated and/or may carry one to three of the following groups: nitro, cyano, $C_1$-$C_4$-alkyl, $C_1$-$C_4$-haloalkyl, $C_1$-$C_4$-alkoxy or $C_1$-$C_4$-haloalkoxy; or
  $SO_2R^7$.

Preference is likewise given to the heteroaroyl-substituted serineamides of the formula I in which $R^4$ is hydrogen, $C_1$-$C_6$-alkyl, $C_3$-$C_6$-alkenyl, $C_3$-$C_6$-alkynyl, formyl, $C_1$-$C_6$-alkylcarbonyl, $C_2$-$C_6$-alkenylcarbonyl, $C_3$-$C_6$-cycloalkylcarbonyl, $C_1$-$C_6$-alkoxycarbonyl, $C_1$-$C_6$-alkylaminocarbonyl, di-($C_1$-$C_6$-alkyl)aminocarbonyl, N—($C_1$-$C_6$-alkoxy)-N—($C_1$-$C_6$-alkyl)aminocarbonyl, di-($C_1$-$C_6$-alkyl)aminothiocarbonyl, $C_1$-$C_6$-alkoxyimino-$C_1$-$C_6$-alkyl,
  where the alkyl, cycloalkyl or alkoxy radicals mentioned may be partially or fully halogenated and/or may carry one to three of the following groups: cyano, hydroxyl, $C_3$-$C_6$-Cycloalkyl, $C_1$-$C_4$-alkoxy, $C_1$-$C_4$-alkylthio, di-($C_1$-$C_4$-alkyl)amino, $C_1$-$C_4$-alkylcarbonyl, hydroxycarbonyl, $C_1$-$C_4$-alkoxycarbonyl, aminocarbonyl, $C_1$-$C_4$-alkylaminocarbonyl, di-($C_1$-$C_4$-alkyl)aminocarbonyl or $C_1$-$C_4$-alkylcarbonyloxy; or
$SO_2R^7$.

Preference is likewise given to the heteroaroyl-substituted serineamides of the formula I in which $R^4$ is hydrogen, $C_1$-$C_6$-alkyl, $C_3$-$C_6$-alkenyl, $C_3$-$C_6$-alkynyl, formyl, $C_1$-$C_6$-alkyl-carbonyl, $C_1$-$C_6$-alkoxycarbonyl, $C_1$-$C_6$-alkylaminocarbonyl, di-($C_1$-$C_6$-alkyl)-aminocarbonyl, N—($C_1$-$C_6$-alkoxy)-N—($C_1$-$C_6$-alkyl)aminocarbonyl,
  where the alkyl and alkoxy radicals mentioned may be partially or fully halogenated and/or may carry one to three of the following groups: cyano, $C_1$-$C_4$-alkoxy, $C_1$-$C_4$-alkylaminocarbonyl or di-($C_1$-$C_4$-alkyl)aminocarbonyl;
  phenyl-$C_1$-$C_6$-alkyl, phenylcarbonyl, phenylcarbonyl-$C_1$-$C_6$-alkyl, phenyl-aminocarbonyl or N—($C_1$-$C_6$-alkyl)-N-(phenyl)aminocarbonyl,
  where the phenyl ring may be partially or fully halogenated and/or may carry one to three of the following groups: cyano, $C_1$-$C_4$-alkyl or $C_1$-$C_4$-haloalkyl; or
$SO_2R^7$;
  particularly preferably hydrogen, formyl, $C_1$-$C_4$-alkylcarbonyl, $C_1$-$C_4$-alkylamino-carbonyl, di-($C_1$-$C_4$-alkyl)aminocarbonyl, phenylaminocarbonyl, N—($C_1$-$C_4$-alkyl)-N-(phenyl)aminocarbonyl, SO2CH3, $SO_2CF_3$ or $SO_2(C_6H_5)$.

Preference is likewise given to the heteroaroyl-substituted serineamides of the formula I in which $R^5$ is hydrogen or $C_1$-$C_4$-alkyl;
  preferably hydrogen or $CH_3$;
  especially preferably hydrogen.

Preference is likewise given to the heteroaroyl-substituted serineamides of the formula I in which $R^6$ is $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_1$-$C_6$-cyanoalkyl, $C_1$-$C_6$-hydroxyalkyl, $C_2$-$C_6$-hydroxyalkenyl, $C_2$-$C_6$-hydroxyalkynyl, $C_3$-$C_6$-cycloalkyl, $C_3$-$C_6$-cycloalkenyl, 3- to 6-membered heterocyclyl-$C_1$-$C_4$-alkyl,
  where the cycloalkyl, cycloalkenyl or 3- to 6-membered heterocycyl radicals mentioned above may be partially or fully halogenated and/or may carry one to three radicals from the group consisting of oxo, $C_1$-$C_6$-alkyl, $C_1$-$C_6$-haloalkyl, hydroxycarbonyl and $C_1$-$C_6$-alkoxycarbonyl,
  $C_1$-$C_6$-alkoxy-$C_1$-$C_4$-alkyl, $C_1$-$C_6$-haloalkoxy-$C_1$-$C_4$-alkyl, $C_1$-$C_6$-alkoxy-$C_1$-$C_4$-alkoxy-$C_1$-$C_4$-alkyl, $C_1$-$C_6$-alkylthio-$C_1$-$C_4$-alkyl, $C_1$-$C_6$-alkylsulfonylamino-$C_1$-$C_4$-alkyl, hydroxycarbonyl, $C_1$-$C_6$-alkoxycarbonyl, hydroxycarbonyl-$C_1$-$C_4$-alkyl, $C_1$-$C_6$-alkoxycarbonyl-$C_1$-$C_4$-alkyl, $C_1$-$C_6$-haloalkoxycarbonyl-$C_1$-$C_4$-alkyl, $C_1$-$C_6$-alkylcarbonyloxy-$C_1$-$C_4$-alkyl, $C_1$-$C_6$-alkylcarbonylamino-$C_1$-$C_4$-alkyl, di($C_1$-$C_6$-alkyl)carbonylamino-$C_1$-$C_4$-alkyl, di($C_1$-$C_6$-alkyl)aminocarbonyl-amino-$C_1$-$C_4$-alkyl, [($C_1$-$C_6$-alkyl)aminocarbonyl]amino-$C_1$-$C_4$-alkyl, [di($C_1$-$C_6$-alkyl)aminocarbonyl-oxy]-$C_1$-$C_4$-alkyl, {di[di($C_1$-$C_6$-alkyl)amino]carbonyloxy}-$C_1$-$C_4$-alkyl, formylamino-$C_1$-$C_4$-alkyl,
  phenyl-$C_1$-$C_4$-alkyl, phenyl-$C_2$-$C_4$-alkenyl, phenyl-$C_2$-$C_4$-alkynyl, phenyl-$C_1$-$C_4$-haloalkyl, phenyl-$C_2$-$C_4$-haloalkenyl, phenyl-$C_1$-$C_4$-hydroxyalkyl, phenyloxy-$C_1$-$C_4$-alkyl, phenylthio-$C_1$-$C_4$-alkyl, phenylsulfinyl-$C_1$-$C_4$-alkyl, phenylsulfonyl-$C_1$-$C_4$-alkyl,
  heteroaryl-$C_1$-$C_4$-alkyl, heteroaryl-$C_1$-$C_4$-hydroxyalkyl, heteroaryloxy-$C_1$-$C_4$-alkyl, heteroarylthio-$C_1$-$C_4$-alkyl, heteroarylsulfinyl-$C_1$-$C_4$-alkyl or heteroarylsulfonyl-$C_1$-$C_4$-alkyl,
  where the phenyl and heteroaryl radicals mentioned above may be partially or fully halogenated and/or may carry one to three radicals from the group consisting of cyano, nitro, $C_1$-$C_6$-alkyl, $C_1$-$C_6$-haloalkyl, hydroxy, $C_1$-$C_6$-alkoxy, $C_1$-$C_6$-haloalkoxy, hydroxycarbonyl, $C_1$-$C_6$-alkoxycarbonyl, hydroxycarbonyl-$C_1$-$C_6$-alkoxy, $C_1$-$C_6$-alkylsulfonylamino and $C_1$-$C_6$-haloalkylsulfonylamino;
  particularly preferably $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_1$-$C_6$-hydroxyalkyl, $C_1$-$C_6$-alkoxy-$C_1$-$C_4$-alkyl, $C_1$-$C_6$-haloalkoxy-$C_1$-$C_4$-alkyl, hydroxycarbonyl-$C_1$-$C_4$-alkyl, $C_1$-$C_6$-alkoxycarbonyl-$C_1$-$C_4$-alkyl, $C_1$-$C_6$-alkylcarbonyloxy-$C_1$-$C_4$-alkyl, $C_1$-$C_6$-alkylcarbonylamino-$C_1$-$C_4$-alkyl, [di($C_1$-$C_6$-alkyl)aminocarbonyloxy]-$C_1$-$C_4$-alkyl, {di[di($C_1$-$C_6$-alkyl)amino]-carbonyloxy}-$C_1$-$C_4$-alkyl, formylamino-$C_1$-$C_4$-alkyl;
  phenyl-$C_1$-$C_4$-alkyl, phenyl-$C_2$-$C_4$-alkenyl, phenyl-$C_2$-$C_4$-alkynyl, phenyl-$C_1$-$C_4$-haloalkyl, phenyl-$C_2$-$C_4$-haloalkenyl, phenyl-$C_1$-$C_4$-hydroxyalkyl, phenyloxy-$C_1$-$C_4$-alkyl, phenylthio-$C_1$-$C_4$-alkyl, phenylsulfinyl-$C_1$-$C_4$-alkyl or phenylsulfonyl-$C_1$-$C_4$-alkyl,
  where the phenyl radicals mentioned above may be partially or fully halogenated and/or may carry one to three radicals from the group consisting of $C_1$-$C_6$-alkyl, $C_1$-$C_6$-haloalkyl, $C_1$-$C_6$-alkoxy, hydroxycarbonyl, $C_1$-$C_6$-alkoxycarbonyl, $C_1$-$C_6$-alkylsulfonylamino and $C_1$-$C_6$-haloalkylsulfonylamino;
  especially preferably $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_1$-$C_6$-hydroxyalkyl, hydroxycarbonyl-$C_1$-$C_4$-alkyl, $C_1$-$C_6$-alkoxycarbonyl-$C_1$-$C_4$-alkyl, [di($C_1$-$C_6$-alkyl) aminocarbonyloxy]-$C_1$-$C_4$-alkyl, {di[di($C_1$-$C_6$-alkyl)amino]carbonyloxy}-$C_1$-$C_4$-alkyl, formylamino-$C_1$-$C_4$-alkyl; phenyl-$C_1$-$C_4$-alkyl, phenyl-$C_2$-$C_4$-alkenyl, phenyl-$C_1$-$C_4$-hydroxyalkyl or phenylthio-$C_1$-$C_4$-alkyl;
  most preferably $C_1$-$C_6$-alkyl, $C_2$-$C_6$-alkenyl, $C_1$-$C_6$-haloalkyl, $C_2$-$C_6$-haloalkenyl, $C_1$-$C_6$-hydroxyalkyl, hydroxycarbonyl-$C_1$-$C_4$-alkyl, formylamino-$C_1$-$C_4$-alkyl, phenyl-$C_1$-$C_4$-alkyl or phenyl-$C_1$-$C_4$-hydroxyalkyl.

Preference is likewise given to the heteroaroyl-substituted serineamides of the formula I in which $R^6$ is $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_1$-$C_6$-cyanoalkyl, $C_1$-$C_6$-hydroxyalkyl, $C_2$-$C_6$-hydroxyalkenyl, $C_2$-$C_6$-hydroxyalkynyl, $C_3$-$C_6$-cycloalkyl, $C_3$-$C_6$-cycloalkenyl, 3- to 6-membered heterocyclyl,
  where the cycloalkyl, cycloalkenyl or 3- to 6-membered heterocycyl radicals mentioned above may be partially or fully halogenated and/or may carry one to three radicals from the group consisting of oxo, $C_1$-$C_6$-alkyl, $C_1$-$C_6$-haloalkyl, hydroxycarbonyl and $C_1$-$C_6$-alkoxycarbonyl, $C_1$-$C_6$-alkoxy-$C_1$-$C_4$-alkyl, $C_1$-$C_6$-haloalkoxy-$C_1$-$C_4$-alkyl, $C_1$-$C_6$-alkoxy-$C_1$-$C_4$-alkoxy-$C_1$-$C_4$-alkyl, $C_1$-$C_6$-alkylthio-$C_1$-$C_4$-alkyl, $C_1$-$C_6$-alkylsulfonylamino-$C_1$-$C_4$-alkyl, hydroxycarbonyl, $C_1$-$C_6$-alkoxycarbonyl, hydroxycarbonyl-$C_1$-$C_4$-alkyl, $C_1$-$C_6$-alkoxycarbonyl-$C_1$-$C_4$-alkyl, $C_1$-$C_6$-haloalkoxycarbonyl-$C_1$-$C_4$-alkyl, $C_1$-$C_6$-alkylcarbonyloxy-$C_1$-$C_4$-alkyl, $C_1$-$C_6$-alkylcarbonylamino-$C_1$-$C_4$-alkyl, di($C_1$-$C_6$-alkyl)carbonylamino-$C_1$-$C_4$-alkyl, di($C_1$-$C_6$-alkyl)aminocarbonylamino-$C_1$-$C_4$-alkyl, [($C_1$-$C_6$-alkyl)aminocarbonyl]amino-$C_1$-$C_4$-alkyl, [di($C_1$-$C_6$-alkyl)aminocarbonyl-oxy]-$C_1$-$C_4$-alkyl, formylamino-$C_1$-$C_4$-alkyl, phenyl-$C_1$-$C_4$-alkyl, phenyl-$C_2$-$C_4$-alkenyl, phenyl-$C_2$-$C_4$-alkynyl, phenyl-$C_1$-$C_4$-haloalkyl, phenyl-$C_2$-$C_4$-haloalkenyl, phenyl-$C_1$-$C_4$-hydroxyalkyl, phenyloxy-$C_1$-$C_4$-alkyl, phenylthio-$C_1$-$C_4$-alkyl, phenylsulfinyl-$C_1$-$C_4$-alkyl, phenylsulfonyl-$C_1$-$C_4$-alkyl, heteroaryl-$C_1$-$C_4$-alkyl, heteroaryl-$C_1$-$C_4$-hydroxyalkyl, heteroaryloxy-$C_1$-$C_4$-alkyl, heteroarylthio-$C_1$-$C_4$-alkyl, heteroarylsulfinyl-$C_1$-$C_4$-alkyl or heteroarylsulfonyl-$C_1$-$C_4$-alkyl, where the phenyl and heteroaryl radicals mentioned above may be partially or fully halogenated and/or may carry one to three radicals from the group consisting of cyano, nitro, $C_1$-$C_6$-alkyl, $C_1$-$C_6$-haloalkyl, hydroxy, $C_1$-$C_6$-alkoxy, $C_1$-$C_6$-haloalkoxy, hydroxycarbonyl, $C_1$-$C_6$-alkoxycarbonyl, hydroxycarbonyl-$C_1$-$C_6$-alkoxy, $C_1$-$C_6$-alkylsulfonylamino and $C_1$-$C_6$-haloalkylsulfonylamino;

particularly preferably $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_1$-$C_6$-hydroxyalkyl, 3- to 6-membered heterocyclyl, $C_1$-$C_6$-alkoxy-$C_1$-$C_4$-alkyl, $C_1$-$C_6$-alkoxy-$C_1$-$C_4$-alkoxy-$C_1$-$C_4$-alkyl, $C_1$-$C_6$-haloalkoxy-$C_1$-$C_4$-alkyl, hydroxycarbonyl-$C_1$-$C_4$-alkyl, $C_1$-$C_6$-alkoxycarbonyl-$C_1$-$C_4$-alkyl, $C_1$-$C_6$-alkylcarbonyloxy-$C_1$-$C_4$-alkyl, $C_1$-$C_6$-alkylcarbonylamino-$C_1$-$C_4$-alkyl, [di($C_1$-$C_6$-alkyl)aminocarbonyloxy]$C_1$-$C_4$-alkyl, formylamino-$C_1$-$C_4$-alkyl;

phenyl-$C_1$-$C_4$-alkyl, phenyl-$C_2$-$C_4$-alkenyl, phenyl-$C_2$-$C_4$-alkynyl, phenyl-$C_1$-$C_4$-haloalkyl, phenyl-$C_2$-$C_4$-haloalkenyl, phenyl-$C_1$-$C_4$-hydroxyalkyl, phenyloxy-$C_1$-$C_4$-alkyl, phenylthio-$C_1$-$C_4$-alkyl, phenylsulfinyl-$C_1$-$C_4$-alkyl or phenylsulfonyl-$C_1$-$C_4$-alkyl, where the phenyl radicals mentioned above may be partially or fully halogenated and/or may carry one to three radicals from the group consisting of $C_1$-$C_6$-alkyl, $C_1$-$C_6$-haloalkyl, $C_1$-$C_6$-alkoxy, hydroxycarbonyl, $C_1$-$C_6$-alkoxycarbonyl, $C_1$-$C_6$-alkylsulfonylamino and $C_1$-$C_6$-haloalkylsulfonylamino;

especially preferably $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_1$-$C_6$-hydroxyalkyl, 3- to 6-membered heterocyclyl, $C_1$-$C_6$-alkoxy-$C_1$-$C_4$-alkyl, $C_1$-$C_6$-alkoxy-$C_1$-$C_4$-alkoxy-$C_1$-$C_4$-alkyl, hydroxycarbonyl-$C_1$-$C_4$-alkyl, $C_1$-$C_6$-alkoxycarbonyl-$C_1$-$C_4$-alkyl, [di($C_1$-$C_6$-alkyl)aminocarbonyl-oxy]$C_1$-$C_4$-alkyl, formylamino-$C_1$-$C_4$-alkyl;

phenyl-$C_1$-$C_4$-alkyl, phenyl-$C_2$-$C_4$-alkenyl, phenyl-$C_1$-$C_4$-hydroxyalkyl or phenylthio-$C_1$-$C_4$-alkyl;

most preferably $C_1$-$C_6$-alkyl, $C_2$-$C_6$-alkenyl, $C_1$-$C_6$-haloalkyl, $C_2$-$C_6$-haloalkenyl, $C_1$-$C_6$-hydroxyalkyl, 3- to 6-membered heterocyclyl, $C_1$-$C_6$-alkoxy-$C_1$-$C_4$-alkyl, $C_1$-$C_6$-alkoxy-$C_1$-$C_4$-alkoxy-$C_1$-$C_4$-alkyl, hydroxycarbonyl-$C_1$-$C_4$-alkyl, formylamino-$C_1$-$C_4$-alkyl, phenyl-$C_1$-$C_4$-alkyl or phenyl-$C_1$-$C_4$-hydroxyalkyl.

Preference is likewise given to the heteroaroyl-substituted serineamides of the formula I in which $R^7$ is $C_1$-$C_6$-alkyl, $C_1$-$C_6$-haloalkyl or phenyl,
where the phenyl radical may be partially or partially halogenated and/or may be substituted by $C_1$-$C_4$-alkyl;
particularly preferably $C_1$-$C_4$-alkyl, $C_1$-$C_4$-haloalkyl or phenyl;
especially preferably methyl, trifluoromethyl or phenyl.

Particular preference is given to the heteroaroyl-substituted serineamides of the formula I in which A is 5- or 6-membered heteroaryl selected from the group consisting of thienyl, furyl, pyrazolyl, imidazolyl, thiazolyl, oxazolyl and pyridyl;
where the heteroaryl radicals mentioned may be partially or fully halogenated and/or may carry 1 to 3 radicals from the group consisting of $C_1$-$C_6$-alkyl, $C_3$-$C_6$-cycloalkyl and $C_1$-$C_6$-haloalkyl;

$R^1$ and $R^2$ are hydrogen;
$R^3$ is $C_1$-$C_4$-alkyl,
particularly preferably $CH_3$;
$R^4$ is hydrogen, formyl, $C_1$-$C_4$-alkylcarbonyl, $C_1$-$C_4$-alkylaminocarbonyl, di-($C_1$-$C_4$-alkyl)aminocarbonyl, phenylaminocarbonyl, N—($C_1$-$C_4$-alkyl)-N-(phenyl)aminocarbonyl, $SO_2CH_3$, $SO_2CF_3$ or $SO_2(C_6H_5)$; and
$R^5$ is hydrogen; and
$R^6$ is $C_1$-$C_6$-alkyl, $C_2$-$C_6$-alkenyl, $C_1$-$C_6$-haloalkyl, $C_2$-$C_6$-haloalkenyl, $C_1$-$C_6$-hydroxyalkyl, $C_1$-$C_6$-alkoxy-$C_1$-$C_4$-alkyl, $C_1$-$C_6$-alkoxy-$C_1$-$C_4$-alkoxy-$C_1$-$C_4$-alkyl, 3- to 6-membered heterocyclyl, hydroxycarbonyl-$C_1$-$C_4$-alkyl, phenyl-$C_1$-$C_4$-alkyl, phenyl-$C_1$-$C_4$-hydroxyalkyl.

Most preference is given to the compounds of the formula I.a (corresponds to formula I where A=A-1 where $R^8$=H, $R^9$=$CF_3$, $R^1$, $R^2$ and $R^5$=H; $R^3$=$CH_3$), in particular to the compounds of the formulae I.a.1 to I.a.138 of Table 1, where the definitions of the variables A and $R^1$ to $R^6$ are of particular importance for the compounds according to the invention not only in combination with one another, but in each case also on their own.

TABLE 1

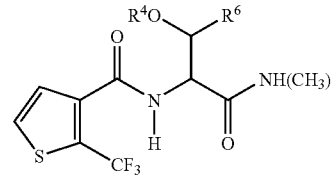

I.a

| No. | $R^4$ | $R^6$ |
|---|---|---|
| I.a.1 | H | $CH_3$ |
| I.a.2 | H | $CH_2CH_3$ |
| I.a.3 | H | $CH=CH_2$ |
| I.a.4 | H | $CH=CHCH_3$ |
| I.a.5 | H | $CH=C(CH_3)_2$ |
| I.a.6 | H | $C{\equiv}CH$ |
| I.a.7 | H | $CF_3$ |
| I.a.8 | H | $CHF_2$ |
| I.a.9 | H | $CF_2CF_3$ |
| I.a.10 | H | $CF_2CHF_2$ |
| I.a.11 | H | $CH=CCl_2$ |
| I.a.12 | H | $CH=CF_2$ |
| I.a.13 | H | $CH_2OH$ |
| I.a.14 | H | $CH_2CH_2OH$ |
| I.a.15 | H | $CH(OH)CH_2OH$ |
| I.a.16 | H | cyclopropyl |
| I.a.17 | H | cyclohexyl |
| I.a.18 | H | $CH_2COOH$ |
| I.a.19 | H | $CH_2O(CO)CH_3$ |

TABLE 1-continued

I.a

Structure: thiophene with CF₃ substituent, C(O)NH-CH(C(O)NH(CH₃))-CH(OR⁴)(R⁶)

| No. | R⁴ | R⁶ |
|---|---|---|
| I.a.20 | H | CH₂O(CO)N(CH₃)₂ |
| I.a.21 | H | C≡C(C₆H₅) |
| I.a.22 | H | CH(OH)CH(OH)C₆H₅ |
| I.a.23 | H | CH₂SC(2-F—C₆H₄) |
| I.a.24 | C(O)CH₃ | CH₃ |
| I.a.25 | C(O)CH₃ | CH₂CH₃ |
| I.a.26 | C(O)CH₃ | CH═CH₂ |
| I.a.27 | C(O)CH₃ | CH═CHCH₃ |
| I.a.28 | C(O)CH₃ | CH═C(CH₃)₂ |
| I.a.29 | C(O)CH₃ | C≡CH |
| I.a.30 | C(O)CH₃ | CF₃ |
| I.a.31 | C(O)CH₃ | CHF₂ |
| I.a.32 | C(O)CH₃ | CF₂CF₃ |
| I.a.33 | C(O)CH₃ | CF₂CHF₂ |
| I.a.34 | C(O)CH₃ | CH═CCl₂ |
| I.a.35 | C(O)CH₃ | CH═CF₂ |
| I.a.36 | C(O)CH₃ | CH₂OH |
| I.a.37 | C(O)CH₃ | CH₂CH₂OH |
| I.a.38 | C(O)CH₃ | CH(OH)CH₂OH |
| I.a.39 | C(O)CH₃ | cyclopropyl |
| I.a.40 | C(O)CH₃ | cyclohexyl |
| I.a.41 | C(O)CH₃ | CH₂COOH |
| I.a.42 | C(O)CH₃ | CH₂O(CO)CH₃ |
| I.a.43 | C(O)CH₃ | CH₂O(CO)N(CH₃)₂ |
| I.a.44 | C(O)CH₃ | C≡C(C₆H₅) |
| I.a.45 | C(O)CH₃ | CH(OH)CH(OH)C₆H₅ |
| I.a.46 | C(O)CH₃ | CH₂S(2-F—C₆H₄) |
| I.a.47 | C(O)tertC₄H₉ | CH₃ |
| I.a.48 | C(O)tertC₄H₉ | CH₂CH₃ |
| I.a.49 | C(O)tertC₄H₉ | CH═CH₂ |
| I.a.50 | C(O)tertC₄H₉ | CH═CHCH₃ |
| I.a.51 | C(O)tertC₄H₉ | CH═C(CH₃)₂ |
| I.a.52 | C(O)tertC₄H₉ | C≡CH |
| I.a.53 | C(O)tertC₄H₉ | CF₃ |
| I.a.54 | C(O)tertC₄H₉ | CHF₂ |
| I.a.55 | C(O)tertC₄H₉ | CF₂CF₃ |
| I.a.56 | C(O)tertC₄H₉ | CF₂CHF₂ |
| I.a.57 | C(O)tertC₄H₉ | CH═CCl₂ |
| I.a.58 | C(O)tertC₄H₉ | CH═CF₂ |
| I.a.59 | C(O)tertC₄H₉ | CH₂OH |
| I.a.60 | C(O)tertC₄H₉ | CH₂CH₂OH |
| I.a.61 | C(O)tertC₄H₉ | CH(OH)CH₂OH |
| I.a.62 | C(O)tertC₄H₉ | cyclopropyl |
| I.a.63 | C(O)tertC₄H₉ | cyclohexyl |
| I.a.64 | C(O)tertC₄H₉ | CH₂COOH |
| I.a.65 | C(O)tertC₄H₉ | CH₂O(CO)CH₃ |
| I.a.66 | C(O)tertC₄H₉ | CH₂O(CO)N(CH₃)₂ |
| I.a.67 | C(O)tertC₄H₉ | C≡C(C₆H₅) |
| I.a.68 | C(O)tertC₄H₉ | CH(OH)CH(OH)C₆H₅ |
| I.a.69 | C(O)tertC₄H₉ | CH₂S(2-F—C₆H₄) |
| I.a.70 | C(O)N(CH₃)₂ | CH₃ |
| I.a.71 | C(O)N(CH₃)₂ | CH₂CH₃ |
| I.a.72 | C(O)N(CH₃)₂ | CH═CH₂ |
| I.a.73 | C(O)N(CH₃)₂ | CH═CHCH₃ |
| I.a.74 | C(O)N(CH₃)₂ | CH═C(CH₃)₂ |
| I.a.75 | C(O)N(CH₃)₂ | C≡CH |
| I.a.76 | C(O)N(CH₃)₂ | CF₃ |
| I.a.77 | C(O)N(CH₃)₂ | CHF₂ |
| I.a.78 | C(O)N(CH₃)₂ | CF₂CF₃ |
| I.a.79 | C(O)N(CH₃)₂ | CF₂CHF₂ |
| I.a.80 | C(O)N(CH₃)₂ | CH═CCl₂ |
| I.a.81 | C(O)N(CH₃)₂ | CH═CF₂ |
| I.a.82 | C(O)N(CH₃)₂ | CH₂OH |
| I.a.83 | C(O)N(CH₃)₂ | CH₂CH₂OH |
| I.a.84 | C(O)N(CH₃)₂ | CH(OH)CH₂OH |
| I.a.85 | C(O)N(CH₃)₂ | cyclopropyl |
| I.a.86 | C(O)N(CH₃)₂ | cyclohexyl |
| I.a.87 | C(O)N(CH₃)₂ | CH₂COOH |
| I.a.88 | C(O)N(CH₃)₂ | CH₂O(CO)CH₃ |
| I.a.89 | C(O)N(CH₃)₂ | CH₂O(CO)N(CH₃)₂ |
| I.a.90 | C(O)N(CH₃)₂ | C≡C(C₆H₅) |
| I.a.91 | C(O)N(CH₃)₂ | CH(OH)CH(OH)C₆H₅ |
| I.a.92 | C(O)N(CH₃)₂ | CH₂S(2-F—C₆H₄) |
| I.a.93 | C(O)N(CH₃)(C₆H₅) | CH₃ |
| I.a.94 | C(O)N(CH₃)(C₆H₅) | CH₂CH₃ |
| I.a.95 | C(O)N(CH₃)(C₆H₅) | CH═CH₂ |
| I.a.96 | C(O)N(CH₃)(C₆H₅) | CH═CHCH₃ |
| I.a.97 | C(O)N(CH₃)(C₆H₅) | CH═C(CH₃)₂ |
| I.a.98 | C(O)N(CH₃)(C₆H₅) | C≡CH |
| I.a.99 | C(O)N(CH₃)(C₆H₅) | CF₃ |
| I.a.100 | C(O)N(CH₃)(C₆H₅) | CHF₂ |
| I.a.101 | C(O)N(CH₃)(C₆H₅) | CF₂CF₃ |
| I.a.102 | C(O)N(CH₃)(C₆H₅) | CF₂CHF₂ |
| I.a.103 | C(O)N(CH₃)(C₆H₅) | CH═CCl₂ |
| I.a.104 | C(O)N(CH₃)(C₆H₅) | CH═CF₂ |
| I.a.105 | C(O)N(CH₃)(C₆H₅) | CH₂OH |
| I.a.106 | C(O)N(CH₃)(C₆H₅) | CH₂CH₂OH |
| I.a.107 | C(O)N(CH₃)(C₆H₅) | CH(OH)CH₂OH |
| I.a.108 | C(O)N(CH₃)(C₆H₅) | cyclopropyl |
| I.a.109 | C(O)N(CH₃)(C₆H₅) | cyclohexyl |
| I.a.110 | C(O)N(CH₃)(C₆H₅) | CH₂COOH |
| I.a.111 | C(O)N(CH₃)(C₆H₅) | CH₂O(CO)CH₃ |
| I.a.112 | C(O)N(CH₃)(C₆H₅) | CH₂O(CO)N(CH₃)₂ |
| I.a.113 | C(O)N(CH₃)(C₆H₅) | C≡C(C₆H₅) |
| I.a.114 | C(O)N(CH₃)(C₆H₅) | CH(OH)CH(OH)C₆H₅ |
| I.a.115 | C(O)N(CH₃)(C₆H₅) | CH₂S(2-F—C₆H₄) |
| I.a.116 | SO₂CH₃ | CH₃ |
| I.a.117 | SO₂CH₃ | CH₂CH₃ |
| I.a.118 | SO₂CH₃ | CH═CH₂ |
| I.a.119 | SO₂CH₃ | CH═CHCH₃ |
| I.a.120 | SO₂CH₃ | CH═C(CH₃)₂ |
| I.a.121 | SO₂CH₃ | C≡CH |
| I.a.122 | SO₂CH₃ | CF₃ |
| I.a.123 | SO₂CH₃ | CHF₂ |
| I.a.124 | SO₂CH₃ | CF₂CF₃ |
| I.a.125 | SO₂CH₃ | CF₂CHF₂ |
| I.a.126 | SO₂CH₃ | CH═CCl₂ |
| I.a.127 | SO₂CH₃ | CH═CF₂ |
| I.a.128 | SO₂CH₃ | CH₂OH |
| I.a.129 | SO₂CH₃ | CH₂CH₂OH |
| I.a.130 | SO₂CH₃ | CH(OH)CH₂OH |
| I.a.131 | SO₂CH₃ | cyclopropyl |
| I.a.132 | SO₂CH₃ | cyclohexyl |
| I.a.133 | SO₂CH₃ | CH₂COOH |
| I.a.134 | SO₂CH₃ | CH₂O(CO)CH₃ |
| I.a.135 | SO₂CH₃ | CH₂O(CO)N(CH₃)₂ |
| I.a.136 | SO₂CH₃ | C≡C(C₆H₅) |
| I.a.137 | SO₂CH₃ | CH(OH)CH(OH)C₆H₅ |
| I.a.138 | SO₂CH₃ | CH₂S(2-F—C₆H₄) |

Most preference is given to the compounds of the formula I.b, in particular to the compounds of the formulae I.b.1 to I.b.138, which differ from the corresponding compounds of the formulae I.a.1 to I.a.138 in that A is A1 where $R^8$=CH₃ and $R^9$=CF₃.

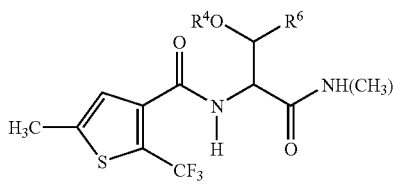

I.b

Most preference is given to the compounds of the formula I.c, in particular to the compounds of the formulae I.c.1 to I.c.138, which differ from the corresponding compounds of the formulae I.a.1 to I.a.138 in that A is A2 where $R^8$=H and $R^9$=$CF_3$.

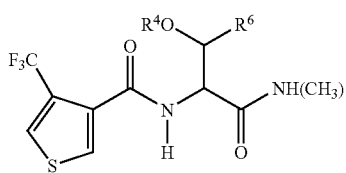

I.c

Most preference is given to the compounds of the formula I.d, in particular to the compounds of the formulae I.d.1 to I.d.138, which differ from the corresponding compounds of the formulae I.a.1 to I.a.138 in that A is A3 where $R^8$=H and $R^9$=$CF_3$.

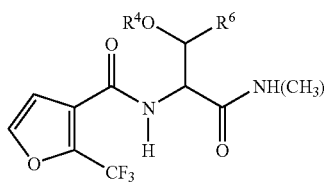

I.d

Most preference is given to the compounds of the formula I.e, in particular to the compounds of the formulae I.e.1 to I.e.138, which differ from the corresponding compounds of the formulae I.e.1 to I.e.138 in that A is A3 where $R^8$=$CH_3$ and $R^9$=$CF_3$.

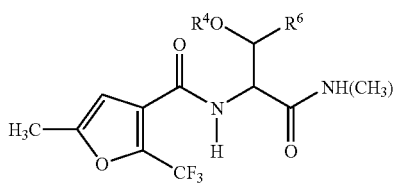

I.e

Most preference is given to the compounds of the formula I.f, in particular to the compounds of the formulae I.f.1 to I.f.138, which differ from the corresponding compounds of the formulae I.a.1 to I.a.138 in that A is A4 where $R^8$=H and $R^9$=$CF_3$.

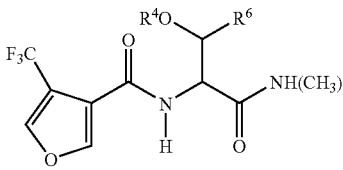

I.f

Most preference is given to the compounds of the formula I.g, in particular to the compounds of the formulae I.g.1 to I.g.138, which differ from the corresponding compounds of the formulae I.a.1 to I.a.138 in that A is A5 where $R^{11}$=H, $R^9$=$CF_3$ and $R^{10}$=H.

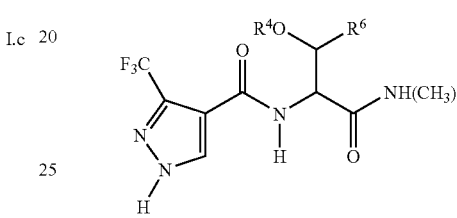

I.g

Most preference is given to the compounds of the formula I.h, in particular to the compounds of the formulae I.h.1 to I.h.138, which differ from the corresponding compounds of the formulae I.a.1 to I.a.138 in that A is A5 where $R^{11}$=$CH_3$, $R^9$=$CF_3$ and $R^{10}$=H.

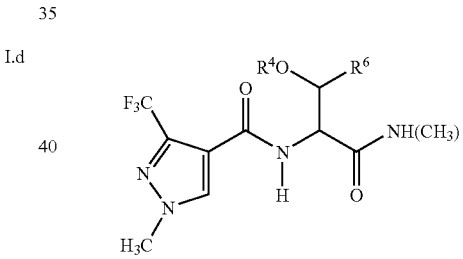

I.h

Most preference is given to the compounds of the formula I.j, in particular to the compounds of the formulae I.j.1 to I.j.138, which differ from the corresponding compounds of the formulae I.a.1 to I.a.138 in that A is A8 where $R^8$=H and $R^9$=$CF_3$.

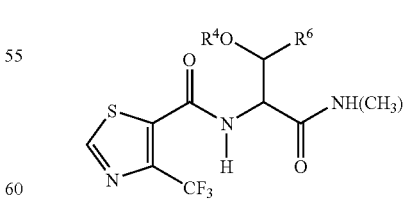

I.j

Most preference is given to the compounds of the formula I.k, in particular to the compounds of the formulae I.k.1 to I.k.138, which differ from the corresponding compounds of the formulae I.a.1 to I.a.138 in that A is A8 where $R^8$=$CH_3$ and $R^9$=$CF_3$.

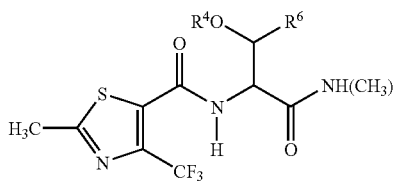

I.k

The heteroaroyl-substituted serineamides of the formula I can be obtained by different routes, for example by the following processes:

Process A

Serine derivatives of the formula V are initially reacted with heteroaryl acids/heteroaryl acid derivatives of the formula IV to give the corresponding heteroaroyl derivatives of the formula III which are then reacted with amines of the formula II to give the desired heteroaroyl-substituted serineamides of the formula I:

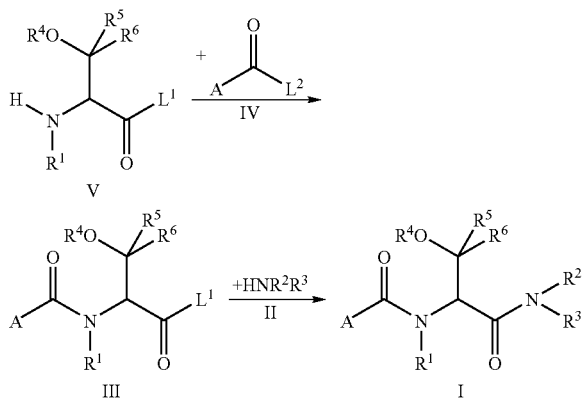

$L^1$ is a nucleophilically replaceable leaving group, for example hydroxyl or $C_1$-$C_6$-alkoxy.

$L^2$ is a nucleophilically replaceable leaving group, for example hydroxyl, halogen, $C_1$-$C_6$-alkylcarbonyl, $C_1$-$C_6$-alkoxycarbonyl, $C_1$-$C_4$-alkylsulfonyl, phosphoryl or isoureyl.

The reaction of the serine derivatives of the formula V with heteroaryl acids/heteroaryl acid derivatives of the formula IV where $L^2$ is hydroxyl to give heteroaroyl derivatives of the formula III is carried out in the presence of an activating reagent and a base, usually at temperatures of from 0° C. to the boiling point of the reaction mixture, preferably from 0° C. to 110° C., particularly preferably at room temperature, in an inert organic solvent [cf. Bergmann, E. D.; et al., J Chem Soc 1951, 2673; Zhdankin, V. V.; et al., Tetrahedron Lett. 2000, 41 (28), 5299-5302; Martin, S. F. et al., Tetrahedron Lett. 1998, 39 (12), 1517-1520; Jursic, B. S. et al., Synth Commun 2001, 31 (4), 555-564; Albrecht, M. et al., Synthesis 2001, (3), 468-472; Yadav, L. D. S. et al., Indian J. Chem B. 41(3), 593-595 (2002); Clark, J. E. et al., Synthesis (10), 891-894 (1991)].

Suitable activating reagents are condensing agents, such as, for example, polystyrene-bound dicyclohexylcarbodiimide, diisopropylcarbodiimide, carbonyldiimidazole, chloroformic esters, such as methyl chloroformate, ethyl chloroformate, isopropyl chloroformate, isobutyl chloroformate, sec-butyl chloroformate or allyl chloroformate, pivaloyl chloride, polyphosphoric acid, propanephosphonic anhydride, bis(2-oxo-3-oxazolidinyl)phosphoryl chloride (BOPCl) or sulfonyl chlorides, such as methane-sulfonyl chloride, toluenesulfonyl chloride or benzenesulfonyl chloride.

Suitable solvents are aliphatic hydrocarbons, such as pentane, hexane, cyclohexane and mixtures of $C_5$-$C_8$-alkanes, aromatic hydrocarbons, such as benzene, toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran (THF), nitriles, such as acetonitrile and propionitrile, ketones, such as acetone, methyl ethyl ketone, diethyl ketone and tert-butyl methyl ketone, and also dimethyl sulfoxide, dimethylformamide (DMF), dimethylacetamide (DMA) and N-methylpyrrolidone (NMP), or else in water; particular preference is given to methylene chloride, THF and water.

It is also possible to use mixtures of the solvents mentioned.

Suitable bases are, in general, inorganic compounds, such as alkali metal and alkaline earth metal hydroxides, such as lithium hydroxide, sodium hydroxide, potassium hydroxide and calcium hydroxide, alkali metal and alkaline earth metal oxides, such as lithium oxide, sodium oxide, calcium oxide and magnesium oxide, alkali metal and alkaline earth metal hydrides, such as lithium hydride, sodium hydride, potassium hydride and calcium hydride, alkali metal and alkaline earth metal carbonates, such as lithium carbonate, potassium carbonate and calcium carbonate, and also alkali metal bicarbonates, such as sodium bicarbonate, moreover organic bases, for example tertiary amines, such as trimethylamine, triethylamine, diisopropylethylamine, N-methylmorpholine and N-methylpiperidine, pyridine, substituted pyridines, such as collidine, lutidine and 4-dimethylaminopyridine, and also bicyclic amines. Particular preference is given to sodium hydroxide, triethylamine and pyridine.

The bases are generally employed in equimolar amounts. However, they can also be used in excess or, if appropriate, as solvent.

The starting materials are generally reacted with one another in equimolar amounts. It may be advantageous to use an excess of IV, based on V.

The reaction mixtures are worked up in a customary manner, for example by mixing with water, separating the phases and, if appropriate, chromatographic purification of the crude products. Some of the intermediates and end products are obtained in the form of viscous oils which are purified or freed from volatile components under reduced pressure and at moderately elevated temperature. If the intermediates and end products are obtained as solids, purification can also be carried out by recrystallization or digestion.

The reaction of the serine derivatives of the formula V with heteroaryl acids/heteroaryl acid derivatives of the formula IV where $L^2$ is halogen, $C_1$-$C_6$-alkylcarbonyl, $C_1$-$C_6$-alkoxycarbonyl, $C_1$-$C_4$-alkylsulfonyl, phosphoryl or isoureyl to give heteroaroyl derivatives of the formula III is carried out in the presence of a base, usually at temperatures of from 0° C. to the boiling point of the reaction mixture, preferably at from 0° C. to 100° C., particularly preferably at room temperature, in an inert organic solvent [cf. Bergmann, E. D.; et al., J Chem Soc 1951, 2673; Zhdankin, V. V.; et al., Tetrahedron Lett. 2000, 41 (28), 5299-5302; Martin, S. F. et al., Tetrahedron Lett. 1998, 39 (12), 1517-1520; Jursic, B. S. et al., Synth Commun 2001, 31 (4), 555-564; Albrecht, M. et al., Synthesis 2001, (3), 468-472; Yadav, L. D. S. et al., Indian J. Chem B. 41(3), 593-595 (2002); Clark, J. E. et al., Synthesis (10), 891-894 (1991)].

Suitable solvents are aliphatic hydrocarbons, such as pentane, hexane, cyclohexane and mixtures of $C_5$-$C_8$-alkanes, aromatic hydrocarbons, such as benzene, toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran (THF), nitriles, such as acetonitrile and propionitrile, ketones, such as acetone, methyl ethyl ketone, diethyl ketone and tert-butyl methyl ketone, and also dimethyl sulfoxide, dimethylformamide (DMF), dimethylacetamide (DMA) and N-methylpyrrolidone (NMP), or else in water; particular preference is given to methylene chloride, THF and water.

It is also possible to use mixtures of the solvents mentioned.

Suitable bases are, in general, inorganic compounds, such as alkali metal and alkaline earth metal hydroxides, such as lithium hydroxide, sodium hydroxide, potassium hydroxide and calcium hydroxide, alkali metal and alkaline earth metal oxides, such as lithium oxide, sodium oxide, calcium oxide and magnesium oxide, alkali metal and alkaline earth metal hydrides, such as lithium hydride, sodium hydride, potassium hydride and calcium hydride, alkali metal and alkaline earth metal carbonates, such as lithium carbonate, potassium carbonate and calcium carbonate, and also alkali metal bicarbonates, such as sodium bicarbonate, moreover organic bases, for example tertiary amines, such as trimethylamine, triethylamine, diisopropylethylamine, N-methyl-morpholine and N-methylpiperidine, pyridine, substituted pyridines, such as collidine, lutidine and 4-dimethylaminopyridine, and also bicyclic amines. Particular preference is given to sodium hydroxide, triethylamine and pyridine.

The bases are generally employed in equimolar amounts. However, they can also be used in excess or, if appropriate, as solvent.

The starting materials are generally reacted with one another in equimolar amounts. It may be advantageous to use an excess of IV, based on V.

Work-up and isolation of the products can be carried out in a manner known per se.

It is, of course, also possible to initially react the serine derivatives of the formula V in an analogous manner with amines of the formula II to give the corresponding amides which are then reacted with heteroaryl acids/heteroaryl acid derivatives of the formula IV to give the desired heteroaroyl-substituted serineamides of the formula I.

The serine derivatives of the formula V (for example where $L^1$=hydroxyl or $C_1$-$C_6$-alkoxy) required for preparing the heteroaroyl derivatives of the formula III are known from the literature, even in enantiomerically and diastereomerically pure form, or they can be prepared in accordance with the literature cited:

- by condensation of glycine enolate equivalents with aldehydes or ketones [Blaser, D. et al., Liebigs Ann. Chem. 10, 1067-1078 (1991); Seethaler, T. et al., Liebigs Ann. Chem. 1, 11-17 (1991); Weltenauer, G. et al., Gazz. Chim. Ital. 81, 162 (1951); Dalla Croce, P. et al., Heterocycles 52(3), 1337-1344 (2000); Van der Werf, A. W. et al., J. Chem. Soc. Chem. Commun. 100, 682-683 (1991); Caddick, S. et al., Tetrahedron 57 (30), 6615-6626 (2001); Owa, T. et al., Chem. Lett. 1, 83-86 (1988); Alker, D. et al., Tetrahedron 54 (22), 6089-6098 (1998); Rousseau, J. F. et al., J. Org. Chem. 63 (8), 2731-2737 (1998); Saeed, A. et al., Tetrahedron 48 (12), 2507-2514 (1992); Dong, L. et al., J. Org. Chem. 67 (14), 4759-4770 (2002)].
- by aminohydroxylation of acrylic acid derivatives [Zhang, H. X. et al., Tetrahedron Asymmetr. 11 (16), 3439-3447 (2000); Fokin, V. V. et al., Angew. Chem. Int. Edit. 40(18), 3455 (2001); Sugiyama, H. et al., Tetrahedron Lett. 43(19), 3489-3492 (2002); Bushey, M. L. et al., J. Org. Chem. 64(9), 2984-2985 (1999); Raatz, D. et al., Synlett (12), 1907-1910 (1999)].
- by nucleophilic substitution of leaving groups in the 2-position of 3-hydroxypropionic acid derivatives [Owa, T. et al., Chem. Lett. (11), 1873-1874 (1988); Boger, D. L. et al., J. Org. Chem. 57(16), 4331-4333 (1992); Alcaide, B. et al., Tetrahedron Lett. 36(30), 5417-5420 (1995)].
- by condensation of aldehydes with nucleophiles with formation of oxazolines and subsequent hydrolysis [Evans, D. A. et al., Angew. Chem. Int. Edit. 40(10), 1884-1888 (2001); Ito, Y. et al., Tetrahedron Lett. 26(47), 5781-5784 (1985); Togni, A. et al., J. Organomet. Chem. 381 (1), C21-5 (1990); Longmire, J. M. et al., Organometallics 17(20), 4374-4379 (1998); Suga, H. et al., J. Org. Chem. 58(26), 7397-7405 (1993)].
- by oxidative cyclization of 2-acylamino-propionic acid derivatives to give oxazolines and subsequent hydrolysis (JP10101655).
- by Diels-Alder reactions of vinylimines with aldehydes to give the oxazines and subsequent hydrolysis [Bongini, A. et al., Tetrahedron Asym. 12(3), 439-454 (2001)].

The heteroaryl acids/heteroaryl acid derivatives of the formula IV required for preparing the heteroaroyl derivatives of the formula III are commercially available or can be prepared analogously to procedures known from the literature from the corresponding halide by a Grignard reaction [for example A. Mannschuk et al., Angew. Chem. 100, 299 (1988)].

The reaction of the heteroaroyl derivatives of the formula III where $L^1$=hydroxyl or salts thereof with amines of the formula II to give the desired heteroaroyl-substituted serineamides of the formula I is carried out in the presence of an activating reagent and, if appropriate, in the presence of a base, usually at temperatures of from 0° C. to the boiling point of the reaction mixture, preferably at from 0° C. to 100° C., particularly preferably at room temperature, in an inert organic solvent [cf. Perich, J. W., Johns, R. B., J. Org. Chem. 53 (17), 4103-4105 (1988); Somlai, C. et al., Synthesis (3), 285-287 (1992); Gupta, A. et al., J. Chem. Soc. Perkin Trans. 2, 1911 (1990); Guan et al., J. Comb. Chem. 2, 297 (2000)].

Suitable activating reagents are condensing agents, such as, for example, polystyrene-bound dicyclohexylcarbodiimide, diisopropylcarbodiimide, carbonyldiimidazole, chloroformic esters, such as methyl chloroformate, ethyl chloroformate, isopropyl chloroformate, isobutyl chloroformate, sec-butyl chloroformate or allyl chloroformate, pivaloyl chloride, polyphosphoric acid, propanephosphonic anhydride, bis(2-oxo-3-oxazolidinyl)phosphoryl chloride (BOPCl) or sulfonyl chlorides, such as methane-sulfonyl chloride, toluenesulfonyl chloride or benzenesulfonyl chloride.

Suitable solvents are aliphatic hydrocarbons, such as pentane, hexane, cyclohexane and mixtures of $C_5$-$C_8$-alkanes, aromatic hydrocarbons, such as benzene, toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran (THF), nitriles, such as acetonitrile and propionitrile, ketones, such as acetone, methyl ethyl ketone, diethyl ketone and tert-butyl methyl ketone, alcohols, such as methanol, ethanol, n-propanol, isopropanol, n-butanol and tert-butanol, and also dimethyl sulfoxide, dimethylformamide (DMF), dimethylacetamide (DMA) and N-methylpyrrolidone (NMP), or else in water; particular preference is given to methylene chloride, THF, methanol, ethanol and water.

It is also possible to use mixtures of the solvents mentioned.

Suitable bases are, in general, inorganic compounds, such as alkali metal and alkaline earth metal hydroxides, such as lithium hydroxide, sodium hydroxide, potassium hydroxide and calcium hydroxide, alkali metal and alkaline earth metal oxides, such as lithium oxide, sodium oxide, calcium oxide and magnesium oxide, alkali metal and alkaline earth metal hydrides, such as lithium hydride, sodium hydride, potassium hydride and calcium hydride, alkali metal and alkaline earth metal carbonates, such as lithium carbonate, potassium carbonate and calcium carbonate, and also alkali metal bicarbonates, such as sodium bicarbonate, moreover organic bases, for example tertiary amines, such as trimethylamine, triethylamine, diisopropylethylamine, N-methyl-morpholine and N-methylpiperidine, pyridine, substituted pyridines, such as collidine, lutidine and 4-dimethylaminopyridine, and also bicyclic amines. Particular preference is given to sodium hydroxide, triethylamine, ethyldiisopropylamine, N-methylmorpholine and pyridine.

The bases are generally employed in catalytic amounts; however, they can also be employed in equimolar amounts, in excess or, if appropriate, as solvent.

The starting materials are generally reacted with one another in equimolar amounts. It may be advantageous to use an excess of II, based on III.

Work-up and isolation of the products can be carried out in a manner known per se.

The reaction of the heteroaroyl derivatives of the formula III where $L^1=C_1$-$C_6$-alkoxy with amines of the formula II to give the desired heteroaroyl-substituted serineamides of the formula I is usually carried out at temperatures of from 0° C. to the boiling point of the reaction mixture, preferably from 0° C. to 100° C., particularly preferably at room temperature, in an inert organic solvent, if appropriate in the presence of a base [cf. Kawahata, N. H. et al., Tetrahedron Lett. 43 (40), 7221-7223 (2002); Takahashi, K. et al., J. Org. Chem. 50 (18), 3414-3415 (1985); Lee, Y. et al., J. Am. Chem. Soc. 121 (36), 8407-8408 (1999)].

Suitable solvents are aliphatic hydrocarbons, such as pentane, hexane, cyclohexane and mixtures of $C_5$-$C_8$-alkanes, aromatic hydrocarbons, such as benzene, toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran (THF), nitriles, such as acetonitrile and propionitrile, ketones, such as acetone, methyl ethyl ketone, diethyl ketone and tert-butyl methyl ketone, alcohols, such as methanol, ethanol, n-propanol, isopropanol, n-butanol and tert-butanol, and also dimethyl sulfoxide, dimethylformamide (DMF), dimethylacetamide (DMA) and N-methylpyrrolidone (NMP), or else in water; particular preference is given to methylene chloride, THF, methanol, ethanol and water.

It is also possible to use mixtures of the solvents mentioned.

If appropriate, the reaction can be carried out in the presence of a base. Suitable bases are, in general, inorganic compounds, such as alkali metal and alkaline earth metal hydroxides, such as lithium hydroxide, sodium hydroxide, potassium hydroxide and calcium hydroxide, alkali metal and alkaline earth metal oxides, such as lithium oxide, sodium oxide, calcium oxide and magnesium oxide, alkali metal and alkaline earth metal hydrides, such as lithium hydride, sodium hydride, potassium hydride and calcium hydride, alkali metal and alkaline earth metal carbonates, such as lithium carbonate, potassium carbonate and calcium carbonate, and also alkali metal bicarbonates, such as sodium bicarbonate, moreover organic bases, for example tertiary amines, such as trimethylamine, triethylamine, diisopropylethylamine, N-methyl-morpholine and N-methylpiperidine, pyridine, substituted pyridines, such as collidine, lutidine and 4-dimethylaminopyridine, and also bicyclic amines. Particular preference is given to sodium hydroxide, triethylamine, ethyldiisopropylamine, N-methylmorpholine and pyridine.

The bases are generally employed in catalytic amounts; however, they can also be employed in equimolar amounts, in excess or, if appropriate, as solvent.

The starting materials are generally reacted with one another in equimolar amounts. It may be advantageous to use an excess of II, based on III.

Work-up and isolation of the products can be carried out in a manner known per se.

The amines of the formula II required for preparing the heteroaroyl-substituted serineamides of the formula I are commercially available.

Process B

Heteroaroyl derivatives of the formula III where $R^4$=hydrogen can also be obtained by condensing acylated glycine derivatives of the formula VIII where the acyl group may be a cleavable protective group, such as benzyloxycarbonyl (cf. VIIIa where $\Sigma$=benzyl) or tert-butyloxycarbonyl (cf. VIIIa where $\Sigma$=tert-butyl), with carbonyl compounds VII to give the corresponding aldol products VI. The protective group is then cleaved and the resulting serine derivative of the formula V where $R^4$=hydrogen is acylated using heteroaryl acid derivatives of the formula IV.

Analogously, it is also possible to convert an acylated glycine derivative of the formula VIII where the acyl group is a substituted heteroaryl radical (cf. VIIIb) in the presence of a base with a carbonyl compound VII into the heteroaroyl derivative III where $R^4$=hydrogen:

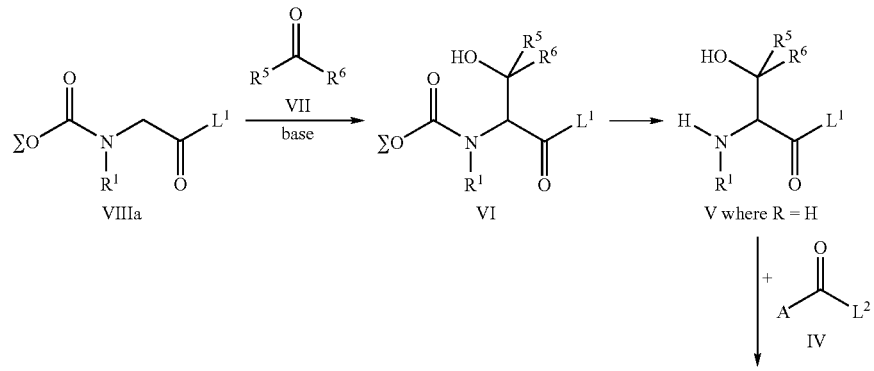

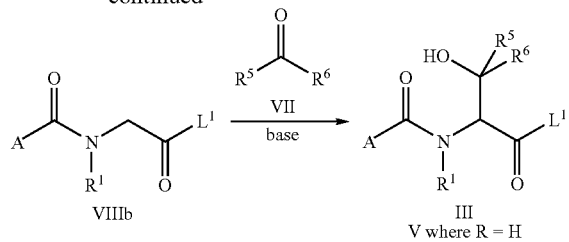

$L^1$ is a nucleophilically displaceable leaving group, for example hydroxyl or $C_1$-$C_6$-alkoxy.

$L^2$ is a nucleophilically displaceable leaving group, for example hydroxyl, halogen, $C_1$-$C_6$-alkylcarbonyl, $C_1$-$C_6$-alkoxycarbonyl, $C_1$-$C_4$-alkylsulfonyl, phosphoryl or isoureyl.

The reaction of the glycine derivatives VIII with carbonyl compounds VII to give the corresponding aldol product VI or heteroaroyl derivative III where $R^4$=hydrogen is usually carried out at temperatures of from –100° C. to the boiling point of the reaction mixture, preferably at from –80° C. to 20° C., particularly preferably at from –80° C. to –20° C., in an inert organic solvent in the presence of a base [cf. J.-F. Rousseau et al., J. Org. Chem. 63, 2731-2737 (1998)].

Suitable solvents are aliphatic hydrocarbons, such as pentane, hexane, cyclohexane and mixtures of $C_5$-$C_8$-alkanes, aromatic hydrocarbons, such as toluene, o-, m- and p-xylene, ethers, such as diethyl ether, diisopropyl ether, tert-butyl methyl ether, dioxane, anisole and tetrahydrofuran, and also dimethyl sulfoxide, dimethylformamide and dimethylacetamide, particularly preferably diethyl ether, dioxane and tetrahydrofuran.

It is also possible to use mixtures of the solvents mentioned.

Suitable bases are, in general, inorganic compounds, such as alkali metal and alkaline earth metal hydrides, such as lithium hydride, sodium hydride, potassium hydride and calcium hydride, alkali metal azides, such as lithium diisopropylamide, lithium hexamethyldisilazide, organometallic compounds, in particular alkali metal alkyls, such as methyllithium, butyllithium and phenyllithium, and also alkali metal and alkaline earth metal alkoxides, such as sodium methoxide, sodium ethoxide, potassium ethoxide, potassium tert-butoxide, potassium tert-pentoxide and dimethoxymagnesium, moreover organic bases, for example tertiary amines, such as trimethylamine, triethylamine, diisopropylethylamine and N-methylpiperidine, pyridine, substituted pyridines, such as collidine, lutidine and 4-dimethylaminopyridine, and also bicyclic amines. Particular preference is given to sodium hydride, lithium hexamethyldisilazide and lithium diisopropylamide.

The bases are generally employed in equimolar amounts; however, they can also be used catalytically, in excess or, if appropriate, as solvents.

The starting materials are generally reacted with one another in equimolar amounts. It may be advantageous to employ an excess of base and/or carbonyl compounds VII, based on the glycine derivatives VIII.

Work-up and isolation of the products can be carried out in the manner known per se.

The glycine derivatives of the formula VIII required for preparing the compounds I are commercially available, known from the literature [for example H. Pessoa-Mahana et al., Synth. Comm. 32, 1437 (2002)] or can be prepared in accordance with the literature cited.

The protective group is cleaved off by methods known from the literature, giving serine derivatives of the formula V where $R^4$=hydrogen [cf. J.-F. Rousseau et al., J. Org. Chem. 63, 2731-2737 (1998); J. M. Andres, Tetrahedron 56, 1523 (2000)]; in the case of Σ=benzyl by hydrogenolysis, preferably using hydrogen and Pd/C in methanol; in the case of Σ=tert-butyl using acid, preferably hydrochloric acid in dioxane.

The reaction of the serine derivatives V where $R^4$=hydrogen with heteroaryl acids/heteroaryl acid derivatives IV where $R^4$=hydrogen to give heteroaroyl derivatives III where $R^4$=hydrogen is usually carried out analogously to the reaction of the serine derivatives of the formula V with heteroaryl acids/heteroaryl acid derivatives of the formula III to give heteroaroyl derivatives III mentioned in process A.

Analogously to process A, the heteroaroyl derivatives of the formula III where $R^4$=hydrogen can then be reacted with amines of the formula II to give the desired heteroaroyl-substituted serineamides of the formula I where $R^4$=hydrogen which can then be derivatized with compounds of the formula IX to give heteroaroyl-substituted serineamides of the formula I [cf., for example, Yokokawa, F. et al., Tetrahedron Lett. 42 (34), 5903-5908 (2001); Arrault, A. et al., Tetrahedron Lett. 43 (22), 4041-4044 (2002)].

It is also possible to derivatize the heteroaroyl derivatives of the formula III where $R^4$=hydrogen initially with compounds of the formula IX to give further heteroaroyl derivatives of the formula III [cf., for example, Troast, D. et al., Org. Lett. 4 (6), 991-994 (2002); Ewing W. et al., Tetrahedron Lett., 30 (29), 3757-3760 (1989); Paulsen, H. et al., Liebigs Ann. Chem. 565 (1987)], followed by reaction with amines of the formula II analogously to process A, giving the desired heteroaroyl-substituted serineamides of the formula I:

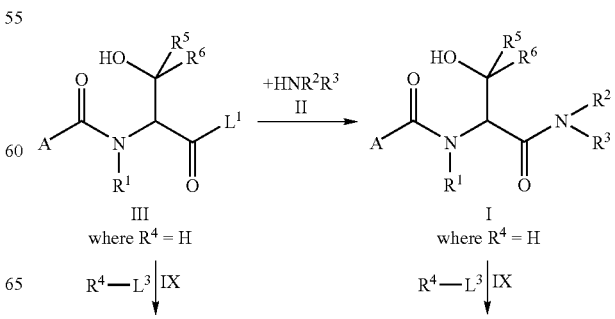

-continued

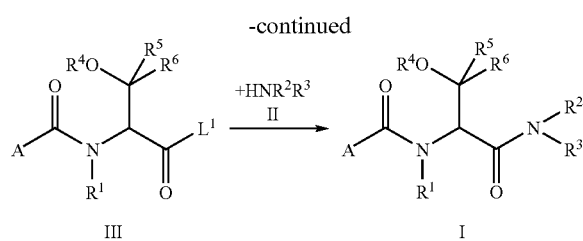

$L^1$ is a nucleophilically displaceable leaving group, for example hydroxyl or $C_1$-$C_6$-alkoxy.

$L^3$ is a nucleophilically displaceable leaving group, for example halogen, hydroxyl, or $C_1$-$C_6$-alkoxy.

The reaction of the heteroaroyl derivatives of the formula III (where, if appropriate, $R^4$=hydrogen) with amines of the formula II to give heteroaroyl-substituted serineamides of the formula I (where, if appropriate, $R^4$=hydrogen) is usually carried out analogously to the reaction of the heteroaroyl derivatives of the formula III with amines of the formula II described in process A.

The reaction of the heteroaroyl derivatives of the formula III where $R^4$=hydrogen or of the heteroaroyl-substituted serineamides of the formula I where $R^4$=hydrogen with compounds of the formula IX to give heteroaroyl derivatives of the formula III or heteroaroyl-substituted serineamides of the formula I is usually carried out at temperatures of from 0° C. to 100° C., preferably from 10° C. to 50° C., in an inert organic solvent in the presence of a base [cf., for example, Troast, D. et al., Org. Lett. 4 (6), 991-994 (2002); Ewing W. et al., Tetrahedron Lett., 30 (29), 3757-3760 (1989); Paulsen, H. et al., Liebigs Ann. Chem. 565 (1987)].

Suitable solvents are aliphatic hydrocarbons, such as pentane, hexane, cyclohexane and mixtures of $C_5$-$C_8$-alkanes, aromatic hydrocarbons, such as toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran, nitriles, such as acetonitrile and propionitrile, ketones, such as acetone, methyl ethyl ketone, diethyl ketone and tert-butyl methyl ketone, alcohols, such as methanol, ethanol, n-propanol, isopropanol, n-butanol and tert-butanol, and also dimethyl sulfoxide, dimethylformamide and dimethylacetamide, particularly preferably dichloromethane, tert-butyl methyl ether, dioxane and tetrahydrofuran.

It is also possible to use mixtures of the solvents mentioned.

Suitable bases are, in general, inorganic compounds, such as alkali metal and alkaline earth metal hydroxides, such as lithium hydroxide, sodium hydroxide, potassium hydroxide and calcium hydroxide, alkali metal and alkaline earth metal oxides, such as lithium oxide, sodium oxide, calcium oxide and magnesium oxide, alkali metal and alkaline earth metal hydrides, such as lithium hydride, sodium hydride, potassium hydride and calcium hydride, alkali metal amides, such as lithium amide, sodium amide and potassium amide, alkali metal and alkaline earth metal carbonates, such as lithium carbonate, potassium carbonate and calcium carbonate, and also alkali metal bicarbonates, such as sodium bicarbonate, organometallic compounds, in particular alkali metal alkyls, such as methyllithium, butyllithium and phenyllithium, alkylmagnesium halides, such as methylmagnesium chloride, and also alkali metal and alkaline earth metal alkoxides, such as sodium methoxide, sodium ethoxide, potassium ethoxide, potassium tert-butoxide, potassium tert-pentoxide and dimethoxymagnesium, moreover organic bases, for example tertiary amines, such as trimethylamine, triethylamine, diisopropylethylamine and N-methylpiperidine, pyridine, substituted pyridines, such as collidine, lutidine and 4-dimethylaminopyridine, and also bicyclic amines. Particular preference is given to sodium hydroxide, sodium hydride and triethylamine.

The bases are generally employed in equimolar amounts; however, they can also be employed catalytically, in excess or, if appropriate, as solvents.

The starting materials are generally reacted with one another in equimolar amounts. It may be advantageous to use an excess of base and/or IX, based on III or I.

Work-up and isolation of the products can be carried out in a manner known per se.

The required compounds of the formula VIII are commercially available.

Process C

Heteroaroyl derivatives of the formula III where $R^4$=hydrogen can also be obtained by initially acylating aminomalonyl compounds of the formula XI with heteroaryl acids/heteroaryl acid derivatives of the formula IV to give the corresponding N-acyl-aminomalonyl compounds of the formula X, followed by condensation with a carbonyl compound of the formula VII with decarboxylation:

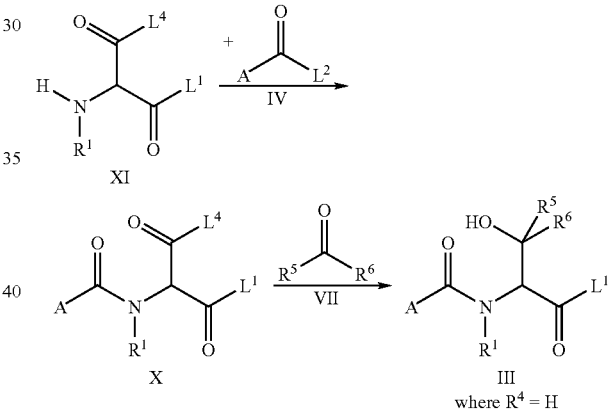

$L^1$ is a nucleophilically displaceable leaving group, for example hydroxyl or $C_1$-$C_6$-alkoxy.

$L^2$ is a nucleophilically displaceable leaving group, for example hydroxyl, halogen, $C_1$-$C_6$-alkylcarbonyl, $C_1$-$C_6$-alkoxycarbonyl, $C_1$-$C_6$-alkylsulfonyl, phosphoryl or isoureyl.

$L^4$ is a nucleophilically displaceable leaving group, for example hydroxyl or $C_1$-$C_6$-alkoxy.

The acylation of the aminomalonyl compounds of the formula XI with heteroaryl acids/heteroaryl acid derivatives of the formula IV to give the corresponding N-acyl-aminomalonyl compounds of the formula X is usually carried out analogously to the reaction, mentioned in process A, of the serine derivatives of the formula V with heteroaryl acids/heteroaryl acid derivatives of the formula IV to give the corresponding heteroaroyl derivatives of the formula III.

The reaction of the N-acylaminomalonyl compounds of the formula X with carbonyl compounds of the formula VII give heteroaroyl derivatives of the formula III where $R^4$=hydrogen is usually carried out at temperatures of from 0° C. to 100° C., preferably from 10° C. to 50° C., in an inert organic solvent in the presence of a base [cf., for example, U.S. Pat. No. 4,904,674; Hellmann, H. et al., Liebigs Ann. Chem. 631, 175-179 (1960)].

If $L^4$ in the N-acylaminomalonyl compounds of the formula X is $C_1$-$C_6$-alkoxy, it is advantageous to initially convert $L^4$ by ester hydrolysis [for example Hellmann, H. et al., Liebigs Ann. Chem. 631, 175-179 (1960)] into a hydroxyl group.

Suitable solvents are aliphatic hydrocarbons, such as pentane, hexane, cyclohexane and mixtures of $C_5$-$C_8$-alkanes, aromatic hydrocarbons, such as toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran, nitriles, such as acetonitrile and propionitrile, ketones, such as acetone, methyl ethyl ketone, diethyl ketone and tert-butyl methyl ketone, alcohols, such as methanol, ethanol, n-propanol, isopropanol, n-butanol and tert-butanol, and also dimethyl sulfoxide, dimethylformamide and dimethylacetamide, particularly preferably diethyl ether, dioxane and tetrahydrofuran.

It is also possible to use mixtures of the solvents mentioned.

Suitable bases are, in general, inorganic compounds, such as alkali metal and alkaline earth metal hydroxides, such as lithium hydroxide, sodium hydroxide, potassium hydroxide and calcium hydroxide, alkali metal and alkaline earth metal oxides, such as lithium oxide, sodium oxide, calcium oxide and magnesium oxide, alkali metal and alkaline earth metal hydrides, such as lithium hydride, sodium hydride, potassium hydride and calcium hydride, alkali metal amides, such as lithium amide, sodium amide and potassium amide, alkali metal and alkaline earth metal carbonates, such as lithium carbonate, potassium carbonate and calcium carbonate, and also alkali metal bicarbonates, such as sodium bicarbonate, organometallic compounds, in particular alkali metal alkyls, such as methyllithium, butyllithium and phenyllithium, alkylmagnesium halides, such as methylmagnesium chloride, and also alkali metal and alkaline earth metal alkoxides, such as sodium methoxide, sodium ethoxide, potassium ethoxide, potassium tert-butoxide, potassium tert-pentoxide and dimethoxymagnesium, moreover organic bases, for example tertiary amines, such as trimethylamine, triethylamine, diisopropylethylamine and N-methylpiperidine, pyridine, substituted pyridines, such as collidine, lutidine and 4-dimethylaminopyridine, and also bicyclic amines. Particular preference is given to triethylamine and diisopropylethylamine.

The bases are generally employed in catalytic amounts; however, they can also be used in equimolar amounts, in excess or, if appropriate, as solvents.

The starting materials are generally reacted with one another in equimolar amounts. It may be advantageous to employ an excess of base, based on X.

Work-up and isolation of the products can be carried out in a manner known per se.

According to the process A or B mentioned above, the resulting heteroaryl derivatives of the formula III where $R^4$=hydrogen can then be converted into the desired heteroaroyl-substituted serineamides of the formula I.

The required aminomalonyl compounds of the formula XI are commercially available and/or known from the literature [for example U.S. Pat. No. 4,904,674; Hellmann, H. et al., Liebigs Ann. Chem. 631, 175-179 (1960)], or they can be prepared in accordance with the literature cited.

The required heterocyclic compounds of the formula VII are commercially available.

Process D

Heteroaroyl derivatives of the formula III where $R^4$ and $R^5$=hydrogen can also be obtained by initially reducing keto compounds of the formula XIII with heteroaryl acids/heteroaryl acid derivatives of the formula IV to give the corresponding N-acyl keto compounds of the formula XII, followed by reduction of the keto group [Girard A, Tetrahedron Lett. 37 (44), 7967-7970 (1996); Nojori R., J. Am. Chem. Soc. 111 (25), 9134-9135 (1989); Schmidt U., Synthesis (12), 1248-1254 (1992); Bolhofer, A.; J. Am. Chem. Soc. 75, 4469 (1953)]:

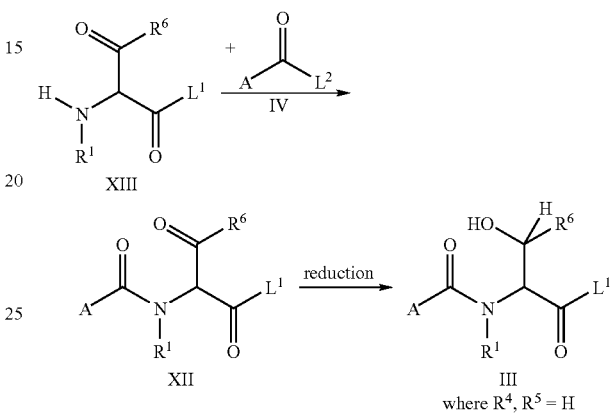

$L^1$ is a nucleophilically displaceable leaving group, for example hydroxyl or $C_1$-$C_6$-alkoxy.

$L^2$ is a nucleophilically displaceable leaving group, for example hydroxyl, halogen, $C_1$-$C_6$-alkylcarbonyl, $C_1$-$C_6$-alkoxycarbonyl, $C_1$-$C_6$-alkylsulfonyl, phosphoryl or isoureyl.

The acylation of the keto compounds of the formula XIII with heteroaryl acids/heteroaryl acid derivatives of the formula IV to give N-acyl keto compounds of the formula XIII is usually carried out analogously to the reaction, mentioned in process A, of the serine derivatives of the formula V with heteroaryl acids/heteroaryl acid derivatives of the formula IV to give the corresponding heteroaroyl derivatives of the formula III.

The keto compounds of the formula XIII required for preparing the heteroaroyl derivatives of the formula III where $R^4$ and $R^5$=hydrogen are known from the literature [WO 02/083111; Boto, A. et al., Tetrahedron Letters 39 (44), 8167-8170 (1988); von Geldern, T. et al., J. of Med. Chem. 39(4), 957-967 (1996); Singh, J. et al., Tetrahedron Letters 34 (2), 211-214 (1993); ES 2021557; Maeda, S: et al., Chem. & Pharm. Bull. 32 (7), 2536-2543 (1984); Ito, S. et al., J. of Biol. Chem. 256 (15), 7834-4783 (1981); Vinograd, L. et al., Zhurnal Organicheskoi Khimii 16 (12), 2594-2599 (1980); Castro, A. et al., J. Org. Chem. 35 (8), 2815-2816 (1970); JP 02-172956; Suzuki, M. et al., J. Org. Chem. 38 (20), 3571-3575 (1973); Suzuki, M. et al, Synthetic Communications 2 (4), 237-242 (1972)] or can be prepared according to the literature cited.

The reduction of the N-acyl keto compounds of the formula XII to heteroaroyl derivatives of the formula III where $R^4$ and $R^5$=hydrogen is usually carried out at temperatures of from 0° C. to 100° C., preferably from 20° C. to 80° C., in an inert organic solvent in the presence of a reducing agent.

Suitable solvents are aliphatic hydrocarbons, such as pentane, hexane, cyclohexane and mixtures of $C_5$-$C_8$-alkanes, aromatic hydrocarbons, such as toluene, o—, m—and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran, nitriles, such as acetonitrile and propionitrile, ketones, such as acetone, methyl ethyl ketone, diethyl ketone and tert-butyl methyl ketone, alcohols, such as methanol, ethanol, n-propanol, isopropanol, n-butanol and tert-butanol, and also dimethyl sulfoxide, dimethyl formamide and dimethyl acetamide, particularly preferably toluene, methylene chloride or tert-butyl methyl ether.

It is also possible to use mixtures of the solvents mentioned.

Suitable reducing agents are, for example, sodium borohydride, zinc borohydride, sodium cyanoborohydride, lithium triethylborohydride (Superhydrid®), lithium tri-sec-butyl-borohydride (L-Selectrid®), lithium aluminum hydride or borane [cf., for example, WO 00/20424; Marchi, C. et al., Tetrahedron 58 (28), 5699 (2002); Blank, S. et al., Liebigs Ann. Chem. (8), 889-896 (1993); Kuwano, R. et al., J. Org. Chem. 63 (10), 3499-3503 (1998); Clariana, J. et al., Tetrahedron 55 (23), 7331-7344 (1999)].

Furthermore, the reduction can also be carried out in the presence of hydrogen and a catalyst. Suitable catalysts are, for example, [Ru(BINAP)Cl$_2$] or Pd/C [cf. Noyori, R. et al., J. Am. Chem. Soc. 111 (25), 9134-9135 (1989); Bolhofer, A. et al., J. Am. Chem. Soc. 75, 4469 (1953)].

In addition, the reduction can also be carried out in the presence of a microorganism. The suitable microorganism is, for example, *Saccharomyces rouxii* [cf. Soukup, M. et al., Helv. Chim. Acta 70, 232 (1987)].

The N-acyl keto compounds of the formula XII and the reducing agent in question are generally reacted with one another in equimolar amounts. It may be advantageous to employ an excess of reducing agent, based on XII.

Work-up and isolation of the products can be carried out in the manner known per se.

The resulting heteroaroyl derivatives of the formula III where $R^4$ and $R^5$=hydrogen can then, according to the processes A and B mentioned above, be converted into the desired heteroaroyl-substituted serineamides of the formula I.

Process E

Heteroaroyl derivatives of the formula III where $R^4$=hydrogen and $R^6$=—C(OH)R'R" can also be obtained by dihydroxylating vinylglycines of the formula XIV with an oxidizing agent such as osmium tetroxide or permanganate:

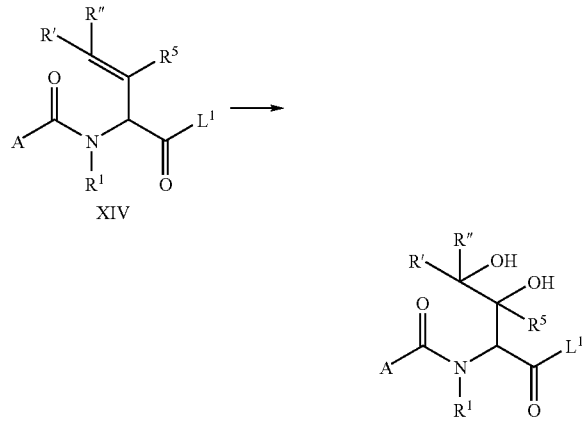

where $R^4$ = H and $R^6$ = ——C(OH)R'R"

$L^1$ is a nucleophilically displaceable leaving group, for example hydroxyl or $C_1$-$C_6$-alkoxy.

R' is hydrogen, $C_1$-$C_6$-alkyl, $C_1$-$C_6$-haloalkyl, $C_1$-$C_6$-hydroxyalkyl, phenyl or $C_1$-$C_6$-alkoxycarbonyl.

R" is hydrogen, $C_1$-$C_6$-alkyl, $C_1$-$C_6$-haloalkyl, $C_1$-$C_6$-hydroxyalkyl, phenyl or $C_1$-$C_6$-alkoxycarbonyl.

This reaction is usually carried out at temperatures of from −78° C. to the boiling point of the reaction mixture, preferably from −10° C. to 120° C., particularly preferably from 0° C. to 50° C., in an inert organic solvent, if appropriate in the presence of a reoxidazing agent, such as, for example, N-methylmorpholine N-oxide (D. Johnson et al., Tetrahedron 2000, 56, 5, 781).

Suitable solvents are halogenated hydrocarbons, such as methylene chloride, chloroform and chlorobenzene, ethers, such as diethyl ether, diisopropyl ether, tert-butyl methyl ether, dioxane, anisole and tetrahydrofuran, nitriles, such as acetonitrile and propionitrile, ketones, such as acetone, methyl ethyl ketone, diethyl ketone and tert-butyl methyl ketone, alcohols, such as methanol, ethanol, n-propanol, isopropanol, n-butanol and tert.-butanol, and also dimethyl sulfoxide, dimethylformamide, dimethylacetamide and water; particularly preferably acetone or water.

It is also possible to use mixtures of the solvents mentioned.

The starting materials are generally reacted with one another in equimolar amounts. It may be advantageous to employ an excess of oxidizing agent, based on XIV.

The reaction mixtures are worked up in a customary manner, for example by mixing with water, separation of the phases and, if required, chromatographic purification of the crude products. Some of the intermediates and end products are obtained in the form of viscous oils which are purified or freed from volatile components under reduced pressure and at moderately elevated temperature. If the intermediates and end products are obtained as solids, purification may also be carried out by recrystallization or digestion.

The vinylglycines of the formula XIV required for preparing the heteroaroyl derivatives of the formula III where $R^4$=hydrogen and $R^6$=—C(OH)R'R" are known from the literature [D. B. Berkowitz et al., J. Org. Chem. 2000, 65, 10, 2907; M. Koen et al., J. Chem. Soc. Perkin I 1997, 4, 487] or can be prepared in accordance to the literature cited.

Analogously to process A, the heteroaroyl derivatives of the formula III where $R^4$=hydrogen and $R^6$=—C(OH)R'R" can then be reacted with amines of the formula II to give the desired heteroaroyl-substituted serineamides of the formula I where $R^4$=hydrogen and $R^6$=—C(OH)R'R", which can then be derivatized with compounds of the formula IX to give heteroaroyl-substituted serineamides of the formula I where $R^6$=—C(OR$^4$)R'R" [cf., for example, Yokokawa, F. et al., Tetrahedron Lett. 42 (34), 5903-5908 (2001); Arrault, A. et al., Tetrahedron Lett. 43(22), 4041-4044 (2002)];

also, the heteroaroyl derivatives of the formula III where $R^4$=hydrogen can initially be derivatized analogously to process B with compounds of the formula IX to give further heteroaroyl derivatives of the formula III where $R^6$=—C(OR$^4$)R'R" [cf., for example, Troast, D. et al., Org. Lett. 4 (6), 991-994 (2002); Ewing W. et al., Tetrahedron Lett., 30 (29), 3757-3760 (1989); Paulsen, H. et al., Liebigs Ann. Chem. 565 (1987)] and then be reacted analogously to process A with amines of the formula II to give the desired heteroaroyl-substituted serineamides of the formula I where $R^6$=—C(OR$^4$)R'R":

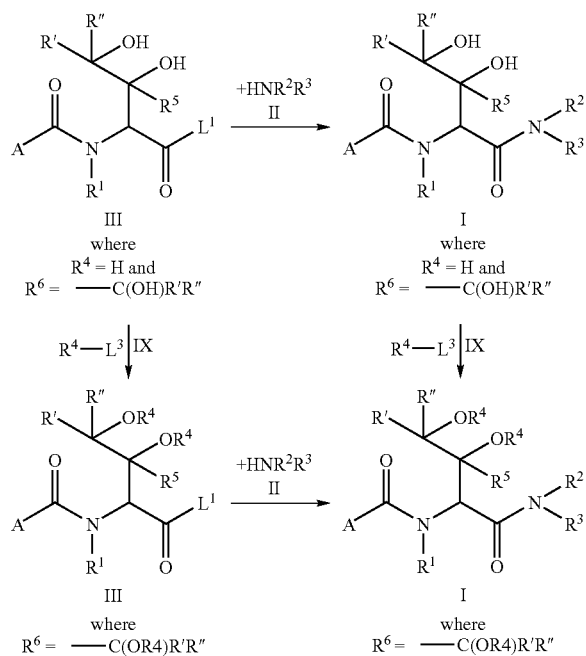

$L^1$ is a nucleophilically displaceable leaving group, for example hydroxyl or $C_1$-$C_6$-alkoxy.

$L^3$ is a nucleophilically displaceable leaving group, for example halogen, hydroxyl or $C_1$-$C_6$-alkoxy.

R' is hydrogen, $C_1$-$C_6$-alkyl, $C_1$-$C_6$-haloalkyl, $C_1$-$C_6$-hydroxyalkyl, phenyl or $C_1$-$C_6$-alkoxycarbonyl.

R" is hydrogen, $C_1$-$C_6$-alkyl, $C_1$-$C_6$-haloalkyl, $C_1$-$C_6$-hydroxyalkyl, phenyl or $C_1$-$C_6$-alkoxycarbonyl.

Process F

Heteroaroyl derivatives of the formula III where $R^4$=hydrogen and $R^6$=—C(Nuc)R'R" can also be obtained by epoxidizing vinylglycines of the formula XIV with an epoxidizing agent to give epoxyglycines of the formula XV, followed by nucleophilic opening of the epoxide:

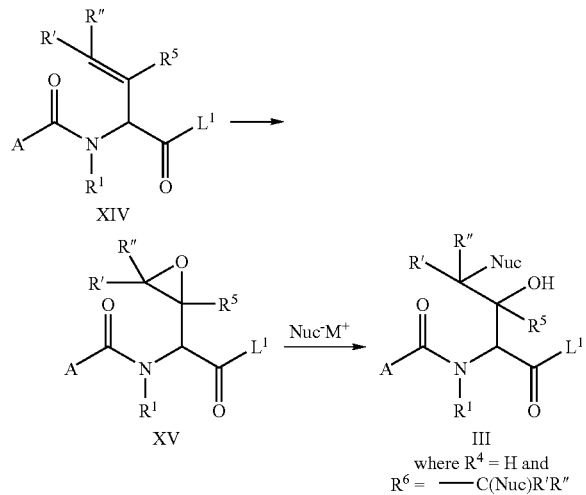

$L^1$ is a nucleophilically displaceable leaving group, for example hydroxyl or $C_1$-$C_6$-alkoxy.

R' is hydrogen, $C_1$-$C_6$-alkyl, $C_1$-$C_6$-haloalkyl, $C_1$-$C_6$-hydroxyalkyl, phenyl or $C_1$-$C_6$-alkoxycarbonyl.

R" is hydrogen, $C_1$-$C_6$-alkyl, $C_1$-$C_6$-haloalkyl, $C_1$-$C_6$-hydroxyalkyl, phenyl or $C_1$-$C_6$-alkoxycarbonyl.

$Nuc^-M^+$ is, for example, a thiolate, such as, for example, sodium thiophenolate, an alcoxide, such as potassium phenoxide, or an amide, such as sodium imidazolate.

The epoxidation is usually carried out at temperatures of from −78° C. to the boiling point of the reaction mixture, preferably from −20° C. to 50° C., in particular from 0° C. to 30° C., in an inert organic solvent [cf. P. Meffre et al., Tetrahedron Lett. 1990, 31, 16, 2291].

Suitable epoxidizings agent are peracids and peroxides (for example meta-chloroperbenzoic acid, peracetic acid, dimethyldioxirane, hydrogen peroxide).

Suitable solvents are halogenated hydrocarbons, such as methylene chloride, chloroform and chlorobenzene, alcohols, such as methanol, ethanol, n-propanol, isopropanol, n-butanol and tert-butanol, and also water, particularly preferably halogenated hydrocarbons and water.

It is also possible to use mixtures of the solvents mentioned.

The starting materials are generally reacted with one another in equimolar amounts. It may be advantageous to employ an excess of epoxidizing agent, based on XIV.

The reaction mixtures are worked up in a customary manner, for example by mixing with water, separation of the phases and, if required, chromatographic purification of the crude products. Some of the intermediates and end products are obtained in the form of viscous oils which are purified or freed from volatile components under reduced pressure and at moderately elevated temperature. If the intermediates and end products are obtained as solids, purification may also be carried out by recrystallization or digestion.

The vinylglycines of the formula XIV required for preparing the heteroaroyl derivatives of the formula III where $R^4$=hydrogen and $R^6$=—C(OH)R'R" are known from the literature [D. B. Berkowitz et al., J. Org. Chem. 2000, 65, 10, 2907; M. Koen et al., J. Chem. Soc. Perkin I 1997, 4, 487] or can be prepared in accordance with the literature cited.

The opening of the epoxide is usually carried out at temperatures of from −78° C. to the boiling point of the reaction mixture, preferably from −20° C. to 100° C., particularly preferably from 0° C. to 50° C., in an inert organic solvent, if appropriate in the presence of a catalyst [cf. P. Meffre et al., Tetrahedron Lett. 1990, 31, 16, 2291; M. R. Paleo et al., J. Org. Chem. 2003, 68, 1, 130].

Suitable solvents are alcohols, such as methanol, ethanol, n-propanol, isopropanol, n-butanol and tert-butanol, and also dimethyl sulfoxide, dimethylformamide and dimethylacetamide and water, particularly preferably methanol and water.

It is also possible to use mixtures of the solvents mentioned.

Suitable acid catalysts are Lewis acids, such as boron trifluoride, aluminum trichloride, iron(III) chloride, tin(IV) chloride, titanium(IV) chloride, zinc(II) chloride and magnesium perchlorate.

The catalyst is usually employed in an amount of from 1 to 100 mol %, preferably from 1 to 10 mol %, based on the compound XV.

The starting materials are generally reacted with one another in equimolar amounts. It may be advantageous to employ an excess of $Nuc^-M^+$, based on XV.

The reaction mixtures are worked up in a customary manner, for example by mixing with water, separation of the phases and, if required, chromatographic purification of the crude products. Some of the intermediates and end products are obtained in the form of viscous oils which are purified or freed from volatile components under reduced pressure and at moderately elevated temperature. If the intermediates and end products are obtained as solids, purification may also be carried out by recrystallization or digestion.

Analogously to process A, the heteroaroyl derivatives of the formula III where $R^4$=hydrogen and $R^6$=—C(Nuc)R'R" can then be reacted with amines of the formula II to give the desired benzoyl-substituted serineamides of the formula I where $R^4$=hydrogen and $R^6$=—C(Nuc)R'R", which can then be derivatized with compounds of the formula IX to give heteroaroyl-substituted serineamides of the formula I where $R^6$=—C(OR$^4$)R'R" [cf., for example, Yokokawa, F. et al., Tetrahedron Lett. 42 (34), 5903-5908 (2001); Arrault, A. et al., Tetrahedron Lett. 43(22), 4041-4044 (2002)];

also, the heteroaroyl derivatives of the formula III where $R^4$=hydrogen can initially be derivatized analogously to process B with compounds of the formula IX to give further benzoyl derivatives of the formula III where $R^6$=—C(Nuc) R'R" [cf., for example, Troast, D. et al., Org. Lett. 4 (6), 991-994 (2002); Ewing W. et al., Tetrahedron Lett., 30 (29), 3757-3760 (1989); Paulsen, H. et al., Liebigs Ann. Chem. 565 (1987)] and then be reacted analogously to process A with amines of the formula II to give the desired heteroaroyl-substituted serineamides of the formula I where $R^6$=—C (Nuc)R'R":

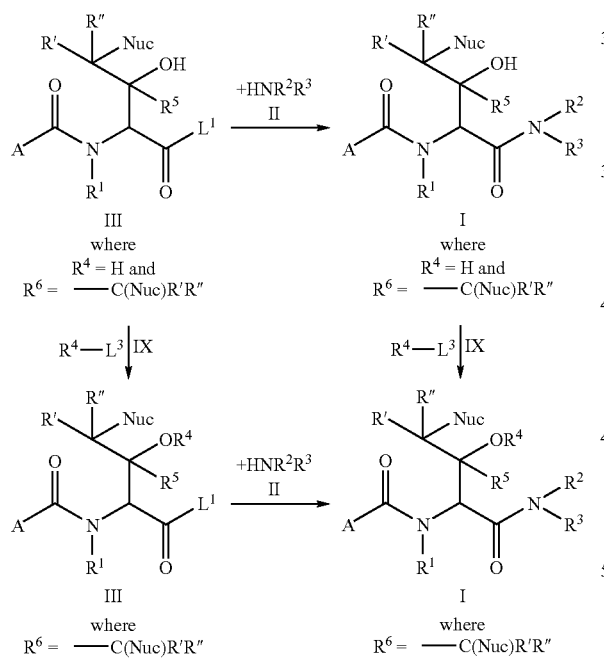

$L^1$ is a nucleophilically displaceable leaving group, for example hydroxyl or $C_1$-$C_6$-alkoxy.

$L^3$ is a nucleophilically displaceable leaving group, for example halogen, hydroxyl or $C_1$-$C_6$-alkoxy.

R' is hydrogen, $C_1$-$C_6$-alkyl, $C_1$-$C_6$-haloalkyl, $C_1$-$C_6$-hydroxyalkyl, phenyl or $C_1$-$C_6$-alkoxycarbonyl.

R" is hydrogen, $C_1$-$C_6$-alkyl, $C_1$-$C_6$-haloalkyl, $C_1$-$C_6$-hydroxyalkyl, phenyl or $C_1$-$C_6$-alkoxycarbonyl.

Nuc$^-$M$^+$ is, for example, a thiolate, such as, for example, sodium thiophenolate, an alcoxide, such as potassium phenoxide, or an amide, such as sodium imidazolate.

The present invention also provides heteroaroyl derivatives of the formula III

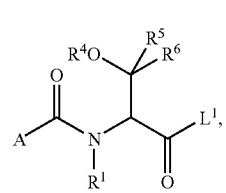

where A, $R^1$ and $R^4$, $R^5$ and R' are as defined above and $L^1$ is hydroxyl or $C_1$-$C_6$-alkoxy.

The particularly preferred embodiments of the intermediates with respect to the variables correspond to those of the radicals A, $R^1$ and $R^4$ to $R^6$ of the formula I.

Particular preference is given to heteroaroyl derivatives of the formula III in which A is 5- or 6-membered heteroaryl selected from the group consisting of thienyl, furyl, pyrazolyl, imidazolyl, thiazolyl, oxazolyl and pyridyl; where the
heteroaryl radicals mentioned may be partially or fully halogenated and/or may carry 1 to 3 radicals from the group consisting of $C_1$-$C_6$-alkyl, $C_3$-$C_6$-cycloalkyl and $C_1$-$C_6$-haloalkyl;

$R^1$ is hydrogen;

$R^4$ is hydrogen, formyl, $C_1$-$C_4$-alkylcarbonyl, $C_1$-$C_4$-alkylaminocarbonyl, di-($C_1$-$C_4$-alkyl)-aminocarbonyl, phenylaminocarbonyl, N—($C_1$-$C_4$-alkyl)-N-(phenyl)aminocarbonyl, $SO_2CH_3$, $SO_2CF_3$ or $SO_2(C_6H_5)$;

$R^5$ is hydrogen; and $R^6$ is $C_1$-$C_6$-alkyl, $C_2$-$C_6$-alkenyl, $C_1$-$C_6$-haloalkyl, $C_2$-$C_6$-haloalkenyl, $C_1$-$C_6$-hydroxyalkyl, hydroxycarbonyl-$C_1$-$C_4$-alkyl, phenyl-$C_1$-$C_4$-alkyl or phenyl-$C_1$-$C_4$-hydroxyalkyl.

The examples below serve to illustrate the invention.

PREPARATION EXAMPLES

Example 1

1-{Methylcarbamoyl-[(1-methyl-3-trifluoromethyl-1H-pyrazol-4-carbonyl)amino]methyl}-allyl acetate (Tab. 3 No. 3.10)

1.1) Ethyl [(1-methyl-3-trifluoromethyl-1H-pyrazole-4-carbonyl)amino]acetate

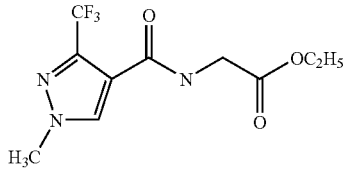

3.63 g (25.8 mmol) of ethyl glycinate hydrochloride were dissolved in $CH_2Cl_2$, and THF, 5.00 g (25.8 mmol) of 1-methyl-3-trifluoromethyl-4-carboxylic acid and 7.82 g of triethylamine (77.3 mmol) were added at RT and 6.56 g (25.8 mmol) of bis-(2-oxo)-3-oxazolidinyl)phosphonyl chloride were added at 0° C. The mixture was stirred at 0° C. for 3 h and then at RT for 16 h. The solvents were then removed, the residue was taken up in ethyl acetate, washed and dried and the solvent was removed. This gave 3.88 g (54% of theory) of the title compound as a red oil.

$^1$H-NMR (DMSO): δ=1.20 (t, 3H); 3.95 (s, 6H); 4.15 (q, 2H); 8.35 (s, 1H); 8.65 (t, 1H).

1.2) Ethyl 3-hydroxy-2-[(1-methyl-3-trifluoromethyl-1H-pyrazole-4-carbonyl)amino]pent-4-enoate (Tab. 2, No. 2.2)

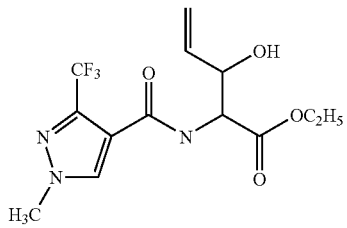

At −50° C., 3.45 g (12.4 mmol) of ethyl [(1-methyl-3-trifluoromethyl-1H-pyrazole-4-carbonyl)amino]acetate dissolved in THF were added dropwise to 18.5 ml (37.0 mmol) of a 2M solution of lithium diisopropylamide in THF/heptanelethylbenzene. After 1.5 h of stirring at −50° C., the mixture was cooled to −78° C. and 0.83 g (14.8 mmol) of acrolein dissolved in THF were added dropwise. After 2 h of stirring at −78° C., the mixture was hydrolyzed with sat. NH$_4$Cl solution and warmed to RT. After separation of the phases, the organic phase was dried and the solvent was removed. The residue was purified chromatographically (SiO$_2$, cyclohexane/ethyl acetate). This gave 1.65 g (40% of theory) of the title compound as a colorless solid (about 1:1 diastereomer mixture) which was used without further purification.

1.3) N-(2-Hydroxy-1-methylcarbamoylbut-3-enyl)-1-methyl-3-trifluoromethyl-1H-pyrazole-4-carboxamide (Tab. 3, No. 3.4)

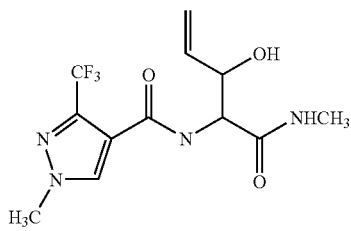

1.65 g (4.92 mmol) of ethyl 3-hydroxy-2-[(1-methyl-3-trifluoromethyl-1H-pyrazole-4-carbonyl)amino]pent-4-enoate were dissolved in methanol. At 0° C., methylamine gas was introduced for 1 h. After 16 h of stirring at RT, the solvent was removed and the residue was recrystallized from acetone. The precipitate gave 0.65 g of erythro title compound as a colorless powder, the filtrate contained 0.75 g of isomer mixture. Accordingly, the total yield was 1.40 g (89% of theory).

$^1$H-NMR (DMSO) (erythro isomer): δ=2.55 (d, 3H); 4.95 (s, 3H); 4.25 (m, 1H); 4.35 (t, 1H); 5.10 (d, 1H); 5.25 (d, 1H); 5.35 (d, 1H); 5.80 (m, 1H); 7.95 (d, 1H); 8.10 (d, 1H); 8.45 (s, 1H).

1.4) 1-{Methylcarbamoyl-[(1-methyl-3-trifluoromethyl-1H-pyrazole-4-carbonyl)amino]-methyl}allyl acetate (Tab. 3 No. 3.10)

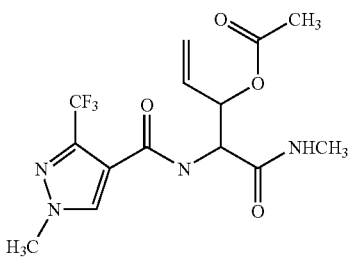

134 mg (0.42 mmol) of N-(2-hydroxy-1-methylcarbamoylbut-3-enyl)-1-methyl-3-trifluoromethyl-1H-pyrazole-4-carboxamide, 28 mg (0.46 mmol) of acetic acid and 20 mg (0.17 mmol) of dimethylaminopyridine were dissolved in CH$_2$Cl$_2$. At 0° C., 88 mg (0.46 mmol) of 1-(3-dimethylaminopropyl)-3-(ethylcarbodiimide) hydrochloride were added. After 16 h of stirring at RT, the reaction solution was washed and the solvent was removed. This gave 0.10 g (66% of theory) of the title compound as a colorless powder (M+(m/z)=362).

In addition to the above compounds, further heteroaroyl derivatives of the formula III and heteroaroyl-substituted serineamides of the formula I which were prepared or are preparable in a manner analogously to the processes described above are listed in Tables 2 and 3 below.

TABLE 2

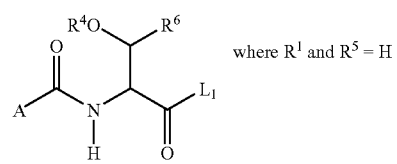

where R$^1$ and R$^5$ = H

III

| No. | A | R$^4$ | R$^6$ | L$^1$ | Diastereomer ration | Chirality | M+ (m/z) |
|---|---|---|---|---|---|---|---|
| 2.1. | 1-CH$_3$-3-CF$_3$-4-pyrazolyl | H | CF$_3$ | OC$_2$H$_5$ | 3:2 | rac. | 377 |
| 2.2. | 1-CH$_3$-3-CF$_3$-4-pyrazolyl | H | CH=CH$_2$ | OC$_2$H$_5$ | 1:1 | rac. | 335 |
| 2.3. | 1-CH$_3$-3-CF$_3$-4-pyrazolyl | H | C≡CH | OC$_2$H$_5$ | 1:1 | rac. | 333 |
| 2.4. | 1-CH$_3$-3-CF$_3$-4-pyrazolyl | H | 4-2H-tetrahydropyranyl | | | | |

TABLE 3

$$\text{Structure I: } R^4O-C(=O)-N(H)-A, \text{ with } CH(R^6)(NH) \text{ and } C(=O)NHCH_3 \text{ groups}$$

where $R^1$, $R^2$ and $R^5$ = H
$R^3$ = CH3

| No. | A | $R^4$ | $R^6$ | Diastereomer ratio | Chirality | M.p. | M+ (m/z) |
|---|---|---|---|---|---|---|---|
| 3.1. | 1-$CH_3$-3-$CF_3$-4-pyrazolyl | H | H | — | 2-S | 160 | |
| 3.2. | 1-$CH_3$-3-$CF_3$-4-pyrazolyl | H | $CH_3$ | 1:0 | 2-S | 141 | |
| 3.3. | 1-$CH_3$-3-$CF_3$-4-pyrazolyl | H | $C(CH_3)_3$ | 1:0 | 2-S | 166 | |
| 3.4. | 1-$CH_3$-3-$CF_3$-4-pyrazolyl | H | $CH=CH_2$ | 1:1 | rac. | 136 | 320 |
| 3.5. | 1-$CH_3$-3-$CF_3$-4-pyrazolyl | H | $CH=(CH_3)_2$ | 1:0 | 2-S | 130 | |
| 3.6. | 1-$CH_3$-3-$CF_3$-4-pyrazolyl | H | $C\equiv CH$ | 1:1 | rac. | 160 | 318 |
| 3.7. | 1-$CH_3$-3-$CF_3$-4-pyrazolyl | H | $CF_3$ | 3:2 | rac. | 188 | 362 |
| 3.8. | 1-$CH_3$-3-$CF_3$-4-pyrazolyl | H | $CH_2(C_6H_5)$ | 6:1 | rac. | 146 | |
| 3.9. | 1-$CH_3$-3-$CF_3$-4-pyrazolyl | $(CO)CH_3$ | $CH_3$ | 1:0 | 2-S | 197 | |
| 3.10. | 1-$CH_3$-3-$CF_3$-4-pyrazolyl | $(CO)CH_3$ | $CH=CH_2$ | 1:1 | rac. | 160 | 362 |
| 3.11. | 1-$CH_3$-3-$CF_3$-4-pyrazolyl | $(CO)C(CH_3)_3$ | $CF_3$ | 3:2 | rac. | 210 | 446 |
| 3.12. | 1-$CH_3$-3-$CF_3$-4-pyrazolyl | $(CO)N(CH_3)_2$ | $CF_3$ | 1:1 | rac. | 213 | 433 |
| 3.13. | 1-$CH_3$-3-$CF_3$-4-pyrazolyl | $(CO)N(CH_3)_2$ | $CH=CH_2$ | 1:1 | rac. | 106 | 391 |
| 3.14. | 3-$CF_3$-4-thienyl | H | $CH_2(C_6H_5)$ | 1:0 | rac. | 160 | |
| 3.15 | 1-$CH_3$-3-$CF_3$-4-pyrazolyl | $(CH_3)_2CHNHCO$ | $CH_3$ | 1:0 | 2-S, 3-R | | 393 |
| 3.16 | 1-$CH_3$-3-$CF_3$-4-pyrazolyl | $(CH_3)_2NCO$ | 2,2-$Cl_2$-cyclopropyl | 1:1 | rac. | 166 | |
| 3.17 | 1-$CH_3$-3-$CF_3$-4-pyrazolyl | $(CH_3)_2NCO$ | 3-2H-tetrahydropyranyl | 1:1 | rac. | 197 | |
| 3.18 | 1-$CH_3$-3-$CF_3$-4-pyrazolyl | $(CH_3)_2NCO$ | 4-2H-tetrahydropyranyl | 1:0 | rac. | 220 | |
| 3.19 | 1-$CH_3$-3-$CF_3$-4-pyrazolyl | $(CH_3)_2NCO$ | 4-2H-tetrahydropyranyl | 0:1 | rac. | 221 | |
| 3.20 | 1-$CH_3$-3-$CF_3$-4-pyrazolyl | $(CH_3)_2NCO$ | 5-$(CH_3)_2$-2-tetrahydrofuryl | 1:1 | rac. | 181 | |
| 3.21 | 1-$CH_3$-3-$CF_3$-4-pyrazolyl | $(CH_3)_2NCO$ | $CH(CH_3)O(2,4-Cl_2-C_6H_3)$ | 1:0 | rac. | 188 | |
| 3.22 | 1-$CH_3$-3-$CF_3$-4-pyrazolyl | $(CH_3)_2NCO$ | $CH(CH_3)O(2,4-Cl_2-C_6H_3)$ | 2:1 | rac. | 182 | |
| 3.23 | 1-$CH_3$-3-$CF_3$-4-pyrazolyl | $(CH_3)_2NCO$ | $CH(OCOCH_3)CH(OCOCH_3)(2$-Cl-5-$NO_2C_6H_3)$ | 5:1 | rac. | 105 | |
| 3.24 | 1-$CH_3$-3-$CF_3$-4-pyrazolyl | $(CH_3)_2NCO$ | $CH(OCOCH_3)CH(OCOCH_3)(3,5-Cl_2-C_6H_3)$ | 1:1 | rac. | 225 | |
| 3.25 | 1-$CH_3$-3-$CF_3$-4-pyrazolyl | $(CH_3)_2NCO$ | $CH(OCON(CH_3)_2)CH(OCON(CH_3)_2)$—$CONHCH_3$ | 1:1 | rac. | | 624 |
| 3.26 | 1-$CH_3$-3-$CF_3$-4-pyrazolyl | $(CH_3)_2NCO$ | $CH(OH)C(CH_3)_2(OH)$ | 1:1 | rac. | 120 | |
| 3.27 | 1-$CH_3$-3-$CF_3$-4-pyrazolyl | $(CH_3)_2NCO$ | $CH(OH)CH(OH)(2$-Cl-5-$NO_2$—$C_6H_3)$ | 1:1 | rac. | 104 | |
| 3.28 | 1-$CH_3$-3-$CF_3$-4-pyrazolyl | $(CH_3)_2NCO$ | $CH(OH)CH(OH)(4$-Cl—$C_6H_4)$ | 1:1 | rac. | 119 | |
| 3.29 | 1-$CH_3$-3-$CF_3$-4-pyrazolyl | $(CH_3)_2NCO$ | $CH(OH)CH_2(OH)$ | 1:1 | rac. | | 425 |
| 3.30 | 1-$CH_3$-3-$CF_3$-4-pyrazolyl | $(CH_3)_2NCO$ | $CH[OCON(CH_3)_2]CH_2[OCON(CH_3)_2]$ | 1:1 | rac. | | 567 |
| 3.31 | 1-$CH_3$-3-$CF_3$-4-pyrazolyl | $(CH_3)_2NCO$ | $CH=C(CH_3)_2$ | 1:0 | rac. | 190 | |
| 3.32 | 1-$CH_3$-3-$CF_3$-4-pyrazolyl | $(CH_3)_2NCO$ | $CH=CH(2$-Cl-5-$NO_2$—$C_6H_3)$ | 5:1 | rac. | | 546 |
| 3.33 | 1-$CH_3$-3-$CF_3$-4-pyrazolyl | $(CH_3)_2NCO$ | $CH=CH(3,5-Cl_2-C_6H_3)$ | 1:2 | rac. | 160 | |
| 3.34 | 1-$CH_3$-3-$CF_3$-4-pyrazolyl | $(CH_3)_2NCO$ | $CH=CH(4$-Cl—$C_6H_4)$ | 1:0 | rac. | 175 | |
| 3.35 | 1-$CH_3$-3-$CF_3$-4-pyrazolyl | $(CH_3)_2NCO$ | $CH=CH(4$-Cl—$C_6H_4)$ | 3:2 | rac. | 185 | |
| 3.36 | 1-$CH_3$-3-$CF_3$-4-pyrazolyl | $(CH_3)_2NCO$ | $CH=CH(5$-Cl-2-thienyl) | 1:0 | rac. | 200 | |
| 3.37 | 1-$CH_3$-3-$CF_3$-4-pyrazolyl | $(CH_3)_2NCO$ | $CH_2NH_3^+Cl^-$ | 3:1 | rac. | | 430 |
| 3.38 | 1-$CH_3$-3-$CF_3$-4-pyrazolyl | $(CH_3)_2NCO$ | $CH_2NHCO(2$-F—$C_6H_4)$ | 5:1 | rac. | 84 | |
| 3.39 | 1-$CH_3$-3-$CF_3$-4-pyrazolyl | $(CH_3)_2NCO$ | $CH2NHCOCH_3$ | 4:1 | rac. | | 436 |
| 3.40 | 1-$CH_3$-3-$CF_3$-4-pyrazolyl | $(CH_3)_2NCO$ | $CH_2NHCONHCH_3$ | 1:0 | rac. | 210 | |
| 3.41 | 1-$CH_3$-3-$CF_3$-4-pyrazolyl | $(CH_3)_2NCO$ | $CH_2NHCOOC(CH_3)_3$ | 1:0 | rac. | 137 | |
| 3.42 | 1-$CH_3$-3-$CF_3$-4-pyrazolyl | $(CH_3)_2NCO$ | $CH_2OCH_3$ | 3:1 | rac. | 180 | |
| 3.43 | 1-$CH_3$-3-$CF_3$-4-pyrazolyl | $(CH_3)_2NCO$ | $CH_2OH$ | 2:1 | rac. | 157 | |
| 3.44 | 1-$CH_3$-3-$CF_3$-4-pyrazolyl | $(CH_3)_2NCO$ | $CH_3$ | 1:0 | 2-S, 3-R | 152 | |
| 3.45 | 1-$CH_3$-3-$CF_3$-4-pyrazolyl | $(CH_3)_2NCO$ | $CHO(COCH_3)CHO(COCH_3)(5$-Cl-2-thienyl) | 1:1 | rac. | 160 | |
| 3.46 | 1-$CH_3$-3-$CF_3$-4-pyrazolyl | $(CH_3)_2NCO$ | $CHOHCHOH(3,5-Cl_2-C_6H_3)$ | 1:1 | rac. | 125 | |
| 3.47 | 1-$CH_3$-3-$CF_3$-4-pyrazolyl | $(CH_3)_2NCO$ | $CHOHCHOH(5$-Cl-2-thienyl) | 1:1 | rac. | | 541 |
| 3.48 | 1-$CH_3$-3-$CF_3$-4-pyrazolyl | $(CH_3)_2NCO$ | cyclopropyl | 2:1 | rac. | 184 | |
| 3.49 | 1-$CH_3$-3-$CF_3$-4-pyrazolyl | $(CH_3)_2NCO$ | cyclopropyl | 6:1 | rac. | | 405 |
| 3.50 | 1-$CH_3$-3-$CF_3$-4-pyrazolyl | $(CH_3)_2NCO$ | cyclopropyl | 1:6 | rac. | | 405 |
| 3.51 | 1-$CH_3$-3-$CF_3$-4-pyrazolyl | $(CH_3)_3C(CH_3)_2Si$ | $CH_3$ | 1:0 | 2-S, 3-R | 88 | |
| 3.52 | 1-$CH_3$-3-$CF_3$-4-pyrazolyl | $C_2H_5NHCO$ | $CH_3$ | 1:0 | 2-S, 3-R | | 379 |
| 3.53 | 1-$CH_3$-3-$CF_3$-4-pyrazolyl | $C_6H_5NHCO$ | $CH_3$ | 1:0 | 2-S, 3-R | 209 | |
| 3.54 | 1-$CH_3$-3-$CF_3$-4-pyrazolyl | $CH_3(CH_3O)NCO$ | 4-2H-tetrahydropyranyl | 0:1 | rac. | 224 | |
| 3.55 | 1-$CH_3$-3-$CF_3$-4-pyrazolyl | $CH_3CO$ | 3-2H-tetrahydropyranyl | 1:1 | rac. | 186 | |
| 3.56 | 1-$CH_3$-3-$CF_3$-4-pyrazolyl | $CH_3CO$ | 4-2H-tetrahydropyranyl | 1:0 | rac. | 178 | |
| 3.57 | 1-$CH_3$-3-$CF_3$-4-pyrazolyl | $CH_3CO$ | 5-$(CH_3)_2$-2-tetrahydrofuryl | 1:1 | rac. | 185 | |
| 3.58 | 1-$CH_3$-3-$CF_3$-4-pyrazolyl | $CH_3CO$ | $CH(CH_3)O(2,4-Cl_2-C_6H_3)$ | 1:1 | rac. | | 525 |
| 3.59 | 1-$CH_3$-3-$CF_3$-4-pyrazolyl | $CH_3CO$ | $CH(OH)CH(OH)(4$-Cl—$C_6H_4)$ | 1:1 | rac. | | 506 |
| 3.60 | 1-$CH_3$-3-$CF_3$-4-pyrazolyl | $CH_3CO$ | $CH=C(CH_3)_2$ | 3:1 | rac. | | 390 |
| 3.61 | 1-$CH_3$-3-$CF_3$-4-pyrazolyl | $CH_3CO$ | $CH=CH(4$-Cl—$C_6H_4)$ | 3:1 | rac. | 130 | |
| 3.62 | 1-$CH_3$-3-$CF_3$-4-pyrazolyl | $CH_3CO$ | $CH_3$ | 1:0 | 2-R, 3-S | 198 | |
| 3.63 | 1-$CH_3$-3-$CF_3$-4-pyrazolyl | $CH_3CO$ | $CH_3$ | 1:0 | 2-R, 3-S | 176 | |
| 3.64 | 1-$CH_3$-3-$CF_3$-4-pyrazolyl | $CH_3CO$ | cyclopropyl | 2:1 | rac. | 201 | |

TABLE 3-continued $$\text{Structure I: } R^4O-C(=O)-N(H)-A, \text{ attached to } CH(R^6)-CH(NHCH_3)(C=O) \text{ with central } CH$$

where $R^1$, $R^2$ and $R^5$ = h
$R^3$ = CH3

| No. | A | $R^4$ | $R^6$ | Diastereomer ratio | Chirality | M.p. | M+ (m/z) |
|---|---|---|---|---|---|---|---|
| 3.65 | 1-CH₃-3-CF₃-4-pyrazolyl | CH₃HNCO | 3-2H-tetrahydropyranyl | 1:1 | rac. | 186 | |
| 3.66 | 1-CH₃-3-CF₃-4-pyrazolyl | CH₃HNCO | 4-2H-tetrahydropyranyl | 1:1 | rac. | 151 | |
| 3.67 | 1-CH₃-3-CF₃-4-pyrazolyl | CH₃H NCO | 4-2H-tetrahydropyranyl | 0:1 | rac. | 238 | |
| 3.68 | 1-CH₃-3-CF₃-4-pyrazolyl | CH₃HNCO | 4-2H-tetrahydropyranyl | 1:0 | rac. | 220 | |
| 3.69 | 1-CH₃-3-CF₃-4-pyrazolyl | CH₃HNCO | 5-(CH₃)₂-2-tetrahydrofuryl | 1:1 | rac. | | 449 |
| 3.70 | 1-CH₃-3-CF₃-4-pyrazolyl | CH₃HNCO | CH(CH₃)O(2,4-Cl₂—C₆H₃) | 1:1 | rac. | 218 | |
| 3.71 | 1-CH₃-3-CF₃-4-pyrazolyl | CH₃HNCO | CH₃ | 1:0 | 2-S, 3-R | 239 | |
| 3.72 | 1-CH₃-3-CF₃-4-pyrazolyl | CH₃HNCO | cyclopropyl | 2:1 | rac. | 227 | |
| 3.73 | 1-CH₃-3-CF₃-4-pyrazolyl | CH₃OCO | CH₃ | 1:0 | 2-R, 3-S | 128 | |
| 3.74 | 1-CH₃-3-CF₃-4-pyrazolyl | CH₃OCO | CH₃ | 1:0 | 2-S, 3-R | 130 | |
| 3.75 | 1-CH₃-3-CF₃-4-pyrazolyl | CH₃OCO | CH₃ | 1:0 | 2-S, 3-S | 138 | |
| 3.76 | 1-CH₃-3-CF₃-4-pyrazolyl | H | 2,2-Cl₂-cyclopropyl | 1:1 | rac. | | 403 |
| 3.77 | 1-CH₃-3-CF₃-4-pyrazolyl | H | 3-2H-tetrahydropyranyl | 1:1 | rac. | 167 | |
| 3.78 | 1-CH₃-3-CF₃-4-pyrazolyl | H | 4-2H-tetrahydropyranyl | 3:2 | rac. | 176 | |
| 3.79 | 1-CH₃-3-CF₃-4-pyrazolyl | H | 4-2H-tetrahydropyranyl | 1:0 | rac. | 230 | |
| 3.80 | 1-CH₃-3-CF₃-4-pyrazolyl | H | 4-2H-tetrahydropyranyl | 0:1 | rac. | 230 | |
| 3.81 | 1-CH₃-3-CF₃-4-pyrazolyl | H | 5-(CH₃)₂-2-tetrahydrofuryl | 1:1 | rac. | 184 | |
| 3.82 | 1-CH₃-3-CF₃-4-pyrazolyl | H | CH(CH₃)O(2,4-Cl₂—C₆H₃) | 1:0 | rac. | 209 | |
| 3.83 | 1-CH₃-3-CF₃-4-pyrazolyl | H | CH(CH₃)O(2,4-Cl₂—C₆H₃) | 2:1 | rac. | 130 | |
| 3.84 | 1-CH₃-3-CF₃-4-pyrazolyl | H | CH(OH)CH(OH)CONHCH₃ | 1:1 | rac. | | 411 |
| 3.85 | 1-CH₃-3-CF₃-4-pyrazolyl | H | CH=C(CH₃)₂ | 4:1 | rac. | 134 | |
| 3.86 | 1-CH₃-3-CF₃-4-pyrazolyl | H | CH=CH(2-Cl-5-NO₂—C₆H₃) | 5:1 | rac. | 207 | |
| 3.87 | 1-CH₃-3-CF₃-4-pyrazolyl | H | CH=CH(2-Cl-5-NO₂—C₆H₃) | 1:0 | rac. | 235 | |
| 3.88 | 1-CH₃-3-CF₃-4-pyrazolyl | H | CH=CH(3,5-Cl₂—C₆H₃) | 1:2 | rac. | 225 | |
| 3.89 | 1-CH₃-3-CF₃-4-pyrazolyl | H | CH=CH(4-Cl—C₆H₄) | 1:0 | rac. | 240 | |
| 3.90 | 1-CH₃-3-CF₃-4-pyrazolyl | H | CH=CH(4-OCH₃—C₆H₄) | 1:0 | rac. | 215 | |
| 3.91 | 1-CH₃-3-CF₃-4-pyrazolyl | H | CH=CH(5-Cl-2-thienyl) | 3:2 | rac. | 190 | |
| 3.92 | 1-CH₃-3-CF₃-4-pyrazolyl | H | CH₂NH₃⁺Cl⁻ | 2:1 | rac. | | 359 |
| 3.93 | 1-CH₃-3-CF₃-4-pyrazolyl | H | CH₂NHCOOC(CH₃)₃ | 3:1 | rac. | | 423 |
| 3.94 | 1-CH₃-3-CF₃-4-pyrazolyl | H | CH₂NHCOOC(CH₃)₃ | 0:1 | rac. | | 423 |
| 3.95 | 1-CH₃-3-CF₃-4-pyrazolyl | H | CH₂OCH₃ | 3:2 | rac. | 155 | |
| 3.96 | 1-CH₃-3-CF₃-4-pyrazolyl | H | CH₃ | 1:0 | 2-S, 3-S | 160 | |
| 3.97 | 1-CH₃-3-CF₃-4-pyrazolyl | H | CH₃ | 1:0 | 2-R, 3-S | 151 | |
| 3.98 | 1-CH₃-3-CF₃-4-pyrazolyl | H | cyclopropyl | 3:1 | rac. | | 334 |
| 3.99 | 1-CH₃-3-CF₃-4-pyrazolyl | H₂NCO | CH₃ | 1:0 | 2-S, 3-R | 351 | |
| 3.100 | 1-CH₃-3-CF₃-5-F-4-pyrazolyl | (CH₃)₂NCO | cyclopropyl | 0:1 | rac. | | 423 |
| 3.101 | 1-CH₃-3-CF₃-5-F-4-pyrazolyl | H | 4-2H-tetrahydropyranyl | 1:2 | rac. | 222 | |
| 3.102 | 1-CH₃-3-CF₃-5-F-4-pyrazolyl | H | cyclopropyl | 0:1 | rac. | | 352 |
| 3.103 | 2-CH₃-5-CF₃-4-oxazolyl | (CH₃)₂NCO | cyclopropyl | 1:1 | rac. | | 406 |
| 3.104 | 2-CH₃-5-CF₃-4-oxazolyl | H | cyclopropyl | 0:1 | rac. | | 335 |
| 3.105 | 3-CF₃-4-thienyl | (CH₃)₂NCO | cyclopropyl | 0:1 | rac. | 120 | |
| 3.106 | 3-CF₃-4-thienyl | H | cyclopropyl | 1:5 | rac. | | 336 |
| 3.107 | 5-CH₃-2-CF₃-3-furyl | (CH₃)₂NCO | cyclopropyl | 0:1 | rac. | 175 | |
| 3.108 | 5-CH₃-2-CF₃-3-furyl | H | cyclopropyl | 0:1 | rac. | | 334 |

Biological Activity

The heteroaroyl-substituted serineamides of the formula I and their agriculturally useful salts are suitable, both in the form of isomer mixtures and in the form of the pure isomers, as herbicides. The herbicidal compositions comprising compounds of the formula I control vegetation on non-crop areas very efficiently, especially at high rates of application. They act against broad-leaved weeds and grass weeds in crops such as wheat, rice, maize, soya and cotton without causing any significant damage to the crop plants. This effect is mainly observed at low rates of application.

Depending on the application method in question, the compounds of the formula I, or herbicidal compositions comprising them, can additionally be employed in a further number of crop plants for eliminating undesirable plants. Examples of suitable crops are the following:

*Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum* (*N. rustica*), *Olea europaea, Oryza sativa, Phaseolus lunatus, Phaseolus vulgaris, Picea abies, Pinus* spec., *Pisum sativum, Prunus avium, Prunus persica, Pyrus communis, Ribes*

*sylvestre, Ricinus communis, Saccharum officinarum, Secale cereale, Solanum tuberosum, Sorghum bicolor (s. vulgare), Theobroma cacao, Trifolium pratense, Triticum aestivum, Triticum durum, Vicia faba, Vitis vinifera* and *Zea mays.*

In addition, the compounds of the formula I may also be used in crops which tolerate the action of herbicides owing to breeding, including genetic engineering methods.

In addition, the compounds of the formula I may also be used in crops which tolerate attack by fungi or insects owing to breeding, including genetic engineering methods.

The compounds of the formula I, or the herbicidal compositions comprising them, can be used for example in the form of ready-to-spray aqueous solutions, powders, suspensions, also highly concentrated aqueous, oily or other suspensions or dispersions, emulsions, oil dispersions, pastes, dusts, materials for broadcasting, or granules, by means of spraying, atomizing, dusting, spreading or watering. The use forms depend on the intended purpose; in any case, they should guarantee the finest possible distribution of the active ingredients according to the invention.

The herbicidal compositions comprise a herbicidally effective amount of at least one compound of the formula I or an agriculturally useful salt of I, and auxiliaries which are customary for the formulation of crop protection agents.

Suitable as inert auxiliaries are essentially the following: mineral oil fractions of medium to high boiling point, such as
  kerosene and diesel oil, furthermore coal tar oils and oils of vegetable or animal origin, aliphatic, cyclic and aromatic hydrocarbons, e.g. paraffin, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, e.g. amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the substrates, either as such or dissolved in an oil or solvent, can be homogenized in water by means of a wetting agent, tackifier, dispersant or emulsifier. Alternatively, it is also possible to prepare concentrates comprising active substance, wetting agent, tackifier, dispersant or emulsifier and, if desired, solvent or oil, which are suitable for dilution with water.

Suitable surfactants (adjuvants) are the alkali metal salts, alkaline earth metal salts and ammonium salts of aromatic sulfonic acids, e.g. ligno-, phenol-, naphthalene- and dibutyl-naphthalenesulfonic acid, and of fatty acids, alkyl- and alkylarylsulfonates, alkyl sulfates, lauryl ether sulfates and fatty alcohol sulfates, and salts of sulfated hexa-, hepta- and octa-decanols, and also of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors or methylcellulose.

Powders, materials for broadcasting and dusts can be prepared by mixing or grinding the active ingredients together with a solid carrier.

Granules, e.g. coated granules, impregnated granules and homogeneous granules, can be prepared by binding the active ingredients to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate and magnesium oxide, ground synthetic materials, fertilizers such as ammonium sulfate, ammonium phosphate, ammonium nitrate and ureas, and products of vegetable origin, such as cereal meal, tree bark meal, wood meal and nutshell meal, cellulose powders, or other solid carriers.

The concentrations of the compounds of the formula I in the ready-to-use preparations can be varied within wide ranges. In general, the formulations comprise approximately from 0.001 to 98% by weight, preferably 0.01 to 95% by weight of at least one active ingredient. The active ingredients are employed in a purity of from 90% to 100%, preferably 95% to 100% (according to NMR spectrum).

The formulation examples below illustrate the preparation of such compositions:

I. 20 parts by weight of an active compound of the formula I are dissolved in a mixture composed of 80 parts by weight of alkylated benzene, 10 parts by weight of the adduct of from 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100 000 parts by weight of water and finely distributing it therein gives an aqueous dispersion which comprises 0.02% by weight of the active ingredient of the formula I.

II. 20 parts by weight of an active compound of the formula I are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100 000 parts by weight of water and finely distributing it therein gives an aqueous dispersion which comprises 0.02% by weight of the active ingredient of the formula I.

III. 20 parts by weight of an active compound of the formula I are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100 000 parts by weight of water and finely distributing it therein gives an aqueous dispersion which comprises 0.02% by weight of the active ingredient of the formula I.

IV. 20 parts by weight of an active compound of the formula I are mixed thoroughly with 3 parts by weight of sodium diisobutylnaphthalenesulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20 000 parts by weight of water gives a spray mixture which comprises 0.1% by weight of the active ingredient of the formula I.

V. 3 parts by weight of an active compound of the formula I are mixed with 97 parts by weight of finely divided kaolin. This gives a dust which comprises 3% by weight of the active ingredient of the formula I.

VI. 20 parts by weight of an active compound of the formula I are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of an active compound of the formula I is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII. 1 part by weight of an active compound of the formula I is dissolved in a mixture composed of 80 parts by weight of cyclohexanone and 20 parts by weight of Wettol® EM 31 (=nonionic emulsifier based on ethoxylated castor oil). This gives a stable emulsion concentrate.

The compounds of the formula I or the herbicidal compositions can be applied pre- or post-emergence. If the active ingredients are less well tolerated by certain crop plants, application techniques may be used in which the herbicidal compositions are sprayed, with the aid of the spraying equipment, in such a way that as far as possible they do not come into contact with the leaves of the sensitive crop plants, while the active ingredients reach the leaves of undesirable plants growing underneath, or the bare soil surface (post-directed, lay-by).

The rates of application of the compound of the formula I are from 0.001 to 3.0, preferably 0.01 to 1.0, kg/ha of active substance (a.s.), depending on the control target, the season, the target plants and the growth stage.

To widen the spectrum of action and to achieve synergistic effects, the heteroaroyl-substituted serineamides of the formula I may be mixed with a large number of representatives of other herbicidal or growth-regulating active ingredient groups and then applied concomitantly. Suitable components for mixtures are, for example, 1,2,4-thiadiazoles, 1,3,4-thiadiazoles, amides, aminophosphoric acid and its derivatives, aminotriazoles, anilides, (hetero)aryloxyalkanoic acids and their derivatives, benzoic acid and its derivatives, benzothiadiazinones, 2-(het)aroyl-1,3-cyclohexanediones, heteroaryl aryl ketones, benzylisoxazolidinones, meta-$CF_3$-phenyl derivatives, car-bamates, quinolinecarboxylic acid and its derivatives, chloroacetanilides, cyclohexe-none oxime ether derivatives, diazines, dichloropropionic acid and its derivatives, dihy-drobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and heteroaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

It may furthermore be beneficial to apply the compounds of the formula I alone or in combination with other herbicides, or in the form of a mixture with other crop protection agents, for example together with agents for controlling pests or phytopathogenic fungi or bacteria. Also of interest is the miscibility with mineral salt solutions, which are employed for treating nutritional and trace element deficiencies. Non-phytotoxic oils and oil concentrates may also be added.

Use Examples

The herbicidal activity of the heteroaroyl-substituted serineamides of the formula I was demonstrated by the following greenhouse experiments:

The culture containers used were plastic flowerpots containing loamy sand with approximately 3.0% of humus as the substrate. The seeds of the test plants were sown separately for each species.

For the pre-emergence treatment, the active ingredients, which had been suspended or emulsified in water, were applied directly after sowing by means of finely distributing nozzles. The containers were irrigated gently to promote germination and growth and subsequently covered with transparent plastic hoods until the plants had rooted. This cover causes uniform germination of the test plants, unless this has been impaired by the active ingredients.

For the post-emergence treatment, the test plants were first grown to a height of 3 to 15 cm, depending on the plant habit, and only then treated with the active ingredients which had been suspended or emulsified in water. For this purpose, the test plants were either sown directly and grown in the same containers, or they were first grown separately as seedlings and transplanted into the test containers a few days prior to treatment. The rate of application for the post-emergence treatment was 1.0 kg/ha of a.s. (active substance).

Depending on the species, the plants were kept at 10-25° C. or 20-35° C. The test period extended over 2 to 4 weeks. During this time, the plants were tended, and their response to the individual treatments was evaluated.

Evaluation was carried out using a scale from 0 to 100. 100 means no emergence of the plants, or complete destruction of at least the aerial parts, and 0 means no dam-age, or normal course of growth.

The plants used in the greenhouse experiments belonged to the following species:

| Scientific name | Common name |
|---|---|
| Amaranthus retroflexus | pig weed |
| Chenopodium album | lambsquarters |
| Polygonum convolvulus | black bindweed |

At application rates of 1 kg/ha, the compound 3.7 (Table 3) showed very good post-emergence action against the unwanted plants Amaranthus retroflexus and Chenopodium album.

Furthermore, compound 3.12 (Table 3), applied by the post-emergence method, ef-fected, at application rates of 1 kg/ha, very good control of the harmful plants Amaranthus retroflexus, Chenopodium album and Polygonum convolvulus.

We claim:
1. A heteroaroyl-substituted serineamide of the formula I

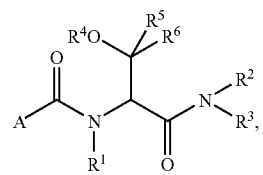

wherein
A is a 5-membered heteroaryl having one to four nitrogen atoms, or one to three nitrogen atoms and one oxygen or sulfur atom, or one oxygen or sulfur atom, which heteroaryl may be partially or fully halogenated and/or may carry 1 to 3 radicals from the group consisting of cyano, $C_1$-$C_6$-alkyl, $C_3$-$C_6$-cycloalkyl, $C_1$-$C_6$-haloalkyl, $C_1$-$C_6$-alkoxy, $C_1$-$C_6$-haloalkoxy and $C_1$-$C_6$-alkoxy-$C_1$-$C_4$-alkyl;

$R^1$, $R^2$ are hydrogen, hydroxyl or $C_1$-$C_6$-alkoxy;

$R^3$ is $C_1$-$C_6$-alkyl, $C_1$-$C_4$-cyanoalkyl or $C_1$-$C_6$-haloalkyl;

$R^4$ is hydrogen, $C_1$-$C_6$-alkyl, $C_3$-$C_6$-cycloalkyl, $C_3$-$C_6$-alkenyl, $C_3$-$C_6$-alkynyl, $C_3$-$C_6$-haloalkenyl, $C_3$-$C_6$-haloalkynyl, formyl, $C_1$-$C_6$-alkylcarbonyl, $C_3$-$C_6$-cycloalkylcarbonyl, $C_2$-$C_6$-alkenylcarbonyl, $C_2$-$C_6$-alkynylcarbonyl, $C_1$-$C_6$-alkoxycarbonyl, $C_3$-$C_6$-alkenyloxycarbonyl, $C_3$-$C_6$-alkynyloxycarbonyl, $C_1$-$C_6$alkylaminocarbonyl, $C_3$-$C_6$-alkenylaminocarbonyl, $C_3$-$C_6$-alkynylaminocarbonyl, $C_1$-$C_6$-alkylsulfonylaminocarbonyl, di($C_1$-$C_6$-alkyl)aminocarbonyl, N-($C_3$-$C_6$-alkenyl)-N-($C_1$-$C_6$-alkyl)aminocarbonyl, N-($C_3$-$C_6$-alkynyl)-N-($C_1$-$C_6$-alkyl)aminocarbonyl, N-($C_1$-$C_6$-alkoxy)-N-($C_1$-$C_6$-alkyl)aminocarbonyl, N-($C_3$-$C_6$-alkenyl)-N-($C_1$-$C_6$-alkoxy)aminocarbonyl, N-($C_3$-$C_6$-alkynyl)-N-($C_1$-$C_6$-alkoxy)aminocarbonyl, di($C_1$-$C_6$-alkyl)aminothiocarbonyl, ($C_1$-$C_6$-alkyl)cyanoimino, (amino)cyanoimino, [($C_1$-$C_6$-alkyl)amino]cyanoimino, [di($C_1$-$C_6$-alkyl)amino]cyanoimino, $C_1$-$C_6$-alkylcarbonyl-$C_1$-$C_6$-alkyl, $C_1$-$C_6$-alkoxyimino-$C_1$-$C_6$-alkyl, N-($C_1$-$C_6$-alkylamino)imino-$C_1$-$C_6$-alkyl, N-(di-$C_1$-$C_6$-alkylamino)imino-$C_1$-$C_6$-alkyl or tri-$C_1$-$C_4$-alkylsilyl, wherein the alkyl, cycloalkyl and alkoxy radicals mentioned may be partially or fully halogenated and/or may carry one to three of the following groups: cyano, hydroxyl, $C_3$-$C_6$-cycloalkyl, $C_1$-$C_6$-alkoxy-$C_1$-$C_4$-alkyl, $C_1$-$C_4$-alkoxy-$C_1$-$C_4$-alkoxy-$C_1$-$C_4$-alkyl, $C_1$-$C_4$-alkoxy, $C_1$-$C_4$-alkylthio, di($C_1$-$C_4$-alkyl)amino, $C_1$-$C_4$-alkyl-$C_1$-$C_6$-alkoxycarbonylamino, $C_1$-$C_4$-alkylcarbonyl, hydroxycarbonyl, $C_1$-$C_4$-alkoxycarbonyl, aminocarbonyl, $C_1$-$C_4$-alkylaminocarbonyl, di-($C_1$-$C_4$-alkyl)aminocarbonyl or $C_1$-$C_4$-alkylcarbonyloxy;

phenyl, phenyl-$C_1$-$C_6$-alkyl, phenylcarbonyl, phenylcarbonyl-$C_1$-$C_6$-alkyl, phenoxycarbonyl, phenylaminocarbonyl, phenylsulfonylaminocarbonyl, N-($C_1$-$C_6$-alkyl)-N-(phenyl)aminocarbonyl, phenyl-$C_1$-$C_6$-alkylcarbonyl, wherein the phenyl radical may be partially or fully halogenated and/or may carry one to three of the following groups: nitro, cyano, $C_1$-$C_4$-alkyl, $C_1$-$C_4$-haloalkyl, $C_1$-$C_4$-alkoxy or $C_1$-$C_4$-haloalkoxy; or $SO_2R^7$;

$R^5$ is hydrogen or $C_1$-$C_6$-alkyl;

$R^6$ is $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_1$-$C_6$-cyanoalkyl, $C_2$-$C_6$-cyanoalkenyl, $C_2$-$C_6$-cyanoalkynyl, $C_1$-$C_6$-hydroxyalkyl, $C_2$-$C_6$-hydroxyalkenyl, $C_2$-$C_6$-hydroxyalkynyl, $C_3$-$C_6$-cycloalkyl, $C_3$-$C_6$-cycloalkenyl, 3- to 6-membered heterocyclyl, 3- to 6-membered heterocyclyl-$C_1$-$C_4$-alkyl, where the cycloalkyl, cycloalkenyl or 3- to 6-membered heterocyclyl radicals mentioned above may be partially or fully halogenated and/or may carry one to three radicals from the group consisting of oxo, cyano, nitro, $C_1$-$C_6$-alkyl, $C_1$-$C_6$-haloalkyl, hydroxyl, $C_1$-$C_6$-alkoxy, $C_1$-$C_6$-haloalkoxy, hydroxycarbonyl, $C_1$-$C_6$-alkoxycarbonyl, hydroxycarbonyl-$C_1$-$C_6$-alkoxy, $C_1$-$C_6$-alkoxycarbonyl-$C_1$-$C_6$-alkoxy, amino, $C_1$-$C_6$-alkylamino, di($C_1$-$C_6$-alkyl)amino, $C_1$-$C_6$-alkylsulfonylamino, $C_1$-$C_6$-haloalkylsulfonylamino, aminocarbonylamino, ($C_1$-$C_6$-alkylamino)carbonylamino, di($C_1$-$C_6$-alkyl)-aminocarbonylamino, aryl and aryl($C_1$-$C_6$-alkyl);

$C_1$-$C_6$-alkoxy-$C_1$-$C_4$-alkyl, $C_2$-$C_6$-alkenyloxy-$C_1$-$C_4$-alkyl, $C_2$-$C_6$-alkynyloxy-$C_1$-$C_4$-alkyl, $C_1$-$C_6$-haloalkoxy-$C_1$-$C_4$-alkyl, $C_2$-$C_6$-haloalkenyloxy-$C_1$-$C_4$-alkyl, $C_2$-$C_6$-halo-alkynyloxy-$C_1$-$C_4$-alkyl, $C_1$-$C_6$-alkoxy-$C_1$-$C_4$-alkoxy-$C_1$-$C_4$-alkyl, $C_1$-$C_6$-alkylthio-$C_1$-$C_4$-alkyl, $C_2$-$C_6$-alkenylthio-$C_1$-$C_4$-alkyl, $C_2$-$C_6$-alkynylthio-$C_1$-$C_4$-alkyl, $C_1$-$C_6$-haloalkyl-$C_1$-$C_4$-thioalkyl, $C_2$-$C_6$-haloalkenyl-$C_1$-$C_4$-thioalkyl, $C_2$-$C_6$-haloalkynyl-$C_1$-$C_4$-thioalkyl, $C_1$-$C_6$-alkylsulfinyl-$C_1$-$C_4$-alkyl, $C_1$-$C_6$-haloalkylsulfinyl-$C_1$-$C_4$-alkyl, $C_1$-$C_6$-alkylsulfonyl-$C_1$-$C_4$-alkyl, $C_1$-$C_6$-haloalkylsulfonyl-$C_1$-$C_4$-alkyl, amino-$C_1$-$C_4$-alkyl, $C_1$-$C_6$-alkylamino-$C_1$-$C_4$-alkyl, di($C_1$-$C_6$-alkyl)amino-$C_1$-$C_4$-alkyl, $C_1$-$C_6$-alkylsulfonylamino-$C_1$-$C_4$-alkyl, $C_1$-$C_6$-alkylsulfonyl-($C_1$-$C_6$-alkylamino)-$C_1$-$C_4$-alkyl, $C_1$-$C_6$-alkylcarbonyl, hydroxycarbonyl, $C_1$-$C_6$-alkoxycarbonyl, aminocarbonyl, $C_1$-$C_6$-alkylaminocarbonyl, di($C_1$-$C_6$-alkyl)aminocarbonyl, $C_1$-$C_6$-alkylcarbonyl-$C_1$-$C_6$-alkyl, hydroxycarbonyl-$C_1$-$C_4$-alkyl, $C_1$-$C_6$-alkoxycarbonyl-$C_1$-$C_4$-alkyl, $C_1$-$C_6$-haloalkoxycarbonyl-$C_1$-$C_4$-alkyl, $C_1$-$C_6$-alkylcarbonyloxy-$C_1$-$C_4$-alkyl, aminocarbonyl-$C_1$-$C_4$-alkyl, $C_1$-$C_6$-alkylaminocarbonyl-$C_1$-$C_4$-alkyl, di($C_1$-$C_6$-alkyl)aminocarbonyl-$C_1$-$C_4$-alkyl, formylamino-$C_1$-$C_4$-alkyl, $C_1$-$C_6$-alkoxycarbonylamino-$C_1$-$C_4$-alkyl, $C_1$-$C_6$-alkylcarbonylamino-$C_1$-$C_4$-alkyl, $C_1$-$C_6$-alkylcarbonyl-($C_1$-$C_6$-alkylamino)-$C_1$-$C_4$-alkyl, [$C_1$-$C_6$-alkyl)aminocarbonyloxyl-$C_1$-$C_4$-alkyl, [di($C_1$-$C_6$-alkyl)aminocarbonyloxy]$C_1$-$C_4$-alkyl, {di[di($C_1$-$C_6$-alkyl)amino]carbonyloxy}$C_1$-$C_4$-alkyl, [($C_1$-$C_6$-alkylamino)carbonylamino]-$C_1$-$C_4$-alkyl, [di($C_1$-$C_6$-alkylamino)carbonylamino]-$C_1$-$C_4$-alkyl;

phenyl-$C_1$-$C_4$-alkyl, phenyl-$C_2$-$C_4$-alkenyl, phenyl-$C_2$-$C_4$-alkynyl, phenyl-$C_1$-$C_4$-haloalkyl, phenyl-$C_2$-$C_4$-haloalkenyl, phenyl-$C_2$-$C_4$-haloalkynyl, phenyl-$C_1$-$C_4$-hydroxyalkyl, phenyl-$C_2$-$C_4$-hydroxyalkenyl, phenyl-$C_2$-$C_4$-hydroxyalkynyl, phenylcarbonyl-$C_1$-$C_4$-alkyl, phenylcarbonylamino-$C_1$-$C_4$-alkyl, phenylcarbonyloxy-$C_1$-$C_4$-alkyl, phenyloxycarbonyl-$C_1$-$C_4$-alkyl, phenyloxy-$C_1$-$C_4$-alkyl, phenylthio-$C_1$-$C_4$-alkyl, phenylsulfinyl-$C_1$-$C_4$-alkyl, phenylsulfonyl-$C_1$-$C_4$-alkyl, heteroaryl-$C_1$-$C_4$-alkyl, heteroaryl-$C_2$-$C_4$-alkenyl, heteroaryl-$C_2$-$C_4$-alkynyl, heteroaryl-$C_1$-$C_4$-haloalkyl, heteroaryl-$C_2$-$C_4$-haloalkenyl, heteroaryl-$C_2$-$C_4$-haloalkynyl, heteroaryl-$C_1$-$C_4$-hydroxyalkyl, heteroaryl-$C_2$-$C_4$-hydroxyalkenyl, heteroaryl-$C_2$-$C_4$-hydroxyalkynyl, heteroarylcarbonyl-$C_1$-$C_4$-alkyl, heteroarylcarbonyloxy-$C_1$-$C_4$-alkyl, heteroaryloxycarbonyl-$C_1$-$C_4$-alkyl, heteroaryloxy-$C_1$-$C_4$-alkyl, heteroarylthio-$C_1$-$C_4$-alkyl, heteroarylsulfinyl-$C_1$-$C_4$-alkyl, heteroarylsulfonyl-$C_1$-$C_4$-alkyl, where the phenyl and heteroaryl radicals mentioned above may be partially or fully halogenated and/or may carry one to three radicals from the group consisting of cyano, nitro, $C_1$-$C_6$-alkyl, $C_1$-$C_6$-haloalkyl, hydroxy, $C_1$-$C_6$-alkoxy, $C_1$-$C_6$-haloalkoxy, hydroxycarbonyl, $C_1$-$C_6$-alkoxycarbonyl, hydroxycarbonyl-$C_1$-$C_6$-alkoxy, $C_1$-$C_6$-alkoxycarbonyl-$C_1$-$C_6$-alkoxy, amino, $C_1$-$C_6$-alkylamino, di($C_1$-$C_6$-alkyl)amino, $C_1$-$C_6$-alkylsulfonylamino, $C_1$-$C_6$-haloalkylsulfonylamino, ($C_1$-$C_6$-alkylamino)carbonylamino, di($C_1$-$C_6$-alkyl) aminocarbonyl-amino, aryl and aryl($C_1$-$C_6$-alkyl);

$R^7$ is $C_1$-$C_6$-alkyl, $C_1$-$C_6$-haloalkyl or phenyl, where the phenyl radical may be partially or fully halogenated and/or may carry one to three of the following groups: $C_1$-$C_6$-alkyl, $C_1$-$C_6$-haloalkyl or $C_1$-$C_6$-alkoxy;

or an agriculturally useful salt thereof.

2. The heteroaroyl-substituted serineamide of the formula I according to claim 1 where A is a 5-membered heteroaryl selected from the group consisting of pyrrolyl, thienyl, furyl, pyrazolyl, imidazolyl, thiazolyl, oxazolyl, and tetrazolyl; where the heteroaryl radicals mentioned may be partially or fully halogenated and optionally may include 1 to 3 radicals from the group consisting of cyano, $C_1$-$C_6$-alkyl, $C_3$-$C_6$-cycloalkyl, $C_1$-$C_6$-haloalkyl, $C_1$-$C_6$-alkoxy, $C_1$-$C_6$-haloalkoxy and $C_1$-$C_6$-alkoxy-$C_1$-$C_4$-alkyl.

3. The heteroaroyl-substituted serineamide of the formula I according to claim 1 where $R^1$, $R^2$ and $R^5$ are hydrogen.

4. The heteroaroyl-substituted serineamide of the formula I according to claim 1 where $R^6$ is $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_1$-$C_6$-cyanoalkyl, $C_1$-$C_6$-hydroxyalkyl, $C_2$-$C_6$-hydroxyalkenyl, $C_2$-$C_6$-hydroxyalkynyl, $C_3$-$C_6$-cycloalkyl, $C_3$-$C_6$-cycloalkenyl, 3- to 6-membered heterocyclyl, wherein the cycloalkyl, cycloalkenyl or 3- to 6-membered heterocyclyl radicals mentioned above may be partially or fully halogenated and/or may carry one to three radicals from the group consisting of oxo, $C_1$-$C_6$-alkyl, $C_1$-$C_6$-haloalkyl, hydroxycarbonyl and $C_1$-$C_6$-alkoxycarbonyl, $C_1$-$C_6$-haloalkoxy-$C_1$-$C_4$-alkyl, $C_1$-$C_6$-alkoxy-$C_1$-$C_4$-alkoxy-$C_1$-$C_4$-alkyl, $C_1$-$C_6$-alkylsulfonylamino-$C_1$-$C_4$-alkyl, hydroxycarbonyl, $C_1$-$C_6$-alkoxycarbonyl, hydroxycarbonyl-$C_1$-$C_4$-alkyl, $C_1$-$C_6$-alkoxycarbonyl-$C_1$-$C_4$-alkyl, $C_1$-$C_6$-haloalkoxycarbonyl-$C_1$-$C_4$-alkyl, $C_1$-$C_6$-alkylcarbonyloxy-$C_1$-$C_4$-alkyl, $C_1$-$C_6$-allcylcarbonylamino-$C_1$-$C_4$-alkyl, di($C_1$-$C_6$-alkyl)carbonylamino-$C_1$-$C_4$-alkyl, di($C_1$-$C_6$-alkyl)aminocarbonylamino-$C_1$-$C_4$-alkyl, [($C_1$-$C_6$-alkyl)aminocarbonyl]amino-$C_1$-$C_4$-alkyl, [di($C_1$-$C_6$-alkyl)aminocarbonyloxy]-$C_1$-$C_4$-alkyl, formylamino-$C_1$-$C_4$-alkyl, phenyl-$C_1$-$C_4$-alkyl, phenyl-$C_2$-$C_4$-alkenyl, phenyl-$C_2$-$C_4$-alkynyl, phenyl-$C_1$-$C_4$-haloalkyl, phenyl-$C_2$-$C_4$-haloalkenyl, phenyl-$C_1$-$C_4$-hydroxyalkyl, phenyloxy-$C_1$-$C_4$-alkyl, phenylthio-$C_1$-$C_4$-alkyl, phenylsulfinyl-$C_1$-$C_4$-alkyl, phenylsulfonyl-$C_1$-$C_4$-alkyl, heteroaryl-$C_1$-$C_4$-alkyl, heteroaryl-$C_1$-$C_4$-hydroxyalkyl, heteroaryloxy-$C_1$-$C_4$-alkyl, heteroarylthio-$C_1$-$C_4$-alkyl, heteroarylsulfinyl-$C_1$-$C_4$-alkyl, heteroarylsulfonyl-$C_1$-$C_4$-alkyl, wherein the phenyl and heteroaryl radicals mentioned above may be partially or fully halogenated and optionally may include one to three radicals from the group consisting of cyano, nitro, $C_1$-$C_6$-alkyl, $C_1$-$C_6$-haloalkyl, hydroxy, $C_1$-$C_6$-alkoxy, $C_1$-$C_6$-haloalkoxy, hydroxycarbonyl, $C_1$-$C_6$-alkoxycarbonyl, hydroxycarbonyl-$C_1$-$C_6$-alkoxy, $C_1$-$C_6$-alkyl-sulfonylamino and $C_1$-$C_6$-haloalkylsulfonylamino.

5. A process for preparing heteroaroyl-substituted serineamides of the formula I according to claim 1, wherein serine derivatives of the formula V

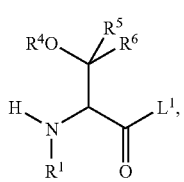

where $R^1$, $R^4$, $R^5$ and $R^6$ are as defined in claim 1 and $L^1$ is hydroxyl or $C_1$-$C_6$-alkoxy are reacted with heteroaryl acids/heteroaroyl acid derivatives of the formula IV

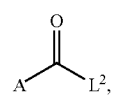

where A is as defined in claim 1 and $L^2$ is a hydroxyl, halogen, $C_1$-$C_6$-alkylcarbonyl, $C_1$-$C_6$-alkoxycarbonyl, $C_1$-$C_4$-alkylsulfonyl, phosphoryl or isoureyl to give the corresponding heteroaroyl derivatives of the formula III

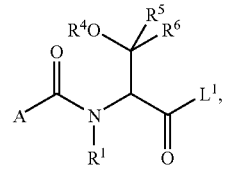

where A, $R^1$, $R^4$, $R^5$ and $R^6$ are as defined in claim 1 and $L^1$ is hydroxyl or $C_1$-$C_6$-alkoxy, and the resulting heteroaroyl derivatives of the formula III are then reacted with an amine of the formula II $HNR^2R^3$ II, where $R^2$ and $R^3$ are as defined in claim 1.

6. A process for preparing heteroaroyl-substituted serineamides of the formula I according to claim 1 where $R^4$ and $R^5$ are hydrogen, wherein heteroaroyl derivatives of the formula III where $R^4$ and $R^5$ are hydrogen are prepared by acylation of keto compounds of the formula XIII

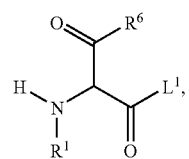

where $R^1$ is as defined in claim 1 and $L^1$ is hydroxyl or $C_1$-$C_6$-alkoxy with heteroaryl acids/heteroaroyl acid derivatives of the formula IV to give N-acyl keto compounds of the formula XII

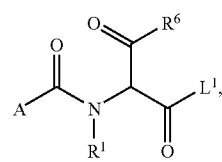

where A, $R^1$ and $R^6$ are as defined in claim 1 and $L^1$ is hydroxyl or $C_1$-$C_6$-alkoxy and subsequent reduction of the keto group.

7. A composition, comprising a herbicidally effective amount of at least one heteroaroyl-substituted serineamide of the formula I or an agriculturally useful salt of I according to claim 1 and auxiliaries customary for formulating crop protection agents.

8. A process for preparing compositions according to claim 7, wherein a herbicidally effective amount of at least one heteroaroyl-substituted serineamide of the formula I or an agriculturally useful salt of formula I according to claim 1 and auxiliaries customary for formulating crop protection agents are mixed.

9. A method for controlling unwanted vegetation, wherein a herbicidally effective amount of at least one heteroaroyl-substituted serineamide of the formula I or an agriculturally useful salt of formula I according to claim 1 is allowed to act on plants, their habitat and/or on seed.

* * * * *

UNITED STATES PATENT AND TRADEMARK OFFICE
CERTIFICATE OF CORRECTION

PATENT NO.         : 7,879,761 B2                                        Page 1 of 1
APPLICATION NO.    : 11/915227
DATED              : February 1, 2011
INVENTOR(S)        : Matthias Witschel et al.

It is certified that error appears in the above-identified patent and that said Letters Patent is hereby corrected as shown below:

Col. 63, line 22, before "$C_1$-$C_6$-haloalkoxy-$C_1$-$C_4$-alkyl,", insert
-- $C_1$-$C_6$-alkoxy-$C_1$-$C_4$-alkyl, --

Col. 63, line 23, before "$C_1$-$C_6$-alkylsulfonylamino-$C_1$-$C_4$ alkyl," insert
-- $C_1$-$C_6$-alkylthio-$C_1$-$C_4$-alkyl, --; and Col. 63, line 27-28, delete "$C_1$-$C_6$-allcylcarbonylamino-$C_1$-$C_4$-alkyl," and insert therefore
-- $C_1$-$C_6$-alkylcarbonylamino-$C_1$-$C_4$-alkyl, --

Signed and Sealed this
Twenty-first Day of June, 2011

David J. Kappos
*Director of the United States Patent and Trademark Office*